(12) United States Patent
Scherrer et al.

(10) Patent No.: US 12,202,804 B2
(45) Date of Patent: Jan. 21, 2025

(54) IN VITRO OR EX VIVO METHODS FOR SCREENING A QUINOLINE DERIVATIVE

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Didier Scherrer, Castelnau le Lez (FR); Jamal Tazi, Clapiers (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(*) Notice: Subject to any disclaimer, the term of this patent is extended or adjusted under 35 U.S.C. 154(b) by 0 days.

(21) Appl. No.: 17/746,410

(22) Filed: May 17, 2022

(65) Prior Publication Data

US 2022/0315535 A1    Oct. 6, 2022

Related U.S. Application Data

(62) Division of application No. 16/994,954, filed on Aug. 17, 2020, now Pat. No. 11,649,210, which is a division of application No. 16/554,748, filed on Aug. 29, 2019, now Pat. No. 10,981,874, which is a division of application No. 15/326,755, filed as application No. PCT/EP2015/066458 on Jul. 17, 2015, now Pat. No. 10,435,370.

(30) Foreign Application Priority Data

Jul. 17, 2014  (EP) .................................... 14306164

(51) Int. Cl.

| | | |
|---|---|---|
| *C07D 215/38* | (2006.01) |
| *A61K 31/47* | (2006.01) |
| *A61K 31/4709* | (2006.01) |
| *A61K 31/497* | (2006.01) |
| *A61K 31/5377* | (2006.01) |
| *C07D 401/12* | (2006.01) |
| *C12Q 1/6883* | (2018.01) |
| *G01N 33/50* | (2006.01) |

(52) U.S. Cl.
CPC ............ *C07D 215/38* (2013.01); *A61K 31/47* (2013.01); *A61K 31/4709* (2013.01); *A61K 31/497* (2013.01); *A61K 31/5377* (2013.01); *C07D 401/12* (2013.01); *C12Q 1/6883* (2013.01); *G01N 33/5023* (2013.01); *G01N 33/5055* (2013.01); *C12Q 2600/136* (2013.01); *C12Q 2600/158* (2013.01); *C12Q 2600/178* (2013.01)

(58) Field of Classification Search
CPC ............ C12Q 1/6883; C12Q 2600/136; C12Q 2600/158; C12Q 2600/178; G01N 33/5023; G01N 33/5055

See application file for complete search history.

(56) References Cited

U.S. PATENT DOCUMENTS

| | | |
|---|---|---|
| 2,605,182 A | 7/1952 | Peterson |
| 4,376,202 A | 3/1983 | Ura et al. |
| 4,425,343 A | 1/1984 | Sakata et al. |
| 4,434,290 A | 2/1984 | Bisagni et al. |
| 4,738,710 A | 4/1988 | Serban et al. |
| 6,180,632 B1 | 1/2001 | Myers et al. |
| 7,019,147 B1 | 3/2006 | Barth et al. |
| 8,394,796 B2 | 3/2013 | Castanedo et al. |
| 8,933,033 B2 | 1/2015 | Naylor et al. |
| 8,957,065 B2 | 2/2015 | Cha et al. |
| 9,061,999 B2 | 6/2015 | Tazi et al. |
| 9,108,919 B2 | 8/2015 | Roux et al. |
| 9,145,367 B2 | 9/2015 | Tazi et al. |
| 9,637,475 B2 | 5/2017 | Roux et al. |
| 9,827,237 B2 | 11/2017 | Tazi et al. |
| 10,017,498 B2 | 7/2018 | Tazi et al. |
| 10,253,020 B2 | 4/2019 | Tazi et al. |
| 10,435,370 B2 | 10/2019 | Tazi et al. |
| 10,683,284 B2 | 6/2020 | Tazi et al. |
| 10,981,874 B2 | 4/2021 | Scherrer et al. |
| 2003/0207886 A1 | 11/2003 | Plucker et al. |
| 2004/0038969 A1 | 2/2004 | Doherty et al. |

(Continued)

FOREIGN PATENT DOCUMENTS

| | | |
|---|---|---|
| DE | 958 647 C | 2/1957 |
| EP | 0 394 112 A2 | 10/1990 |

(Continued)

OTHER PUBLICATIONS

Ma, PLOS One, Apr. 2014, vol. 9(4), e92419, 1-12. (Year: 2014).*
Veremeyko, PLOS One, Dec. 2013, vol. 8(12), e81774, 1-13. (Year: 2013).*
Wang, Circulation Research, Jan. 2014, 67-78. (Year: 2014).*
Peng, J Mol Neurosci, 2013, vol. 50, 291-297. (Year: 2013).*
Zheng, Int J Mol MEd, vol. 31, 797-802, 2013. (Year: 2013).*

(Continued)

*Primary Examiner* — D Margaret M Seaman
(74) *Attorney, Agent, or Firm* — Oliff PLC

(57) ABSTRACT

In vitro or ex vivo methods for screening a quinoline derivative, or anyone of its pharmaceutically acceptable salt, presumed effective in treating and/or preventing an inflammatory disease, the method including: providing an eukaryotic cell, bringing into contact said cell with a quinoline derivative, measuring an expression of miR-124 in the cell, and selecting the candidate presumed effective in treating and/or preventing an inflammatory disease when the level of expression of miR-124 measured is increased relatively to a reference value.

19 Claims, 6 Drawing Sheets

Specification includes a Sequence Listing.

(56) References Cited

U.S. PATENT DOCUMENTS

| | | |
|---|---|---|
| 2004/0242603 A1 | 12/2004 | Fujiwara et al. |
| 2005/0085482 A1 | 4/2005 | Ramurthy et al. |
| 2005/0119225 A1 | 6/2005 | Schumacher et al. |
| 2006/0089380 A1 | 4/2006 | Barnham et al. |
| 2008/0119478 A1 | 5/2008 | Tsubouchi et al. |
| 2008/0161353 A1 | 7/2008 | Barnham et al. |
| 2008/0318984 A1 | 12/2008 | Verkman et al. |
| 2009/0227628 A1 | 9/2009 | Kolczewski et al. |
| 2010/0167948 A1 | 7/2010 | Krichevsky et al. |
| 2011/0003843 A1 | 1/2011 | Lejeune et al. |
| 2011/0111976 A1 | 5/2011 | Fare et al. |
| 2012/0202870 A1 | 8/2012 | Weiner et al. |
| 2012/0277230 A1 | 11/2012 | Roux et al. |
| 2012/0283265 A1 | 11/2012 | Tazi et al. |
| 2012/0329796 A1 | 12/2012 | Tazi et al. |
| 2013/0040988 A1 | 2/2013 | Deka et al. |
| 2013/0267703 A1 | 10/2013 | Tazi et al. |
| 2014/0051085 A1 | 2/2014 | Ding et al. |
| 2014/0080831 A1 | 3/2014 | Roux et al. |
| 2014/0288120 A1 | 9/2014 | Tazi et al. |
| 2015/0225796 A1 | 8/2015 | Snijders et al. |
| 2015/0299129 A1 | 10/2015 | Roux et al. |
| 2015/0307478 A1 | 10/2015 | Tazi et al. |
| 2015/0361491 A1 | 12/2015 | Tazi et al. |
| 2016/0041153 A1 | 2/2016 | Brown et al. |
| 2017/0204063 A1 | 7/2017 | Tazi et al. |
| 2017/0226095 A1 | 8/2017 | Tazi et al. |
| 2018/0030078 A1 | 2/2018 | Scherrer et al. |
| 2019/0077760 A1 | 3/2019 | Rabe et al. |
| 2019/0382347 A1 | 12/2019 | Scherrer et al. |
| 2020/0062713 A1 | 2/2020 | Rabe et al. |
| 2021/0047273 A1 | 2/2021 | Scherrer et al. |
| 2021/0087145 A1 | 3/2021 | Tazi et al. |
| 2022/0023324 A1* | 1/2022 | Pouletty .................. C07H 17/02 |

FOREIGN PATENT DOCUMENTS

| | | |
|---|---|---|
| EP | 1 897 914 A1 | 3/2008 |
| EP | 2 075 309 A2 | 7/2009 |
| EP | 2 266 972 A1 | 12/2010 |
| EP | 2 465 502 A1 | 6/2012 |
| EP | 2 757 161 A1 | 7/2014 |
| EP | 2 974 729 A1 | 1/2016 |
| EP | 3 059 236 A1 | 8/2016 |
| FR | 2 387 229 A1 | 11/1978 |
| FR | 2 436 786 A1 | 4/1980 |
| FR | 2 627 493 A1 | 8/1989 |
| FR | 2 645 861 A1 | 10/1990 |
| FR | 2 849 474 A3 | 7/2004 |
| FR | 2 859 474 A1 | 3/2005 |
| FR | 2 859 475 A1 | 3/2005 |
| GB | 585362 A | 2/1947 |
| GB | 2087387 A | 5/1982 |
| IN | 554/CHE/2003 | 4/2005 |
| JP | S52-72821 A | 6/1977 |
| JP | S56-051454 A | 5/1981 |
| JP | H09-508642 A | 9/1997 |
| JP | 2005-507365 A | 3/2005 |
| JP | 2006-504646 A | 2/2006 |
| JP | 2006-519846 A | 8/2006 |
| JP | 2008-519814 A | 6/2008 |
| JP | 2009-174368 A | 8/2009 |
| JP | 6378802 B2 | 8/2018 |
| WO | 95/21613 A1 | 8/1995 |
| WO | 00/59875 A2 | 10/2000 |
| WO | 2002/074726 A2 | 9/2002 |
| WO | 02/083643 A1 | 10/2002 |
| WO | 03/000660 A1 | 1/2003 |
| WO | 2003/037866 A1 | 5/2003 |
| WO | 2004/007461 A1 | 1/2004 |
| WO | 2004/078731 A1 | 9/2004 |
| WO | 2004/080463 A1 | 9/2004 |
| WO | 2005/023255 A2 | 3/2005 |
| WO | 2005/051302 A2 | 6/2005 |
| WO | 2005/112930 A1 | 12/2005 |
| WO | 2006/051311 A1 | 5/2006 |
| WO | 2006/060318 A2 | 6/2006 |
| WO | 2006/081444 A2 | 8/2006 |
| WO | 2007/000876 A1 | 1/2007 |
| WO | 2007/042899 A2 | 4/2007 |
| WO | 2007/103162 A2 | 9/2007 |
| WO | 2007/147217 A1 | 12/2007 |
| WO | 2008/003864 A1 | 1/2008 |
| WO | 2008/008234 A1 | 1/2008 |
| WO | 2008/089459 A1 | 7/2008 |
| WO | 2008/101935 A2 | 8/2008 |
| WO | 2008/115870 A2 | 9/2008 |
| WO | 2008/118468 A1 | 10/2008 |
| WO | 2008/143440 A1 | 11/2008 |
| WO | 2009/021696 A1 | 2/2009 |
| WO | 2009/023844 A2 | 2/2009 |
| WO | 2009/029617 A1 | 3/2009 |
| WO | 2009/085234 A2 | 7/2009 |
| WO | 2009/087238 A2 | 7/2009 |
| WO | 2009/132273 A2 | 10/2009 |
| WO | 2010/107965 A1 | 9/2010 |
| WO | 2010/127208 A1 | 11/2010 |
| WO | 2010/129451 A1 | 11/2010 |
| WO | 2010/143168 A2 | 12/2010 |
| WO | 2010/143169 A2 | 12/2010 |
| WO | 2010/143170 A2 | 12/2010 |
| WO | 2010/151755 A2 | 12/2010 |
| WO | 2011/057003 A2 | 5/2011 |
| WO | 2012/080953 A1 | 6/2012 |
| WO | 2014/055944 A1 | 4/2014 |
| WO | 2014/111892 A1 | 7/2014 |
| WO | 2015/001518 A1 | 1/2015 |
| WO | 2015/131019 A1 | 9/2015 |
| WO | 2016/009065 A2 | 1/2016 |
| WO | 2016/009066 A1 | 1/2016 |
| WO | 2016/135052 A1 | 9/2016 |
| WO | 2016/135055 A1 | 9/2016 |
| WO | 2017/158201 A1 | 9/2017 |

OTHER PUBLICATIONS

Zeng, et al., "Epigenetic regulation of miR-124 by Hepatitis C Virus core protein promotes migration and invasion of Intrahepatic cholangiocarcinoma cells by targeting SMYD3", FEBS Letters, vol. 586, No. 19, pp. 3271-3278, 2012.

Chebli et al. "The Anti-HIV Candidate Abx464 Dampens Intestinal Inflammation by Trigerring IL-22 Production in Activated Macrophages." Scientific Reports, vol. 7, No. 4860, pp. 1-11. 2017.

"Abivax sets its course on colitis and Crohn's." Pharmaphorum, pp. 1-3. Sep. 4, 2018.

Oct. 26, 2021 Office Action issued in U.S. Appl. No. 17/113,369.

U.S. Appl. No. 16/787,471, filed Feb. 11, 2020 in the name of Tazi et al.

U.S. Appl. No. 14/761,674, filed Jul. 17, 2015 in the name of Tazi et al.

U.S. Appl. No. 17/113,369, filed Dec. 7, 2020 in the name of Tazi et al.

Altuvia, et al., "Clustering and conservation patterns of human microRNAs", Nucleic Acids Research, 2005, vol. 33, No. 8, pp. 2697-2706, 2005.

Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.

Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.

Baklanov et al., "Photocyclization of (o-haloaryl)hetarylamines," Zhurnal Organicheskoi Khimii, 1991, vol. 27, No. 3, pp. 638-649.

Balkau et al., "Syntheis of Ellipticine Intermediates: 6-Amino-, 6-hydroxy-, and 6-Methoxy-5,8-Dimethylisoquinoline," Australian. J. Chem., 1969, vol. 22, pp. 2489-2492.

Bartel, et al., "MicroRNAs: Target Recognition and Regulatory Functions", Cell, vol. 136, No. 2, pp. 215-233, 2009.

Baskerville, et al., "Microarray profiling of microRNAs reveals frequent coexpression with neighboring miRNAs and host genes", RNA, vol. 11, No. 3, pp. 241-247, 2005.

(56) References Cited

OTHER PUBLICATIONS

Bisset et. al., "Combined effect of zidovudine (ZDV), lamivudine (3TC) and abacavir (ABC) antiretoviral therapy in suppressing in vitro FIV replication," Antiviral Research, 2002, Elsevier, vol. 53 pp. 35-45.
Black, "Mechanisms of Alternative Pre-Messenger RNA Splicing," Annu. Rev. Biochem., 2003, vol. 72, pp. 291-336.
Boganyi et al., "Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.
Brune et al., "Progeria: A New Kind of Laminopathy—Clinical and Molecular Update of the Hutchinson-Gilford Syndrome," 1st European Symposium, 2003.
Buchmann et al., "The Preparation and Reactivity of 4-hydroxy-7-chloroquinaldine," Journal fuer Praktische Chemie, 1962, vol. 17, pp. 135-146.
Bustin, "Absolute quantification of mRNA using real-time reverse transcription polymerase chain reaction assays", Journal of Molecular Endocrinology, vol. 25, pp. 169-193, 2000.
CAPLUS Record for Loriga et al., "Part 7." (Retrieved Nov. 2013).
CAPLUS Record for Loriga et al., "Part 8." (Retrieved Nov. 2013).
Cartegni et al., "Correction of Disease-associated Exon Skipping by Synthetic Exon-specific Activators," Nature Structural Biology, 2003, vol. 10, No. 2, pp. 120-125.
Cartegni et al., "Listening to Silence and Understanding Nonsense: Exonic Mutations that Affect Splicing," Nature Reviews—Genetics, Apr. 2002, vol. 3, pp. 285-298.
Carter et al., "Quinoxalines and related compounds-X-1", Tetrahedron, 34(7), p. 981-988, 1978.
CAS (Chemical Abstracts Service) Registry No. 1011408-51-7, American Chemical Society, added on STN on Apr. 1, 2008, 1 page.
CAS (Chemical Abstracts Service) Registry No. 92873-44-4, American Chemical Society, added on STN on Dec. 7, 1984, 1 page.
CAS (Chemical Abstracts Service) Registry No. 94541-69-2, American Chemical Society, added on STN on Feb. 3, 1985, 1 page.
CAS Registry No. 10562-04-6 added on STN on Nov. 16, 1984.
CAS Registry No. 138386-77-3 added on STN on Jan. 17, 1992.
CAS Registry No. 204851-25-2 added on STN on Apr. 30, 1998.
CAS Registry No. 208661-32-9 added on STN on Jul. 19, 1998.
CAS Registry No. 215589-34-7 added on STN on Dec. 15, 1998.
CAS Registry No. 294668-01-2 added on STN on Oct. 11, 2000.
CAS Registry No. 313266-85-2 added on STN on Jan. 9, 2001.
CAS Registry No. 324526-73-0 added on STN on Feb. 27, 2001.
CAS Registry No. 342653-87-6 added on STN on Jun. 20, 2001.
CAS Registry No. 449780-94-3 added on STN on Sep. 12, 2002.
CAS Registry No. 449780-95-4 added on STN on Sep. 12, 2002.
CAS Registry No. 5468-85-9 added on STN on Nov. 16, 1984.
CAS Registry No. 70682-97-2 added on STN on Nov. 16, 1984.
CAS Registry No. 1004363-48-7 added on STN on Feb. 19, 2008.
CAS Registry No. 1011408-51-7 added on STN on Apr. 1, 2008.
CAS Registry No. 1135230-99-7 added on STN on Apr. 16, 2009.
CAS Registry No. 330663-16-6 added on STN on Apr. 10, 2001.
CAS Registry No. 374598-11-5 added on STN on Dec. 10, 2001.
CAS Registry No. 438481-24-4 added on STN on Jul. 12, 2002.
CAS Registry No. 933238-11-0 added on STN on Apr. 29, 2007.
Connor et al., "Vpr is Required for Efficient Replication of Human Immunodeficiency Virus type-1 in Mononuclear Phagocytes," Virology, 1995, vol. 206, pp. 935-944.
Cottet et al., "Recommendable Routes to Trifluoromethyl-Substituted Pyridine-and Quinolinecarboxylic Acids," Eur. J. Org. Chem., 2003, pp. 1559-1568.
De Sandre-Giovannoli et al. "Lamin a Truncation in Hutchinson-Gilford Progeria". Science, vol. 300, p. 2055, 2003.
De Sandre-Giovannoli et al., "Altered Splicing in Prelamin A-associated Premature Aging Phenotypes," Progress In Molecular and Subcellular Biology, 2006, pp. 199-232.
Desai et al., "2-Methyl-4-quinoline-hydrazide Derivatives as Antitubercular/Antibacterial Agents—Part I," Asian Journal of Chemistry, vol. 10, No. 2, (1998), pp. 370-372.
Desai et al., "Some Quinoline, Quinazoline and Pyrazine Derivatives as Antitubercular-Antibacterial Agents," Asian Journal of Chemistry, vol. 10, No. 4 (1998), pp. 993-994.
Deuerleine, "Dipryridyl-, diquinolyl-, and Pyridylquinolylamines," Journal fuer Praktische Chemie (Liepzig), 1923, vol. 106, pp. 53-65.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Sep. 23, 2022 Office Action Issued In U.S. Appl. No. 17/113,369.
Sep. 28, 2022 Office Action Issued in U.S. Appl. No. 16/994,954.
Dignam et al., "Eukaryotic Gene Transcription with Purified Components," Methods in Enzymology, 1983, vol. 101, pp. 582-598.
Dobson, J. et al., "Attempts to find new antimalarials. XXVII. Derivatives of various benzacridines and pyridoacridines", Journal of the Chemical Society, pp. 123-126, Jan. 1948.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Edwards et al., "Orf-I amd Orf-II-Encoded Proteins in HTLV-1 Infection and Persistence", Viruses, 2011, MDPI, vol. 3, pp. 861-885.
El-Sayed et al. "Synthesis of Some Novel Quinoline-3-Carboxylic Acids and Pyrimidoquinoline Derivatives as Potential Antimicrobial Agents". Archiv der Pharmize, vol. 335, No. 9, pp. 403-410, 2002.
Etukala et al., "A Short and Convenient Synthesis and Evaluation of the Antiinfective Properties of Indoloquinoline Alkaloids: 10H-Indolo[3,2-b]quinoline and 7H-Indolo[2,3-c]quinolines," Journal of Heterocyclic Chemistry, No. 45, Mar. 2008, pp. 507-511.
Ewing et al., "Analysis of Expressed Sequence Tags Indicates 35,000 Human Genes," Nature Genetics, 2000, vol. 25, pp. 232-234.
F. J. Leinweber, "Possible Physiological Roles of Carboxylic Ester Hydrolases," Drug Metabolism Reviews, vol. 18, No. 4, pp. 379-439, 1987.
File Registry on STN, 101350-67-8, entered on Apr. 5, 1986.
File Registry on STN, 195876-33-6/RN, entered on Oct. 23, 1997.
File Registry on STN, 408510-56-5, entered on Apr. 29, 2002.
File Registry on STN, 55360-88-8, entered on Nov. 16, 1984.
File Registry on STN, 67412-46-8, entered on Nov. 16, 1984.
File Registry on Stn, 70125-24-5/RN, entered on Nov. 16, 1984.
File Registry on STN, 92873-44-4, entered on Dec. 7, 1984.
File Registry on STN, 94541-69-2, entered on Feb. 3, 1985.
File Registry on STN, 97978-62-6, entered on Sep. 16, 1985.
Fong et al., "A Protein Farnesyltransferase Inhibitor Ameliorates Disease in a Mouse Model of Progeria," Science, 2006, vol. 311, pp. 1621-1623.
Fors et al., "An Efficient Process for Pd-Catalyzed C—N Cross-Coupling Reactions of Aryl Iodides: Insight Into Controlling Factors," J. Am. Chem. Soc., 2009, 131, 5766-5768.
G. Bhattancharjee et al. "Synthesis of physiologically important quinoxaline derivatives using conventional method and microwave irradiation." Indian Journal of Chemical Technology, Council of Scientific & Industrial Research, vol. 15, No. 1, Jan. 2008, pp. 72-74.
Gordon et al., "Hutchinson-Gilford Progeria Syndrome," NCBI Bookshelf, 2003, accessed Http://www.ncbi.nlm.gov/books/NBK1121/ on Jan. 26, 2016,21 pages.
Graveley, "Sorting out the Complexity of SR Protein Functions," RNA, 2000, vol. 6, pp. 1197-1211.

(56) References Cited

OTHER PUBLICATIONS

Gritsenko et al., "Synthesis in Phenothiazines. XXXIX. Dimethylpyridophenothiazines," Khimiya Geterotsiklicheskikh Soedinenii, 1975, vol. 1, pp. 50-54.

Grout et al., "Polyazabenzo[a]pyrenes," Journal of the Chemical Society [Section] C: Organic, 1968, vol. 21, pp. 2689-2693.

Guo, et al., "Haplotype Distribution and Evolutionary Pattern of miR-17 and miR-124 Families Based on Population Analysis", PLoS One, vol. 4, Issue 11, 2009.

Hernandez-Lopez et al., "Alternative splicing in human tumour viruses: a therapeutic target?" Biochemical Journal, 2012, Biochemical Society, vol. 445, pp. 145-156.

Hofmann et al., "Htra2-ß1 Stimulates an Exonic Splicing Enhancer and can Restore Full-length SMN Expression to Survival Motor Neuron 2 (SMN2)," PNAS, 2000, vol. 97, No. 17, pp. 9618-9623.

Hostyn et al. "Synthesis of ?-Carbolines Starting from 2,3-Dichloropyridines and Substituted Anilines." Advanced Synthesis & Catalysis, Wiley, vol. 350, Oct. 2008, pp. 2653-2660.

Houzet, et al., "MicroRNAs and human retroviruses," Biochimica et Biophysica Acta, 1809(11-12), pp. 686-693, 2011.

J. Tazi et al., "Alternative Splicing and Disease," Biochimica et Biophysica Acta, 1792 (2009), 14-26.

J. Zugazagoitia et al. "Current Challenges in Cancer Treatment." Clinical Therapeutics, vol. 38, No. 7, May 2016, pp. 1551-1566.

Johnson et al., "Genome-Wide Survey of Human Alternative Pre-mRNA Splicing with Exon Junction Microarrays," Science, vol. 302, pp. 2141-2144, 2003.

Jonckers et al. "Selective Palladium-Catalyzed Aminations of Dicholoropyridines," Tetrahedron, 2001, vol. 57, pp. 7027-7034.

Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.

Katoh et al. "Isolation of the intermediates and improved synthesis of pyrido[1',2':1,2]imidazo[4, 5b]pyrazines and-quinoxalines", Heterocycles, 1992, 34(10), p. 1965-1972.

Khalifa. "Hutchinson-Gilford Progeria Syndrome: Report of a Libyan Family and Evidence of Autosomal Recessive Inheritance". Clinical Genetics, vol. 35, pp. 125-132, 1989.

Kim, et al., "Processing of intronic microRNAs", EMBO Journal, vol. 26, No. 3, pp. 775-783, 2007.

Klinck, et al., "Multiple Alternative Splicing Markers for Ovarian Cancer", Cancer Research, vol. 68, No. 3, pp. 657-663 , 2008.

Kondratenko et al. "Bactericidal Activity of Some Derivatives of N-Heteroaromatic Compounds". Mikrobiologichnii Zhurnal, 1934-1977, vol. 40, No. 3, pp. 368-370 (abstract only), 1978.

Labourier et al. "Recognition of Exonic Splicing Enhancer Sequences by the *Drosophila* Splicing Repressor RSF1". Nucleic Acids Research, vol. 27, No. 11, pp. 2377-2386, 1999.

Lai, et al., "Micro RNAs are complementary to 3' UTR sequence motifs that mediate negative post-transcriptional regulation", Nature Genetics, vol. 30, No. 4, pp. 363-364, 2002.

Lee, et al., "MicroRNA maturation: stepwise processing and subcellular localization", EMBO Journal, vol. 21, No. 17, pp. 4663-4670, 2002.

Lin Min et al., "Nonsense-mediated mRNA decay and tumors," Journal of International Pathology and Clinical Medicine, vol. 26, No. 4, pp. 291-294.

Lindow, et al., "Principles and Limitations of Computational MicroRNA Gene and Target Finding", DNA and Cell Biology, vol. 26, No. 5, pp. 339-351, 2007.

Liu et al. "Partial Correction of Endogenous F508 CFTR in Human Cystic Fibrosis Airway Epithelia by Spliceosome-Mediated RNA Trans-Splicing". Nature Biotechnology, vol. 20, pp. 47-52, 2002.

Liu, et al., "The evolution and functional diversification of animal microRNA genes", Cell Research, vol. 18, No. 10, pp. 985-996, 2008.

Wang, et al., "Quantitation of mRNA by the polymerase chain reaction", Proc. Natl. Acad. Sci., vol. 86, pp. 9717-9721, 1989.

Witwer, et al., "Relationships of PBMC microRNA expression, plasma viral load, and CD4+ T-cell count in HIV-1-infected elite suppressors and viremic patients", Retrovirology, vol. 9, No. 1, 2012.

Wong, et al., "Real-time PCR for mRNA quantitation", BioTechniques, vol. 39, No. 1, pp. 75-85, 2005.

Mar. 10, 2023 Office Action issued in U.S. Appl. No. 17/416,856.

Aberg, J. A. "Aging, Inflammation, and HIV Infection". Topics in Antiviral Medicine; vol. 20; Issue 3; pp. 101-105; 2012.

Gavegnano, C. et al. "Ruxolitinib and Tofacitinib are Potent and Selective Inhibitors of HIV-1 Replication and Virus Reactivation In Vitro". Antimicrobial Agents and Chemotherapy; vol. 58; No. 4; pp. 1977-1986; 2014.

Sep. 25, 2023 Office Action issued in U.S. Appl. No. 17/416,856.

Alsaidi H et al., "Convenient Synthesis of Heteroaryl Phenyl Ethers from Chloropyridines and Chloroquinolines Using Phase-Transfer Catalysis", Synthesis, Georg Thieme Verlag, Stuttgart, DE, No. 11, (1980), pp. 921-924.

Eugene D. Ponomarev et al., "MicroRNA-124 Promotes Microglia Quiescence and Suppresses EAE by Deactivating Macrophages via the C/EBP-?-PU.1 Pathway", Nature Medicine, vol. 17, No. 1, Jan. 2011, pp. 64-71.

Feb. 6, 2018 Office Action issued in U.S. Appl. No. 15/326,755.

Jan. 22, 2016 Search Report issued in International Patent Application No. PCT/EP2015/066458.

Jan. 3, 2019 Office Action issued in U.S. Appl. No. 15/326,755.

Jun. 8, 2018 Office Action issued in U.S. Appl. No. 15/326,755.

Yang Sun et al., "MicroRNA-124 Mediates the Cholinergic Anti-Flammatory Action Throught Inhibiting the Production of Pro-Inflammatory Cytokines", Cell Research, vol. 23, No. 11, (2013), pp. 1270-1283.

J. Wei et al., "miR-124 Inhibits STAT3 Signaling to Enhance T Cell-Mediated Immune Clearance of Glioma," Cancer Research, vol. 73, No. 13, Jul. 1, 2013, pp. 3913-3926.

Nov. 14, 2019 English Translation of Office Action issue in Russian Patent Application No. 2017101407/04.

Saari, R., et al. "Microwave-assisted synthesis of quinoline, isoquinoline, quinoxaline and quinazoline derivatives as CB2 receptor agonists." Bioorganic & Medicinal Chemistry. Elservier. vol. 19, Jan. 2011, pp. 939-950.

Belikov, V.G. Pharmaceutical Chemistry. Moscow. MEDpress-inform, 2007, pp. 27-29.

Litvickji, P. F. Pathophysiology. Moscow. GEOTAR-MED, vol. 1, 2003, pp. 142-144, 192-200.

Database CAS Registry of RN 338750-07-5, RN 338749-97-6, and RN 338417-00-8 (2001).

Kher Samir et al., "Microwave Mediated Dearylation of 2-Aryloxy-5-Nitropyridine," Research Journal of Chemical Sciences, vol. 1, No. 6, Sep. 2011, pp. 84-87.

O.A. Yanborisova et al., "Synthesis and antiinflammatory activity of 2-arylaminocinchoninic acids and amides of 1,2-dihydro-2-oxocinchoninic acid," Pharmaceutical Chemistry Journal, vol. 29, No. 6, Jun. 1995, pp. 32-33.

O.A. Yanborisova et al., "Derivatives of 2-aminocinchoninic acids: synthesis and antiinflammatory activity," Pharmaceutical Chemistry Journal, vol. 2B, No. 1, 1994, pp. 29-31.

Huang-Kai Peng et al., "Synthesis and anti-HCV activity evaluation of anilinoquinoline derivatives," Bioorganic & Medicinal Chemistry Letters, vol. 22, 2012, pp. 1107-1110.

Scott D. Kuduk et al., "Amiloride derived inhibitors of acid sensing ion channel-3 (ASIC3)," Bioorganic & Medicinal Chemistry Letters, vol. 19, 2009, pp. 2514-2518.

Yang Sun et al., "MicroRNA-124 mediates the cholinergic anti-inflammatory action through inhibiting the production of pro-inflammatory cytokines," Cell Research, vol. 23, No. 11, Nov. 2013, pp. 1270-1283.

Georgios Koukos et al., "MicroRNA-124 Regulates STAT3 Expression and Is Down-regulated in Colon Tissues of Pediatric Patients With Ulcerative Colitis," Gastroenterology, vol. 145, No. 4, Oct. 2013, pp. 842-852.

(56) References Cited

OTHER PUBLICATIONS

Ruth M. Murray et al., "The Nitration of Some Aryloxy-2- and -4-methylquinoline. Syntheses of Substanes having possible Antimalarial Action," Journal of the Chemical Society, 1934, pp. 856-860.
Database CAS Registry of RN 338749-91-0. Retreived Feb. 2020.
Database CAS Registry of RN 1556532-05-8. Retreived Feb. 2020.
Database CAS Registry of RN 1457614-02-6. Retreived Feb. 2020.
Database CAS Registry of RN 448932-63-6. Retreived Feb. 2020.
Database CAS Registry of RN 478032-29-0. Retreived Feb. 2020.
Apr. 27, 2020 Office Action issued in U.S. Appl. No. 16/554,748.
Database CAS Registry of RN 926207-30-9. Retreived 2020.
Database CAS Registry of RN 1019446-43-5. Retreived 2020.
Database CAS Registry of RN 1548036-82-3. Retreived 2020.
Database CAS Registry of RN 1094714-12-1. Retreived 2020.
Database CAS Registry of RN 298216-45-2. Retreived 2020.
Fengmao An et al. "MiR-124 acts as a target for Alzheimer's disease by regulating BACE1." Oncotarget, No. 69, vol. 8, 2017, pp. 114065-114071.
Zhibo Yang et al. "MicroRNA-124 alleviates chronic skin inflammation in atopic eczema via suppressing innate immune responses in keratinocytes." Cellular Immunology, vol. 319, 2017, pp. 53-60.
Derrick D. Eichele et al. "Dextran sodium sulfate colitis murine model: An indispensable tool for advancing our understanding of inflammatory bowel diseases pathogenesis." World Journal of Gastroenterology, No. 33, vol. 23, Sep. 2017, pp. 6016-6029.
Marc Fakhoury et al. "Inflammatory bowel disease: clinical aspects and treatments." Journal of Inflammation Research, Dovepress, Jun. 2014, pp. 113-120.
Zhen Qin et al. "miR-124, a potential therapeutic target in colorectal cancer." OncoTargets and Therapy, Dovepress, Dec. 2019, pp. 749-751.
S.-L. Tang et al. "MiR-124 regulates osteoblast differentiation through GSK-3? in ankylosing spondylitis." European Review for Medical and Pharmacological Sciences, vol. 22, 2018, pp. 6616-6624.
Fangfang Jin et al. "Serum microRNA Profiles Serve as Novel Biomarkers for Autoimmune Diseases." Frontiers in Immunology, vol. 9, Art. 2381, Oct. 2018, pp. 1-9.
Antonella Amoruso et al. "Immune and central nervous system-related miRNAs expression profiling in monocytes of multiple sclerosis patients." Nautre: Scientific Reports, vol. 10, Art. 6125, 2020, url: https://doi.org/10.1038/s41598-020-63282-3.
Longping Yao et al. "MicroRNA-124 regulates the expression of MEKK3 in the inflammatory pathogenesis of Parkinson's disease." Journal of Neuroinflammation, vol. 15, No. 13, 2016, pp. 1-19.
Audrey Vautrin et al. "Both anti-inflammatory and antiviral properties of novel drug candidate ABX464 are mediated by modulation of RNA splicing." Nautre: Scientific Reports, vol. 9, Art. 792, 2019, url: https://doi.org/10.1038/s41598-018-37813-y.
Yueyuan Xiao et al. "miR124-3p/FGFR2 axis inhibits human keratinocyte proliferation and migration and improve the Inflammatory microenvironment in psoriasis." Molecular Immunology, vol. 122, 2020, pp. 89-98.
Xueying Li et al. "Long non-coding RNA NEAT1 overexpression associates with increased exacerbation risk, severity, and inflammation, as well as decreased lung function through the interaction with microRNA-124 in asthma." Journal of Clinical Laboratory Analysis, vol. 34, No. 1, 2019, 9 pages.
Tatyana Veremeyko et al. "IL-4/IL-13-Dependent and Independent Expression of miR-124 and Its Contribution to M2 Phenotype of Monocytic Cells in Normal Conditions and during Allergic Inflammation." Plos One, vol. 8, No. 12, 2013, 13 pages.
O.A. Yanborisova et al., "Synthesis and study of antiinflammatory and nd analgesic activity of 2-arylaminocinchoninic acid hydrazides and ß-(1-carboxyethylidene)hydrazides." Pharmaceutical Chemistry Journal, vol. 31, No. 6, Jun. 1997, pp. 309-310.
A. Simacek et al. "Preparation and Reactivity of 3-Amino-2,4-dichloroquinoline." Synlett, vol. 23, 2012, pp. 2205-2208.
Rolak, Clin Med Res, Jan. 2003, vol. 1 (1), 57-60. (Year: 2003).
A.K. El-Damasy et al. "Novel 5-substituted-2-anilinoquinolines with 3-(morpholino or 4-methylpiperazin-1-yl)propoxy moiety as broad spectrum antiproliferative agents: Synthesis, cell based assays and kinase screening." Bioorganic & Medicinal Chemistry Letters, vol. 26, No. 14, May 2016, pp. 3307-3312.
A.L. Wilson et al. "New Trends in Anti-Cancer Therapy: Combining Conventional Chemotherapeutics with Novel Immunomodulators." Current Medicinal Chemistry, vol. 25, No. 36, Dec. 2018, pp. 4758-4784.

* cited by examiner

IN VITRO OR EX VIVO METHODS FOR SCREENING A QUINOLINE DERIVATIVE

This is a Divisional of application Ser. No. 16/994,954 filed Aug. 17, 2020, which is a Divisional of application Ser. No. 16/554,748 filed Aug. 29, 2019, which is a Divisional of application Ser. No. 15/326,755 filed Jan. 17, 2017, which is a National Stage Application of PCT/EP2015/066458 filed Jul. 17, 2015, which claims the benefit of EP 14306164.6 filed on Jul. 17, 2014. The entire disclosures of the prior applications are hereby incorporated by reference herein their entireties.

FIELD OF THE INVENTION

The invention relates to the identification of novel quinoline derivatives which are efficient for treating and/or preventing inflammatory diseases, as well as novel therapeutic uses of quinoline derivative towards inflammatory diseases.

The invention also relates to the field of biomarkers in connection with such inflammatory diseases.

BACKGROUND OF THE INVENTION

Inflammation is a protective response by the immune system to tissue damage and infection. However, the inflammatory response, in some circumstances, can damage the body. In the acute phase, inflammation is characterized by pain, heat, redness, swelling and loss of function. There are a wide range of inflammatory conditions which affect millions of people worldwide.

Indeed, inflammatory diseases include a wide range of conditions including, inflammatory disease associated with an autoimmune disease, a central nervous system (CNS) inflammatory disease, a joint inflammation disease, an inflammatory digestive tract disease, and inflammatory skin. Among them, Inflammatory Bowel Disease, Rheumatoid Arthritis and Multiple Sclerosis are of particular interest.

Inflammatory Bowel Disease (IBD) is a complex multifactorial disease (Perse and Cerar, 2012). It commonly refers to ulcerative colitis (UC) and Crohn's disease (CD), the two chronic conditions that involve inflammation of the intestine. IBD is common in developed countries, with up to 1 in 200 of individuals of Northern European region affected by these diseases. Patients with IBD present several clinically challenging problems for physicians. DSS-induced colitis is associated with the upregulation of different proinflammatory cytokines including TNFalpha and IFNgamma. Recently, miR-124 has been shown to be de-regulated specifically in pediatric patients with active UC, leading to increased levels of transducer and activator of transcription 3 (STAT3) expression and the transcriptional activation of its downstream targets among which proinflammatory cytokines (Koukos et al.; Gastroenterology; 145(4):842-52: 2013). However, in spite of recent advances, there remains a need for a safe, well-tolerated therapy with a rapid onset, and increased capacity for maintaining long-term remission.

Rheumatoid arthritis (RA) is the most frequent autoimmune disease with a prevalence of about 0.3 to 1% of the population worldwide and often associated with reduced mobility, increased social dependency and work disability. RA is a systemic inflammatory disease affecting the joint lining tissue called synovium. The rheumatoid synovial tissue is characterized by hyper-proliferation of fibroblast-like synoviocytes (FLS) in the intimal lining layer and infiltration of the sublining by macrophages, T and B cells, and other inflammatory cells that promote inflammation and destruction of bone and cartilage. The intra-articular and systemic expression of pro-inflammatory cytokines, in particular tumor necrosis factor alpha (TNFα), interleukin-1 (IL-1) and -6 (IL-6), which are primarily produced by synovial macrophages, plays a crucial role in the pathogenesis of RA, e.g. by contributing to the hyper-proliferation of RA FLS. RA patients are in general treated with a group of small molecular drugs called disease modifying antirheumatic drugs (DMARDs). DMARDs suppress the body's overactive immune and/or inflammatory systems in some way, thereby slowing down disease progression. RA patients not responding to DMARDs are treated with biological agents such as Tumor Necrosis Factor (TNF) antagonists. However, even though TNF antagonists are effective in about two-thirds of the patients, the responding patients frequently become non-responsive within five years. Therefore, alternative treatments are required. Notably, there is a particular interest for novel therapeutic approaches designed for RA patients at early stages, before the disease becomes chronic.

Multiple sclerosis (MS) is an inflammatory disease autoimmune, demyelinating disease of the central nervous system that destroys myelin, oligodendrocytes, and axons. MS is characterized by multiple foci of inflammation and infiltration of macrophages and encephalitogenic T cells in the central nervous system. Microglia are found throughout the central nervous system and participate in the onset and progression of CNS inflammatory responses. Microglia, when activated, are highly damaging to CNS function through their production of neurotoxins, inflammatory cells (Inflammatory Protein-10, Macrophage Inflammatory Protein-1, Macrophage Inflammatory Protein-2, C—C Chemokine Ligand 19, Monocyte Chemoattractant Protein-1, Monocyte Chemoattractant Protein-2) and immune cells that produce antibodies. Microglia direct inflammatory responses that can result in the brain and spinal cord being infiltrated with immune cells against foreign invaders as well as T-cells that destroy myelin proteins. Peripheral macrophages appear in the CNS during inflammation and these cells have a highly activated phenotype, efficiently stimulate expansion of encephalitogenic T cells, and are thought to contribute to neuronal tissue destruction.

MicroRNAs (miRNA), the most comprehensive noncoding group, are a class of about 22 nt noncoding RNAs that inhibit gene expression through binding to the UnTranslated Region (UTR) of target mRNA transcripts (Lai et al., Nature Genetics, vol. 30, no. 4, pp. 363-364, 2002; Bartel et al., Cell, vol. 136, no. 2, pp. 215-233, 2009). miRNA genes represent about 1-2% of the known eukaryotic genomes. Predictions suggest that each miRNA can target more than 200 transcripts and that a single mRNA can be regulated by multiple miRNAs (LINDOW, DNA Cell Biol., vol. 26(5), p. 339-351, 2007). miRNAs are generated from endogenous hairpin-shaped transcripts and act by base pairing with target mRNAs, which leads to mRNA cleavage or translational repression, depending on the degree of base-pairing. Two processing events lead to mature miRNA formation: first, the nascent miRNA transcripts (pri-miRNA) are processed into 70 nucleotides precursors (pre-miRNA) which are exported from the nucleus and are cleaved in the cytoplasm to generate short (about 22 nucleotides long) mature miRNAs (LEE, EMBO J., vol. 21, p; 4663-4670, 2002). miRNAs can be located inter- or intragenically. When intergenic, their expression is coordinated with other miRNAs as a cluster (Altuvia et al., Nucleic Acids Research, vol. 33, no. 8, pp. 2697-2706, 2005, Ozsolak et al., Genes and Development, vol. 22, no. 22, pp. 3172-3183, 2008). When intragenic, namely, positioned within a protein-coding gene (almost exclusively in introns), they are often expressed from the same strand as their host-gene (Liu et al., Cell Research, vol. 18, no. 10, pp. 985-996, 2008, Kim et al., EMBO Journal, vol. 26, no. 3, pp. 775-783, 2007) and at correlated levels (Baskerville el al., RNA, vol. 11, no. 3, pp. 241-247, 2005).

It has now been shown that overexpression of a miRNA, namely miR-124, deactivates inflammatory macrophages and converts them into microglia-like cells. miR-124 is believed to inhibit macrophage activation by targeting CEBPα, a transcription factor responsible for the differentiation of myeloid lineage cells. Intravenous injection of liposomes containing miR-124 markedly suppresses clinical EAE symptoms and inhibits the infiltration of encephalitogenic T cells and inflammatory macrophages into the CNS.

Indeed, Ponomarev et al ("microRNA-124 promotes microglia quiescence and suppresses EAE by deactivating macrophages via the C/EBP-α-PU.1 pathway"; Nature Medicine (2011); 17:1: 64-71) suggests that miR-124 could play a role as a key regulator of microglia quiescence and as a modulator of monocyte and macrophage activation. Based on an Experimental Autoimmune Encephalomyelitis (EAE) model, this study suggests that the miR-124 expression pattern is modulated (either up-regulated or down-regulated depending on the cell type) in mice with EAE.

WO2010/151755 also teaches the administration of miR-124 for treating a central nervous system (CNS) inflammatory disease.

Sun et al. ("microRNA-124 mediates the cholinergic anti-inflammatory action through inhibiting the production of pro-inflammatory cytokines"; Cell Research (2013); 23:1270-1283) also teaches that miR-124 could mediate a cholinergic anti-inflammatory action through targeting of STAT3 and TACE.

On the other hand, novel compounds, also referred herein as "quinoline derivatives" have been identified, but for distinct indications.

For reference, a Quinoline is a heterocyclic aromatic organic compound of formula:

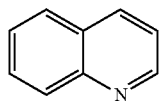

Thus, "quinoline derivatives" include substituted Quinolines, such as mono-, or polysubstituted Quinolines.

WO2010/143170 teaches the use of compounds for treating conditions associated with premature aging.

WO2010/143169 and WO2012/080953 teach the use of compounds for treating AIDS.

WO2010/143168 teaches the use of compounds for treating a selection of cancers. Those compounds have been shown to be able to correct defects of alternative splicing.

SUMMARY OF THE INVENTION

It has now been found that compounds as defined in formula (I) hereinafter are useful in the treatment and/or prevention of inflammatory diseases.

The present invention therefore relates to compounds of formula (I), as defined below, for use in the treatment and/or prevention of an inflammatory disease.

In particular, the invention relates to compounds of formula (I), as defined below, for use in the treatment and/or prevention of inflammation, and/or inflammation which may occur along with such inflammatory diseases.

The invention also relates to an in vitro or ex vivo use of at least one miRNA, said at least one miRNA being miR-124, as a biomarker for screening, a quinoline derivative, and in particular a compound of formula (I), presumed effective in treating and/or preventing an inflammatory disease.

The invention further relates to a compound of formula (Id) or (Ie) as defined hereinafter as such.

The invention further relates to a pharmaceutical composition comprising at least one compound of formula (Id) or (Ie).

It also relates to a compound as such, selected in a list consisting of:
(8) 8-chloro-5-(3-(piperidin-1-yl)propoxy)-N-(4-(trifluoromethyl)pyridin-2-yl)quinolin-2-amine
(9) 8-chloro-$N^4$-(3-(piperidin-1-yl)propyl)-$N^2$-(4-(trifluoromethyl)pyridin-2-yl)quinoline-2,4-diamine
(10) 8-chloro-N-methyl-N-(4-(trifluoromethyl)pyridin-2-yl)quinolin-2-amine
(11) 8-chloro-$N^4$-(2-morpholinoethyl)-$N^2$-(4-(trifluoromethyl)pyridin-2-yl)quinoline-2,4-diamine
(13) 4,8-dichloro-N-(4-(trifluoromethyl)pyridin-2-yl)quinolin-2-amine
(14) 8-chloro-N-(3-morpholinopropyl)-N-(4-(trifluoromethyl)pyridin-2-yl)quinolin-2-amine
(15) 8-chloro-6-(2-morpholinoethoxy)-N-(3-morpholinopropyl)-N-(4-(trifluoromethyl)pyridin-2-yl)quinolin-2-amine
(16) 8-chloro-5-(2-morpholinoethoxy)-N-(3-morpholinopropyl)-N-(4-(trifluoromethyl)pyridin-2-yl)quinolin-2-amine
(17) 8-chloro-6-(2-(4-methylpiperazin-1-yl)ethoxy)-N-(4-(trifluoromethyl)pyridin-2-yl)quinolin-2-amine
(18) 8-chloro-6-(2-(piperidin-1-yl)ethoxy)-N-(4-(trifluoromethyl)pyridin-2-yl)quinolin-2-amine
(19) 8-chloro-6-(3-(piperidin-1-yl)propoxy)-N-(4-(trifluoromethyl)pyridin-2-yl)quinolin-2-amine
(20) 8-chloro-N-(3-fluoro-4-(trifluoromethyl)pyridin-2-yl)quinolin-2-amine
(21) N-(5-bromo-4-(trifluoromethyl)pyridin-2-yl)-8-chloroquinolin-2-amine
(22) $N^2$-(8-chloroquinolin-2-yl)-N-(3-(4-methylpiperazin-1-yl)propyl)-4-(trifluoromethyl)pyridine-2,5-diamine
(28) 8-chloro-N-methyl-N-(4-(trifluoromethoxy)phenyl)quinolin-2-amine
(29) 8-chloro-5-(3-(piperidin-1-yl)propoxy)-N-(4-(trifluoromethoxy)phenyl)quinolin-2-amine
(30) 8-chloro-N-(3-(piperidin-1-yl)propyl)-N-(4-(trifluoromethoxy)phenyl)quinolin-2-amine
(31) 8-chloro-N-(2-morpholinoethyl)-N-(4-(trifluoromethoxy)phenyl)quinolin-2-amine
(32) 8-chloro-N-(2-(pyrrolidin-1-yl)ethyl)-N-(4-(trifluoromethoxy)phenyl)quinolin-2-amine
(33) 8-chloro-N-(4-morpholinobutyl)-N-(4-(trifluoromethoxy)phenyl)quinolin-2-amine
(34) 8-chloro-$N^4$-(3-(piperidin-1-yl)propyl)-$N^2$-(4-(trifluoromethoxy)phenyl)quinoline-2,4-diamine
(35) 4,8-dichloro-N-(4-(trifluoromethoxy)phenyl)quinolin-2-amine
(36) 8-chloro-5-(2-morpholinoethoxy)-N-(4-(trifluoromethoxy)phenyl)quinolin-2-amine
(37) $N^1$-(4,8-dichloroquinolin-2-yl)-4-(trifluoromethoxy)benzene-1,2-diamine

(38) 4,8-dichloro-N-(2-morpholinoethyl)-N-(4-(trifluoromethoxy)phenyl)quinolin-2-amine
(39) 8-chloro-6-(2-morpholinoethoxy)-N-(4-(trifluoromethoxy)phenyl)quinolin-2-amine
(40) 8-chloro-$N^2$-(2-morpholinoethyl)-$N^4$-(3-(piperidin-1-yl)propyl)-$N^2$-(4-(trifluoromethoxy)phenyl)quinoline-2,4-diamine
(41) 8-chloro-N-(2-morpholinoethyl)-N-(2-nitro-4-(trifluoromethoxy)phenyl)quinolin-2-amine
(42) $N^1$-(8-chloroquinolin-2-yl)-$N^1$-(2-morpholinoethyl)-4-(trifluoromethoxy)benzene-1,2-diamine
(43) 8-chloro-5-(2-morpholinoethoxy)-N-(2-morpholinoethyl)-N-(4-(trifluoromethoxy)phenyl)quinolin-2-amine
(44) $N^1$-(8-chloro-5-(2-morpholinoethoxy)quinolin-2-yl)-4-(trifluoromethoxy)benzene-1,2-diamine
(46) 8-chloro-2-((4-(trifluoromethyl)pyridin-2-yl)oxy)quinoline
(47) 4-(2-((8-chloro-2-((4-(trifluoromethyl)pyridin-2-yl)oxy)quinolin-6-yl)oxy)ethyl)morpholine
(48) 8-chloro-2-(4-(trifluoromethoxy)phenoxy)quinoline
(49) 4-(2-((8-chloro-2-(4-(trifluoromethoxy)phenoxy)quinolin-6-yl)oxy)ethyl)morpholine
(50) 4-(2-((8-chloro-2-(4-(trifluoromethoxy)phenoxy)quinolin-5-yl)oxy)ethyl)morpholine
(51) phosphoric acid mono-[8-chloro-2-(4-trifluoromethyl-pyridin-2-ylamino)-quinolin-6-yl] ester
(52) phosphoric acid mono-[2-(8-chloro-quinolin-2-ylamino)-5-trifluoromethoxy-phenyl] ester
(53) phosphoric acid mono-[8-chloro-2-(4-trifluoromethoxy-phenylamino)-quinolin-6-yl] ester
and their pharmaceutically acceptable salts, and more particularly selected from compounds (8), (9); (10); (11); (30); (46); (47); (48); (49) and (50) as defined above or one of its pharmaceutical salts.

It also relates to a pharmaceutical composition comprising at least one compound of formula (Id) or (Ie), or one of compounds (8), (9), (10), (11), (13), (14), (15), (16), (17), (18), (19), (20), (21), (22), (28), (29), (30), (31), (32), (33), (34), (35), (36), (37), (38), (39), (40), (41), (42), (43), (44), (46), (47), (48), (49), (50), (51), (52) and (53), and more particularly one of compounds (8), (9), (10), (11), (30), (46), (47), (48), (49) and (50) as defined above.

The invention further relates to an in vitro or ex vivo method for increasing the expression of miR-124 in an eukaryotic cell, comprising at least a step of:
a) providing an eukaryotic cell,
b) bringing into contact said cell with a quinoline derivative, and in particular a compound of formula (I).

The invention further relates to an in vitro or ex vivo method for screening a derivative compound, and in particular a compound of formula (I), presumed effective in treating and/or preventing an inflammatory disease, comprising at least a step of:
a) providing an eukaryotic cell,
b) bringing into contact said cell with a compound of formula (I),
c) measuring an expression of miR-124 in said cell, and
d) selecting the candidate presumed effective in treating and/or preventing an inflammatory disease when the level of expression of miR-124 measured in step c) is increased relatively to a reference value.

DETAILED DESCRIPTION OF THE INVENTION

Figure 1:
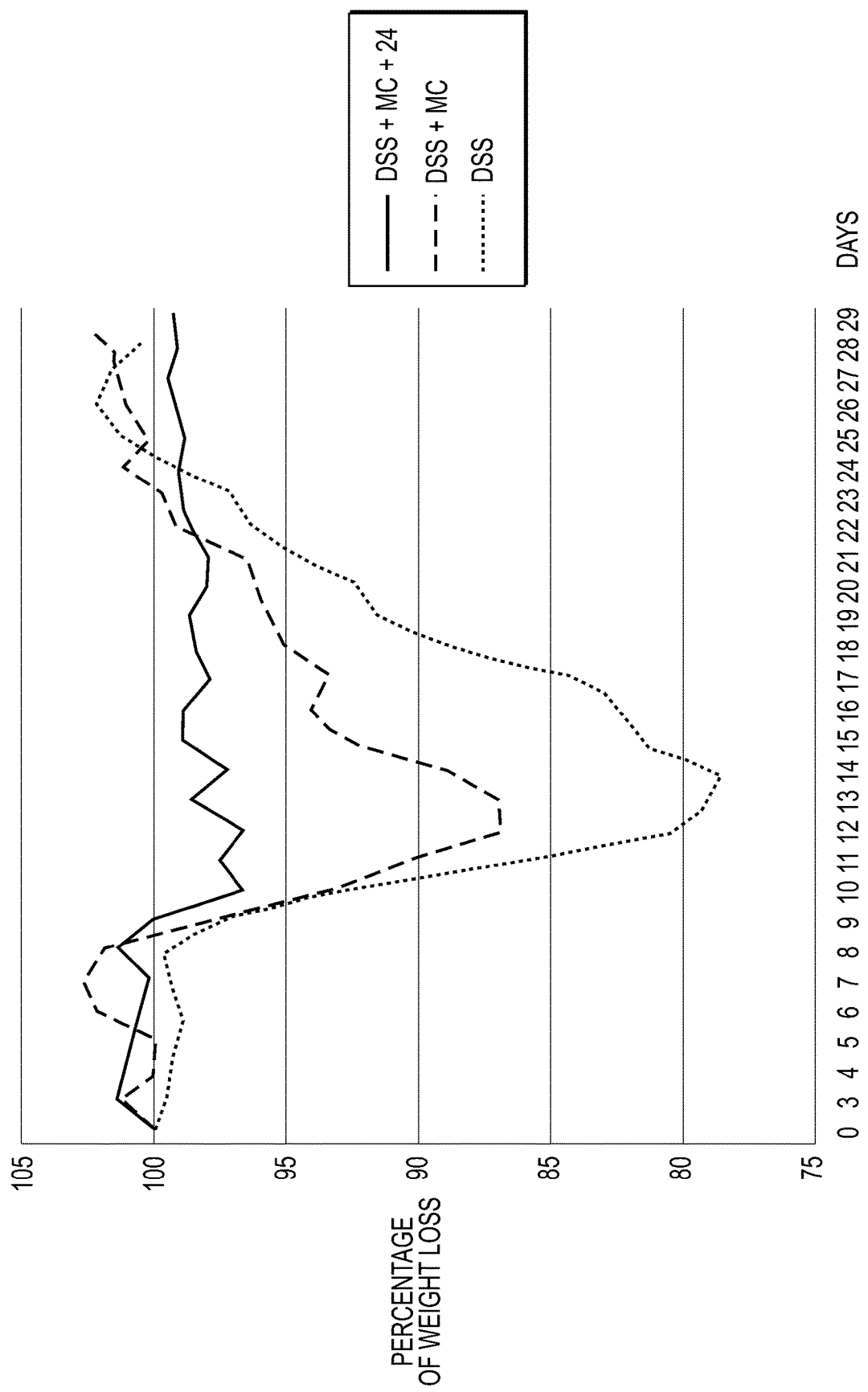
FIG. 1: Dextran sulphate sodium (DSS-) induced colitis model 1—Variation of the percentage of weight loss over time (days), on a DSS-mouse model, in the presence of quinoline derivative compound (24) as defined hereinafter. The percentage of weight loss (%) is indicated in the y-axis. DSS treatment occurs on days 3 to (x-axis). Gavage with a quinoline derivative in methylcellulose (MC), or MC only, occurs between days 3 to 29.

There is a need for identifying novel compounds for use in the treatment and/or prevention of an inflammatory disease.

There is also a need for a novel biomarker for assessing the activity of candidate drugs, such as quinoline derivatives towards inflammatory diseases.

The present invention has for purpose to meet these needs.
Quinoline Derivatives According to a first aspect, a subject-matter of the present invention relates to the use of a compound of formula (I):

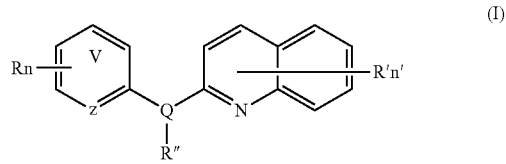

wherein:
Z is C or N,
V is C or N,

means an aromatic ring wherein V is C or N and when V is N, V is in ortho, meta or para of Z, i.e. forms respectively a pyridine, a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a (C$_3$-C$_6$) cycloalkyl group, a —NO$_2$ group, a —NR$_1$R$_2$ group, a (C$_1$-C$_4$)alkoxy group, a phenoxy group, a —NR$_1$—SO$_2$—NR$_1$R$_2$ group, a —NR$_1$—SO$_2$—R$_1$ group, a —NR$_1$—C(=O)—R$_1$ group, a —NR$_1$—C(=O)—NR$_1$R$_2$ group, a —SO$_2$—NR$_1$R$_2$ group, a —SO$_3$H group, a —O—SO$_2$—OR$_3$ group, a —O—P(=O)—(OR$_3$)(OR$_4$) group, a —O—CH$_2$—COOR$_3$ group and a (C$_1$-C$_3$)alkyl group, said alkyl being optionally monosubstituted by a hydroxyl group, Q is N or O, provided that R" does not exist when Q is O, R$_1$ and R$_2$ are independently a hydrogen atom or a (C$_1$-C$_3$)alkyl group, R$_3$ and R$_4$ independently represent a hydrogen atom, Li$^+$, Na$^+$, K$^+$, N$^+$(Ra)$_4$ or a benzyl group, n is 1, 2 or 3, n' is 1, 2 or 3, R' independently represent a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group, a —O—P(=O)—(OR$_3$)(OR$_4$) group and a —CN group, and can further be a group chosen among:

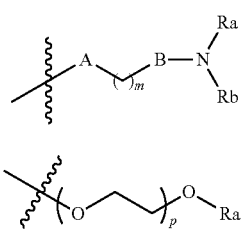

A is a covalent bond, an oxygen atom or NH,
B is a covalent bond or NH,
m is 1, 2, 3, 4 or 5,
p is 1, 2 or 3,
Ra and Rb independently represent a hydrogen atom, a (C$_1$-C$_5$)alkyl group or a (C$_3$-C$_6$)cycloalkyl group,
Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa),
R" is a hydrogen atom, a (C$_1$-C$_4$)alkyl group or is a group (IIa) as defined above,
or anyone of its pharmaceutically acceptable salt,
in the treatment and/or prevention of an inflammatory disease.

According to a preferred embodiment, Q is N.
According to another preferred embodiment, n is 1 or 2.
According to another preferred embodiment, n' is 1 or 2.

According to another preferred embodiment, R" is a hydrogen atom, a (C$_1$-C$_4$)alkyl group or a group

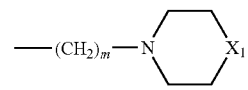

wherein m is 2 or 3 and X$_1$ is O, CH$_2$ or N—CH$_3$.

According to another preferred embodiment, R independently represent a hydrogen atom, a methyl group, a methoxy group, a trifluoromethyl group, a trifluoromethoxy group, an amino group, a halogen atom and a —O—P(=O)—(OR$_3$)(OR$_4$) group and more particularly a fluorine or chlorine atom, a trifluoromethoxy group and an amino group.

According to another preferred embodiment, R' independently represent a hydrogen atom, a halogen atom and more particularly a fluorine or chlorine atom, an amino group, a methyl group, a —O—P(=O)—(OR$_3$)(OR$_4$) group or a group

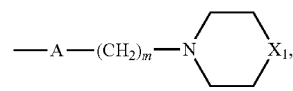

wherein A is O or NH, m is 2 or 3 and X$_1$ is O, CH$_2$ or N—CH$_3$, provided that when R' is such a group, n' is 1 or 2, and when n' is 2, the other R' group is different from said group.

According to one aspect of said preferred embodiment, R' alternatively independently represent a hydrogen atom, a halogen atom and more particularly a fluorine or chlorine atom, a methyl group or a group,

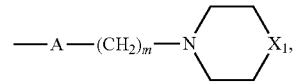

wherein A is O or NH, m is 2 and X$_1$ is O, CH$_2$ or N—CH$_3$, provided that when R' is such a group, n' is 1 or 2, and when n' is 2, the other R' group is different from said group.

All the preceding and following particular embodiments may of course be combined together and form part of the invention.

Compounds of formula (I) include compounds of formula (Ia), (Ib), (Ic), (Id) and (Ie), as defined hereabove.

According to a Particular Embodiment, Another Subject-Matter of the Present Invention is the Use of a Compound of Formula (Ia)

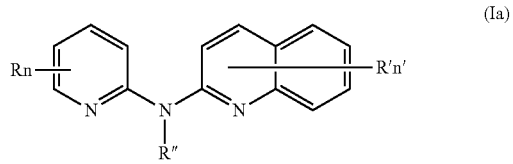

wherein R, R', R", n and n' are as defined above,
in the treatment and/or prevention of an inflammatory disease.

According to one aspect of said preferred embodiment, n is 1 or 2.

According to one aspect of said preferred embodiment, n' is 1 or 2.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$ fluoroalkoxy group, a $-NR_1R_2$ group, a $(C_1\text{-}C_4)$alkoxy group and a $(C_1\text{-}C_3)$alkyl group.

According to one aspect of said preferred embodiment, R' independently represent a hydrogen atom, a halogen atom or a group chosen among a $(C_1\text{-}C_3)$alkyl group, a hydroxyl group, a $-O-P(=O)-(OR_3)(OR_4)$ group, a $-NR_1R_2$ group, or a group

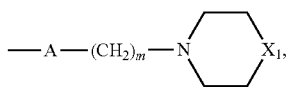

wherein A is O or NH, m is 2 or 3 and $X_1$ is O, $CH_2$ or $N-CH_3$, provided that when R' is such a group, n' is 1 or 2 and when n' is 2, the other R' group is different from said group.

According to one aspect of said referred embodiment, R" is a hydrogen atom, a $(C_1\text{-}C_4)$alkyl group or a group

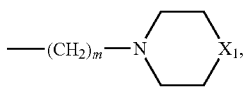

wherein m is 2 or 3 and $X_1$ is O, $CH_2$ or $N-CH_3$, and preferably R" is a hydrogen atom or a methyl group.

According to a Particular Embodiment, Another Subject-Matter of the Present Invention is the Use of a Compound of Formula (Ib)

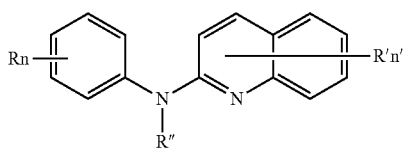

wherein R, R', R", n and n' are as defined above,
in the treatment and/or prevention of an inflammatory disease.

According to one aspect of said preferred embodiment, n is 1 or 2.

According to one aspect of said preferred embodiment, n' is 1, 2 or 3.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$fluoroalkoxy group, a $-NR_1R_2$ group, a $(C_1\text{-}C_4)$alkoxy group, a $-O-P(=O)(OR_3)(OR_4)$ group and a $(C_1\text{-}C_3)$alkyl group.

According to one aspect of said preferred embodiment, R' independently represent a hydrogen atom, a halogen atom or a group chosen among a $(C_1\text{-}C_3)$alkyl group, a hydroxyl group, a $-O-P(=O)-(OR_3)(OR_4)$ group, a $-NR_1R_2$ group, or a group

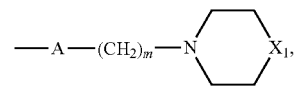

wherein A is O or NH, m is 2 or 3 and $X_1$ is O, $CH_2$ or $N-CH_3$, provided that when R' is such a group, n' is 1 or 2, and when n' is 2, with the other R' group is different from said group.

According to one aspect of said preferred embodiment, R' alternatively independently represent a hydrogen atom, a halogen atom or a group chosen among a $(C_1\text{-}C_3)$alkyl group, a hydroxyl group or a $-NR_1R_2$ group.

According to one aspect of said preferred embodiment, R" is a hydrogen atom, a $(C_1\text{-}C_4)$alkyl group or a group

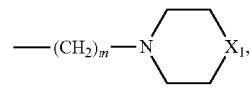

wherein m is 2 or 3 and $X_1$ is O, $CH_2$ or $N-CH_3$, and preferably R" is a hydrogen atom or a methyl group.

According to a Particular Embodiment, Another Subject-Matter of the Present Invention is the Use of a Compound of Formula (Ic)

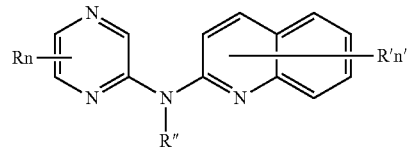

wherein R, R', R", n and n' are as defined above,
in the treatment and/or prevention of an inflammatory disease.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1\text{-}C_3)$ fluoroalkyl group, a $(C_1\text{-}C_3)$ fluoroalkoxy group, a $-NR_1R_2$ group, a $(C_1\text{-}C_4)$ alkoxy group and a $(C_1\text{-}C_3)$ alkyl group.

According to one aspect of said preferred embodiment, R alternatively independently represent a hydrogen atom or a halogen atom.

According to one aspect of said preferred embodiment, R' independently represent a hydrogen atom, a halogen atom or a group chosen among a $(C_1\text{-}C_3)$ alkyl group, a hydroxyl group, a $-NR_1R_2$ group, or a group

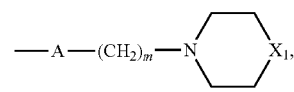

wherein A is O or NH, m is 2 or 3 and $X_1$ is O, $CH_2$ or $N-CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a $(C_1\text{-}C_4)$alkyl group or a group

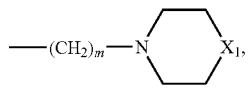

wherein m is 2 or 3 and $X_1$ is O, $CH_2$ or N—$CH_3$, and preferably R" is a hydrogen atom or a methyl group.

According to a Particular Embodiment, Another Subject-Matter of the Present Invention is the Use of a Compound of Formula (Id)

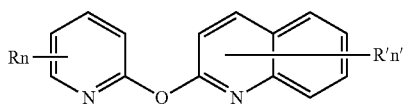

wherein R, R', n and n' are as defined above,
in the treatment and/or prevention of an inflammatory disease.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$fluoroalkoxy group, a —$NR_1R_2$ group, a $(C_1\text{-}C_4)$alkoxy group and a $(C_1\text{-}C_3)$alkyl group.

According to one aspect of said preferred embodiment, R alternatively independently represent a hydrogen atom, a $(C_1\text{-}C_3)$fluoroalkyl group, a $(C_1\text{-}C_3)$fluoroalkoxy group or a halogen atom.

According to one aspect of said preferred embodiment, R' independently represent a hydrogen atom, a halogen atom or a group chosen among a $(C_1\text{-}C_3)$alkyl group, a hydroxyl group, a —$NR_1R_2$ group, or a group

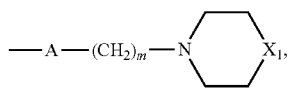

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a $(C_1\text{-}C_4)$alkyl group or a group

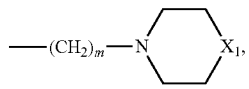

wherein m is 2 or 3 and $X_1$ is O, $CH_2$ or N—$CH_3$, and preferably R" is a hydrogen atom or a methyl group.

According to a Particular Embodiment, Another Subject-Matter of the Present Invention is the Use of a Compound of Formula (Ie)

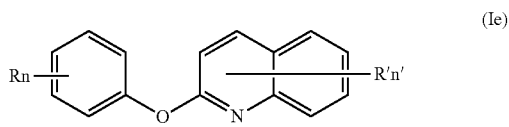

wherein R, R', n and n' are as defined above,
in the treatment and/or prevention of an inflammatory disease.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$fluoroalkoxy group, a —$NR_1R_2$ group, a $(C_1\text{-}C_4)$alkoxy group and a $(C_1\text{-}C_3)$alkyl group.

According to one aspect of said preferred embodiment, R alternatively independently represent a hydrogen atom, a $(C_1\text{-}C_3)$fluoroalkyl group, a $(C_1\text{-}C_3)$fluoroalkoxy group or a halogen atom.

According to one aspect of said preferred embodiment, R' independently represent a hydrogen atom, a halogen atom or a group chosen among a $(C_1\text{-}C_3)$alkyl group, a hydroxyl group, a —$NR_1R_2$ group, or a group

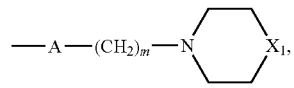

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a $(C_1\text{-}C_4)$alkyl group or a group

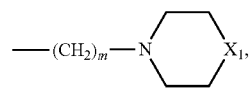

wherein m is 2 or 3 and $X_1$ is O, $CH_2$ or N—$CH_3$, and preferably R" is a hydrogen atom or a methyl group.

According to another particular embodiment, compounds (Id) and (Ie) as defined above, as such, also form part of the present invention.

According to a preferred embodiment of the present invention, some compounds of formula (I) are new, form part of the present invention and are chosen among (with the number to be found in table 1 hereinafter):

(8) 8-chloro-5-(3-(piperidin-1-yl)propoxy)-N-(4-(trifluoromethyl)pyridin-2-yl)quinolin-2-amine
(9) 8-chloro-N-(3-(piperidin-1-yl)propyl)-$N^2$-(4-(trifluoromethyl)pyridin-2-yl)quinoline-2,4-diamine
(10) 8-chloro-N-methyl-N-(4-(trifluoromethyl)pyridin-2-yl) quinolin-2-amine
(11) 8-chloro-N-(2-morpholinoethyl)-$N^2$-(4-(trifluoromethyl)pyridin-2-yl)quinoline-2,4-diamine
(13) 4,8-dichloro-N-(4-(trifluoromethyl)pyridin-2-yl)quinolin-2-amine
(14) 8-chloro-N-(3-morpholinopropyl)-N-(4-(trifluoromethyl)pyridin-2-yl)quinolin-2-amine
(15) 8-chloro-6-(2-morpholinoethoxy)-N-(3-morpholinopropyl)-N-(4-(trifluoromethyl)pyridin-2-yl)quinolin-2-amine
(16) 8-chloro-5-(2-morpholinoethoxy)-N-(3-morpholinopropyl)-N-(4-(trifluoromethyl)pyridin-2-yl)quinolin-2-amine
(17) 8-chloro-6-(2-(4-methylpiperazin-1-yl)ethoxy)-N-(4-(trifluoromethyl)pyridin-2-yl)quinolin-2-amine
(18) 8-chloro-6-(2-(piperidin-1-yl)ethoxy)-N-(4-(trifluoromethyl)pyridin-2-yl)quinolin-2-amine
(19) 8-chloro-6-(3-(piperidin-1-yl)propoxy)-N-(4-(trifluoromethyl)pyridin-2-yl)quinolin-2-amine
(20) 8-chloro-N-(3-fluoro-4-(trifluoromethyl)pyridin-2-yl) quinolin-2-amine
(21) N-(5-bromo-4-(trifluoromethyl)pyridin-2-yl)-8-chloroquinolin-2-amine
(22) $N^2$-(8-chloroquinolin-2-yl)-$N^5$-(3-(4-methylpiperazin-1-yl)propyl)-4-(trifluoromethyl)pyridine-2,5-diamine
(28) 8-chloro-N-methyl-N-(4-(trifluoromethoxy)phenyl) quinolin-2-amine
(29) 8-chloro-5-(3-(piperidin-1-yl)propoxy)-N-(4-(trifluoromethoxy)phenyl)quinolin-2-amine
(30) 8-chloro-N-(3-(piperidin-1-yl)propyl)-N-(4-(trifluoromethoxy)phenyl)quinolin-2-amine
(31) 8-chloro-N-(2-morpholinoethyl)-N-(4-(trifluoromethoxy)phenyl)quinolin-2-amine
(32) 8-chloro-N-(2-(pyrrolidin-1-yl)ethyl)-N-(4-(trifluoromethoxy)phenyl)quinolin-2-amine
(33) 8-chloro-N-(4-morpholinobutyl)-N-(4-(trifluoromethoxy)phenyl)quinolin-2-amine
(34) 8-chloro-$N^4$-(3-(piperidin-1-yl)propyl)-$N^2$-(4-(trifluoromethoxy)phenyl)quinoline-2,4-diamine
(35) 4,8-dichloro-N-(4-(trifluoromethoxy)phenyl)quinolin-2-amine
(36) 8-chloro-5-(2-morpholinoethoxy)-N-(4-(trifluoromethoxy)phenyl)quinolin-2-amine
(37) $N^1$-(4,8-dichloroquinolin-2-yl)-4-(trifluoromethoxy) benzene-1,2-diamine
(38) 4,8-dichloro-N-(2-morpholinoethyl)-N-(4-(trifluoromethoxy)phenyl)quinolin-2-amine
(39) 8-chloro-6-(2-morpholinoethoxy)-N-(4-(trifluoromethoxy)phenyl)quinolin-2-amine
(40) 8-chloro-$N^2$-(2-morpholinoethyl)-NM-(3-(piperidin-1-yl)propyl)-$N^2$-(4-(trifluoromethoxy)phenyl)quinoline-2,4-diamine
(41) 8-chloro-N-(2-morpholinoethyl)-N-(2-nitro-4-(trifluoromethoxy)phenyl)quinolin-2-amine
(42) $N^1$-(8-chloroquinolin-2-yl)-$N^1$-(2-morpholinoethyl)-4-(trifluoromethoxy)benzene-1,2-diamine
(43) 8-chloro-5-(2-morpholinoethoxy)-N-(2-morpholinoethyl)-N-(4-(trifluoromethoxy)phenyl)quinolin-2-amine
(44) $N^1$-(8-chloro-5-(2-morpholinoethoxy)quinolin-2-yl)-4-(trifluoromethoxy)benzene-1,2-diamine
(46) 8-chloro-2-((4-(trifluoromethyl)pyridin-2-yl)oxy)quinoline
(47) 4-(2-((8-chloro-2-((4-(trifluoromethyl)pyridin-2-yl) oxy)quinolin-6-yl)oxy)ethyl)morpholine
(48) 8-chloro-2-(4-(trifluoromethoxy)phenoxy)quinoline
(49) 4-(2-((8-chloro-2-(4-(trifluoromethoxy)phenoxy)quinolin-6-yl)oxy)ethyl)morpholine
(50) 4-(2-((8-chloro-2-(4-(trifluoromethoxy)phenoxy)quinolin-5-yl)oxy)ethyl)morpholine
(51) phosphoric acid mono-[8-chloro-2-(4-trifluoromethyl-pyridin-2-ylamino)-quinolin-6-yl] ester
(52) phosphoric acid mono-[2-(8-chloro-quinolin-2-ylamino)-5-trifluoromethoxy-phenyl] ester
(53) phosphoric acid mono-[8-chloro-2-(4-trifluoromethoxy-phenylamino)-quinolin-6-yl] ester
and their pharmaceutically acceptable salts.

For the purpose of the present invention, a compound of formula (I) includes any one of compounds of formula (Ia), (Ib), (Ic), (Id) and (Ie), as well as combinations thereof. Compounds of formula (I) include compounds (1) to (53), as defined in Table I, and combinations thereof.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates or hydrates and the invention includes all such solvates and hydrates.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

In the context of the present invention, the term:
"halogen" is understood to mean chlorine, fluorine, bromine, or iodine, and in particular denotes chlorine, fluorine or bromine,
"($C_1$-$C_5$)alkyl" as used herein respectively refers to $C_1$-$C_5$ normal, secondary or tertiary saturated hydrocarbon. Examples are, but are not limited to, methyl, ethyl, 1-propyl, 2-propyl, butyl, pentyl,
"($C_3$-$C_6$)cycloalkyl" as used herein respectively refers to cyclic saturated hydrocarbon. Examples are, but are not limited to cyclopropyl, cyclobutyl, cyclopentyl, cyclohexyl,
"($C_1$-$C_4$)alkoxy" as used herein respectively refers to O—($C_1$-$C_4$)alkyl moiety, wherein alkyl is as defined above. Examples are, but are not limited to, methoxy, ethoxy, 1-propoxy, 2-propoxy, butoxy,
"fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl,
"saturated 5- or 6-membered heterocycle" as used herein respectively refers to a saturated cycle comprising at least one heteroatom. Examples are, but are not limited to, morpholine, piperazine, thiomorpholine, piperidine, pyrrolidine, "patient" may extend to humans or mammals, such as cats or dogs.

The compounds of formula (I) which are suitable for the invention may be prepared as described in WO2010/143170, WO2010/143169, WO2012/080953 and WO2010/143168, and/or as described further here below.

More particularly, compounds of formula (I) wherein R' represents a group chosen among:

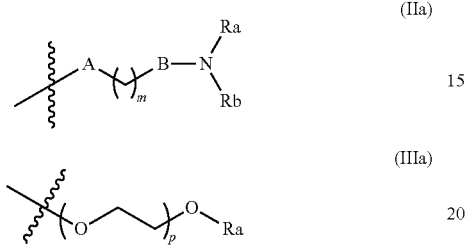

as defined above, may be prepared according to synthetic routes as described in WO2012/080953, more particularly when A is O.

When A is N, the following synthetic route may be implemented. A quinoline derivative of formula (VII) may be synthesized as a building block, before additional cross-coupling reactions.

In order to obtain said compound of formula (VII), the following sequence of reactions may be carried out as shown in Scheme 1 below.

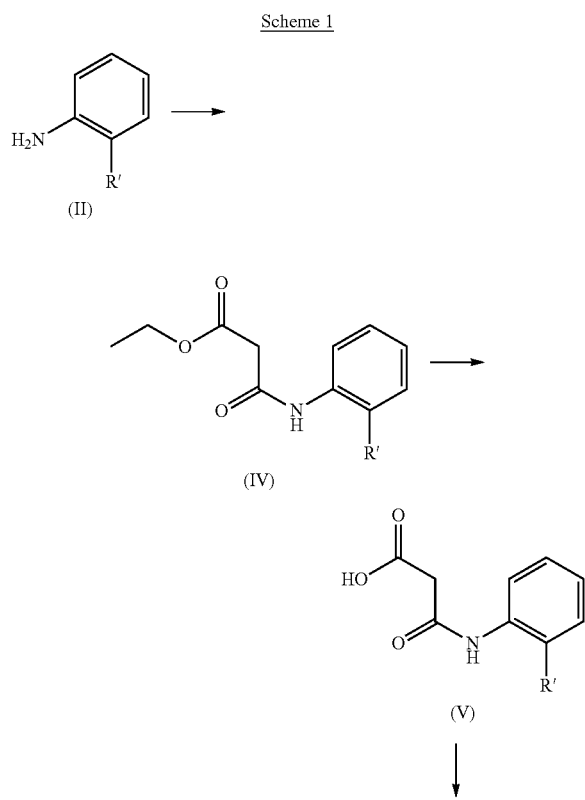

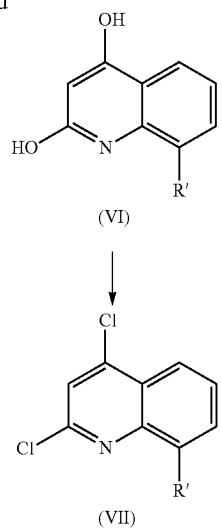

The compound of formula (II), wherein R' is different from H and is as defined above and may in particular be a Chlorine atom, can be placed in pyridine, the compound of formula (III) can then be added in a molar ratio ranging from 1 to 2, for example 1.5, with respect to the compound of formula (II). The reaction mixture can be stirred at a temperature ranging from 110 to 150° C., for example at 130° C., for a time ranging from 8 hours to 18 hours, for example 14 hours. Upon cooling to room temperature, the reaction mixture can be concentrated under reduced pressure and the resulting residue can be diluted with an organic solvent such as dichloromethane. The organic phase can then be washed with a saturated aqueous solution of an inorganic base such as $Na_2CO_3$, dried over $MgSO_4$, filtered and concentrated under reduced pressure to give a compound of formula (IV).

The compound of formula (IV) can be placed in a THF/water mixture, sodium hydroxide can then be added in a molar ratio ranging from 1 to 1.5, for example 1.2, with respect to the compound of formula (IV), and the reaction mixture can be stirred at room temperature for a time ranging from 8 hours to 18 hours, for example 14 hours. Concentrated hydrochloric acid can then be added until reaching pH 2 and the resulting solution can be extracted with an organic solvent such as ethyl acetate. The organic phase can then be dried over $MgSO_4$, filtered and concentrated under reduced pressure to give a compound of formula (V).

The compound of formula (V) can be placed in polyphosphoric acid, added in a molar ratio ranging from 5 to 15, for example 10, with respect to the compound of formula (V), and the reaction mixture can be stirred at a temperature ranging from 110 to 150° C., for example at 130° C., for a time ranging from 8 hours to 18 hours, for example 14 hours. Upon cooling to room temperature, an aqueous solution of sodium hydroxide with a molarity ranging from 1 to 5M, for example 2M, can slowly be added. The resulting precipitate can be filtered, rinsed with water and dried under reduced pressure in a desiccator to give a compound of formula (VI).

The compound of formula (VI) can be placed in $POCl_3$, added in a molar ratio ranging from 5 to 15, for example 10, with respect to the compound of formula (VI), and the reaction mixture can be stirred at a temperature ranging from 80 to 120° C., for example at 100° C., for a time ranging from 1 hour to 5 hours, for example 2 hours. Upon cooling to room temperature, water can slowly be added. The resulting precipitate can be filtered, rinsed with water and dried under reduced pressure in a desiccator to give a compound of formula (VII).

Said intermediate compound of formula (VII) may be used to form a compound of formula (I) by cross-coupling it with an aniline derivative, an aminopyridine derivative, a pyrimidine derivative, a hydroxypyridine derivative, a phenol derivative or a hydroxypyrimidine derivative, as described in WO2010/143170, WO2010/143169, WO2012/080953 and WO2010/143168 and/or as described further here below.

Chlorine in position 4 of the intermediate compound of formula (VII) may thereafter be substituted by an amine to form a quinoline derivative bearing a group of formula (IIa) with A=NH.

When Q=N and R" is different from H, the following routes, illustrated by schemes 2 and 3, may be implemented.

In order to obtain compounds of formula (IX), the following reaction may be carried out as shown in Scheme 2 below.

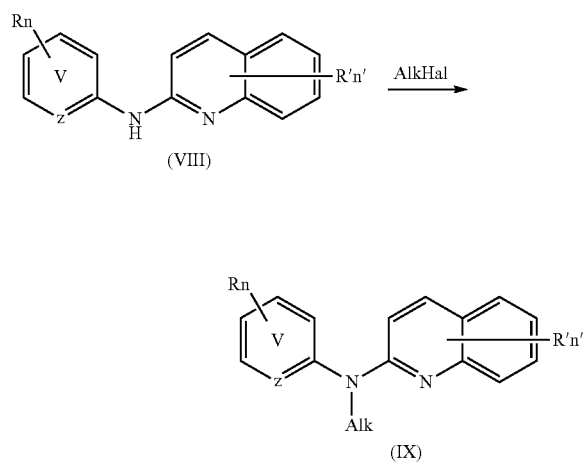

The compound of formula (VIII), wherein Z, V, n, n', R and R' are as defined above, can be placed in an anhydrous polar solvent such as anhydrous N,N-dimethylformamide in the presence of AklHal, wherein Alk represents a $(C_1$-$C_4)$ alkyle group and Hal represents a halogen atom, in a molar ratio ranging from 1 to 2, for example 1.1, and in the presence of an inorganic base such as potassium tert-butoxide in a molar ratio ranging from 1 to 2, for example 1.1, with respect to the compound of formula (VIII). The reaction mixture can be stirred at room temperature for a time ranging from 7 hours to 24 hours, for example 16 hours. The reaction mixture can be partitioned between water and an organic solvent such as ethyl acetate. The organic phases can then be gathered, washed with a saturated aqueous solution of brine, dried over MgSO$_4$, filtered and concentrated under reduced pressure to give a compound of formula (IX).

In order to obtain compounds of formula (XII), the following reaction may be carried out as shown in Scheme 3 below.

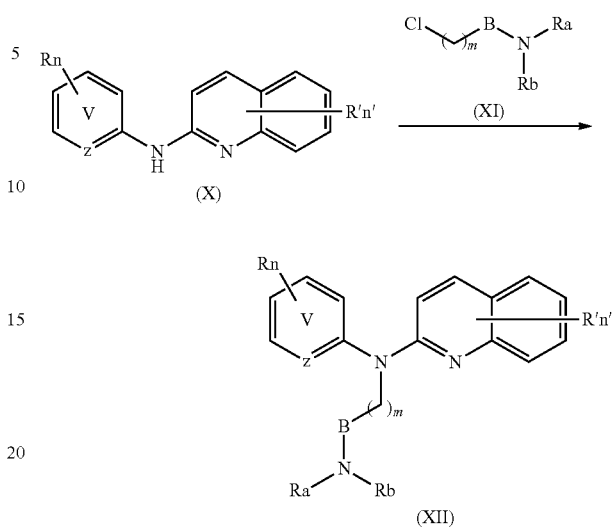

The compound of formula (X), wherein Z, V, n, n', R and R' are as defined above, can be placed in an anhydrous polar solvent such as anhydrous N,N-dimethylformamide in the presence of NaH in a molar ratio ranging from 2 to 5, for example 3, and the reaction mixture can be stirred at room temperature for a time ranging from 10 minutes to 50 minutes, for example 30 minutes. The compound of formula (XI), wherein m, B, Ra and Rb are as defined above, can then be placed, in a molar ratio ranging from 1 to 2, for example 1, in an anhydrous polar solvent such as anhydrous N,N-dimethylformamide in the presence of KI in a molar ratio ranging from 1 to 2, for example 1, and in the presence of an organic base such as Et$_3$N in a molar ratio ranging from 1 to 2, for example 1, with respect to the compound of formula (X), and the reaction mixture can be stirred at room temperature for a time ranging from 10 minutes to 50 minutes, for example 30 minutes, under an inert atmosphere of gas, for example argon. The activated compound (X) can then added to compound (XI) and the resulting reaction mixture can be stirred at a temperature ranging from 70 to 110° C., for example at 90° C., for a time ranging from 2 hours to 10 hours, for example 4 hours. Upon cooling to room temperature, the reaction mixture can be concentrated under reduced pressure and the resulting residue can be diluted with an organic solvent such as ethyl acetate. The organic phase can then be washed with a saturated aqueous solution of brine, dried over MgSO$_4$, filtered and concentrated under reduced pressure to give a compound of formula (XII).

When

bears a substitution being an amino group of formula (IIa), wherein A is NH, the following route may be implemented, as in Scheme 4.

Scheme 4

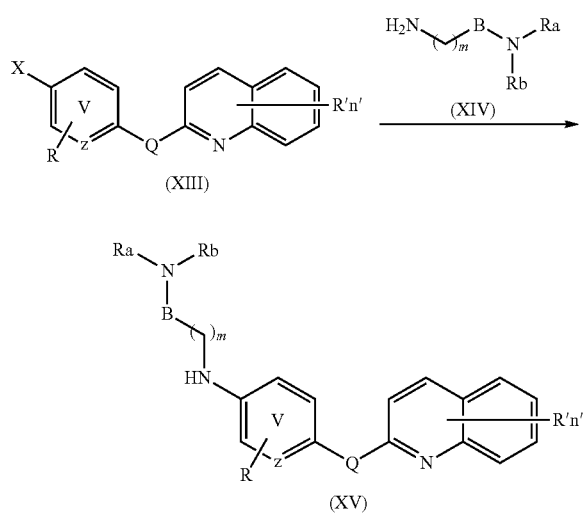

The compound of formula (XIII), wherein Z, V, n', R and R' are as defined above and X is a halogen atom such as Br, can be placed in a polar solvent mixture such as a dioxane/N,N-dimethylformamide mixture. A compound of formula (XIV), wherein B, $R_a$, and $R_b$ are as defined above, is then added in a molar ratio ranging from 1 to 2, for example 1.5, with respect to the compound of formula (XIII), in the presence of a non-nucleophilic organic base, such as sodium tert-butoxide or potassium tert-butoxide, in a molar ratio ranging from 2 to 5, for example 3, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 5 mol % to 40 mol % relative to the total amount of compound of formula (XIII), and in the presence of a catalyst, such as Pd(OAc)$_2$ or Pd$_2$(dba)$_3$ in an amount ranging from 2 mol % to mol % relative to the total amount of compound of formula (XIII). The reaction mixture can be heated in a microwave reactor at a temperature ranging from 90 to 150° C., for example at 120° C., for a time ranging from 30 minutes to 100 minutes, for example 70 minutes. The reaction mixture can be concentrated under reduced pressure and the residue can be diluted with an organic solvent such as ethyl acetate. The organic phase can be washed with water, decanted, dried over magnesium sulphate, filtered and concentrated under reduced pressure to give a compound of formula (XV).

The compounds of general formula (Id) as defined above can be prepared according to Scheme 5 below.

Scheme 5

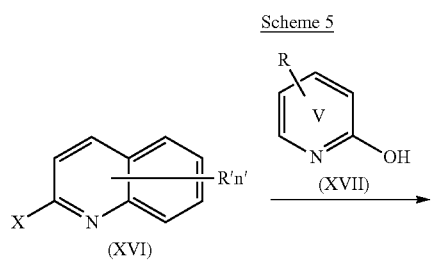

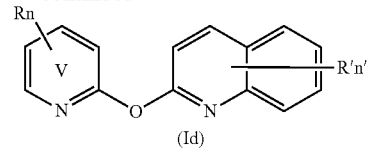

The compound of formula (XVI), wherein n' and R' are as defined above and X is a halogen atom such as Cl, can be placed in a polar solvent such as N,N-dimethylformamide in the presence of an inorganic base such as Cs$_2$CO$_3$ in a molar ratio ranging from 2 to 5, for example 3, and in the presence of CuI in a molar ratio ranging from 1 to 2, for example 1. The compound of formula (XVII), wherein R, V and n are as defined above, can then be added in a molar ratio ranging from 1 to 2, for example 1, with respect to the compound of formula (XVI). The reaction mixture can be heated in a microwave reactor at a temperature ranging from 130 to 170° C., for example at 150° C., for a time ranging from 30 minutes to 100 minutes, for example 50 minutes. Upon cooling to room temperature, water can be added to the reaction mixture, the undissolved solids can be filtered through celite and the resulting filtrate can be extracted with an organic solvent such as ethyl acetate. The organic phase can then be washed with water and a saturated aqueous solution of brine, dried over MgSO$_4$, filtered and concentrated under reduced pressure to give a compound of formula (Id).

The compounds of general formula (Ie) as defined above can be prepared according to Scheme 6 below.

Scheme 6

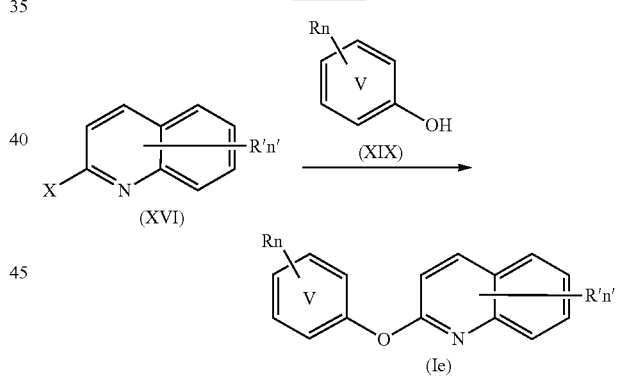

The compound of formula (XVI), wherein n' and R' are as defined above and X is a halogen atom such as Cl, can be placed in a polar solvent such as N,N-dimethylformamide in the presence of an inorganic base such as Cs$_2$CO$_3$ in a molar ratio ranging from 2 to 5, for example 3, and in the presence of CuI in a molar ratio ranging from 1 to 2, for example 1. The compound of formula (XIX), wherein R, V and n are as defined above, can then be added in a molar ratio ranging from 1 to 2, for example 1, with respect to the compound of formula (XVI). The reaction mixture can be heated in a microwave reactor at a temperature ranging from 130 to 170° C., for example at 150° C., for a time ranging from 30 minutes to 100 minutes, for example 50 minutes. Upon cooling to room temperature, water can be added to the reaction mixture, the undissolved solids can be filtered through celite and the resulting filtrate can be extracted with an organic solvent such as ethyl acetate. The organic phase can then be washed with water and a saturated aqueous solution of brine, dried over MgSO$_4$, filtered and concentrated under reduced pressure to give a compound of formula (Ie).

More particularly, compounds of formula (I) wherein R' represents a —O—P(=O)—(OR$_3$)(OR$_4$) group may be prepared starting from a compound of formula (XX) having a R' group being a OH group, through the following route:

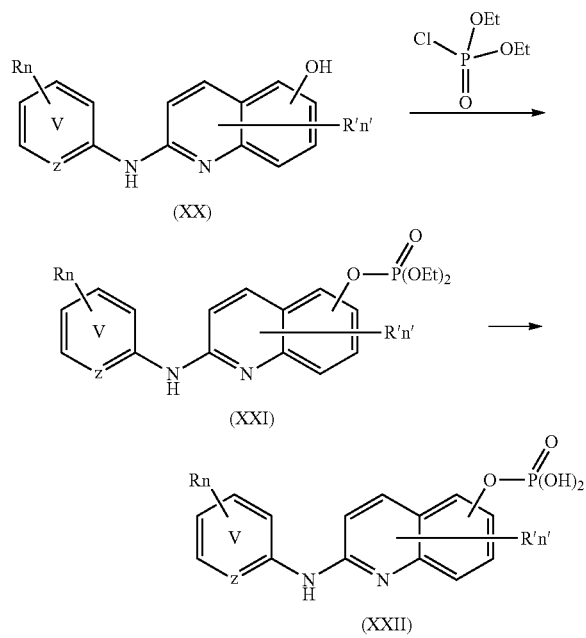

The compound of formula (XX), wherein Z, V, n, n', R and R' are as defined above, can be placed in an anhydrous chloroalkane solvent such as anhydrous dichloromethane, at 0° C. under an inert atmosphere of gas, for example argon, in the presence of diethylchlorophosphate in a molar ratio of 1, and in the presence of an organic base such as triethylamine in a molar ratio ranging from 1 to 2, for example 1.2, with respect to the compound of formula (XX). The reaction mixture can be stirred at room temperature for a time ranging from 7 hours to 24 hours, for example 14 hours. The reaction mixture can then be concentrated under reduced pressure and the resulting residue can be partitioned between an aqueous solution of hydrochloric acid with a molarity ranging from 1 to 2 M, for example 1M, and an organic solvent such as ethyl acetate. The organic phases can then be gathered, washed with a saturated aqueous solution of an inorganic base such as Na$_2$CO$_3$, dried over MgSO$_4$, filtered and concentrated under reduced pressure to give a compound of formula (XXI).

The compound of formula (XXI) can be placed in a polar aprotic solvent such as acetonitrile, in the presence of trimethylsilylbromide in a molar ratio ranging from 1 to 5, for example 4, with respect to the compound of formula (XXI). The reaction mixture can be stirred under microwave irradiation at a temperature ranging from 50 to 70° C., for example at 60° C., for a time ranging from 15 hours to 60 minutes, for example 30 minutes. Upon cooling to room temperature, a MeOH/water (95/5) mixture can slowly be added. The resulting precipitate can be filtered, rinsed with water and dried under reduced pressure in a desiccator to give a compound of formula (XXII).

The same procedure may be applied for obtaining compounds of formula (I) wherein R represents a —O—P(=O)—(OR$_3$)(OR$_4$) group, starting from a compound of formula (I) having a R group being a OH group.

Inflammatory Diseases

Thus, the invention also relates to a compound of formula (Ia), (Ib), (Ic), (Id) and (Ie), for use in the treatment and/or prevention of an inflammatory disease.

Surprisingly, the inventors were able to show that compounds of formula (I) led to a dramatic improvement of the signs associated with inflammatory diseases such as Inflammatory bowel disease (IBD) and Rheumatoid Arthritis (RA), based on two in vivo mouse models.

The inflammation modulating capacity of compounds of formula (I) has now been assessed in two established mouse models for two inflammatory diseases: Inflammatory bowel disease (IBD) and Rheumatoid Arthritis (RA). The Dextran Sulphate Sodium (DSS-) induced colitis mouse model has been used for studying Inflammatory Bowel Disease (see Perše & Cerar; "Dextran Sodium Sulphate Colitis Mouse Model: Traps and Tricks"; Journal of Biomedicine and Biotechnology (2012); 718617). The collagen-induced arthritis model has been used for studying Rheumatoid Arthritis, as shown in Brand et al. ("Collagen-induced arthritis"; Nature Protocols; (2007); 2(5):1269-75).

Indeed, the inventors have shown that the administration of a compound belonging to formula (I) led in vivo to an improvement of the length of the colon and a decrease of alterations in lymphoid organs such as Peyer's Patches, on (DSS-) induced colitis mouse models. The inventors have further shown that the administration of a compound of formula (I) led to a significant decreased swelling and lowered signs of inflammation based on a collagen-induced arthritis mouse model.

According to the invention, an «inflammation» is characterized by pain, heat, redness and swelling, and can result from infection, irritation, or injury.

Thus, an «inflammatory disease» refers to a group of diseases and/or disorders that are caused by an excessive or dysregulated inflammation.

According to the invention, «treating and/or preventing an inflammatory disease» may either refer to the treatment and/or prevention of an inflammatory disease, or to inflammation itself, which may occur along with said inflammatory disease in an individual.

Thus, a treatment and/or prevention of an inflammatory disease also includes a treatment and/or prevention of inflammation as such.

According to the invention, «treating and/or preventing» an inflammatory disease includes treating, reducing the likelihood of developing, or delaying the occurrence of said inflammatory disease.

According to the invention, an "individual" may relate to a human or non-human mammal, and preferably to a human.

In a non-limitative manner, inflammatory diseases include: an inflammatory disease associated with an autoimmune disease, a central nervous system (CNS) inflammatory disease, a joint inflammation disease, an inflammatory digestive tract disease, inflammatory skin and other inflammatory diseases related to epithelial cells such as bronchitis, inflammation associated with cancer, such as colon carcinoma, inflammation associated with irritation, and inflammation associated with injury.

Thus, an inflammatory disease can be selected in the list consisting of: an inflammatory disease associated with an autoimmune disease, a central nervous system (CNS) inflammatory disease, a joint inflammation disease, an inflammatory digestive tract disease, inflammatory skin and other inflammatory diseases related to epithelial cells, inflammation associated with cancer, inflammation associated with irritation, and inflammation associated with injury.

In particular, an inflammatory disease is selected in the list consisting of: Inflammatory Bowel Disease, Rheumatoid Arthritis, Crohn's disease, Ulcerative Colitis, Multiple Sclerosis, Alzheimer's disease, Parkinson, osteoarthritis, atherosclerosis, ankylosing spondylitis, psoriasis, dermatitis, Sjogren's syndrome, bronchitis, asthma and inflammation associated with colon carcinoma.

More particularly, an inflammatory disease is selected in the list consisting of: Inflammatory Bowel Disease, Rheumatoid Arthritis, Crohn's disease, Ulcerative Colitis, Multiple Sclerosis, osteoarthritis, ankylosing spondylitis, psoriasis, Sjogren's syndrom, bronchitis, and inflammation associated with colon carcinoma.

More particularly, an inflammatory disease is selected in the list consisting of: Inflammatory Bowel Disease, Rheumatoid Arthritis, Crohn's disease, Ulcerative Colitis, Multiple Sclerosis, osteoarthritis, ankylosing spondylitis, and psoriasis.

Preferably, an inflammatory disease according to the invention includes: Inflammatory Bowel Disease, Crohn's disease, Ulcerative Colitis, Rheumatoid Arthritis and Multiple Sclerosis.

Even more preferably, an inflammatory disease according to the invention includes: Inflammatory Bowel Disease, Rheumatoid Arthritis and Multiple Sclerosis.

An inflammatory disease may also encompass Alzheimer's disease, Parkinson, asthma, atherosclerosis and dermatitis.

As dermatitis, eczema may be cited.

In view of the above, the invention relates to a compound of formula (I) for use in the treatment and/or prevention of an inflammatory disease, which encompasses inflammation as such, and inflammation associated with an inflammatory disease.

Thus, the invention also relates to the use of a compound of formula (I) for treating and/or preventing an inflammatory disease, which encompasses inflammation as such, and inflammation associated with an inflammatory disease.

According to another aspect, a subject-matter of the present invention relates to a compound (Ie), (Id), (8), (9), (10), (11), (44), (46), (47), (48), (49), (50), (51), (52), (53) or its pharmaceutically acceptable salts, either alone or in combination, for use as a medicament.

According to another of its objects, the invention relates to a pharmaceutical composition comprising a compound (Ie), (Id), (8), (9), (10), (11), (44), (46), (47), (48), (49), (50), (51), (52), (53) or its pharmaceutically acceptable salts, either alone or in combination.

The invention also relates to the use of a compound of formula (I) for the preparation of a composition, such as a medicament, for treating and/or preventing inflammation, which encompasses inflammation as such, and inflammation associated with an inflammatory disease.

The invention also relates to a method for treating and/or preventing an inflammatory disease, which includes inflammation as such, and inflammation associated with said inflammatory disease, and which comprises a step of administering a compound of formula (I) to a patient in need thereof.

miRNA-124

MicroRNAs (miRNAs) are small, single-stranded non-coding RNAs that can act in the cytoplasm of a cell to cause a decrease in the expression of their cognate target messenger RNAs or translation of the mRNA's protein product. Mature miRNAs are typically about 19-23 nucleotides in length. This ability of miRNAs to inhibit the production of their target proteins results in the regulation of many types of cellular activities, such as cell-fate determination, apoptosis, differentiation, and oncogenesis.

miR-124 was initially cloned in mouse. Human miR-124 precursor (or miRN-124 or miRNA-124 or micro RNA 124) was cloned from embryonic stem cells. 9 haplotypes of miR-124 precursors have been identified so far (Guo et al., PLoS ONE, 2009, 4(11):e7944), from which 3 are present in the Human, hsa-miR-124-1, hsa-miR-124-2 and hsa-miR-124-3. (Respectively SEQ ID NO:1, SEQ ID NO:2 and SEQ ID NO:3).

The miR-124 microRNA precursor is a small non-coding RNA molecule. The mature ~21 nucleotide microRNAs are processed from hairpin precursor sequences by the Dicer enzyme. The mature sequences are SEQ ID NO: 4 for miR-124-3p and SEQ ID NO: 5 for miR-124-5p.

According to the invention, measuring the level of expression of miR-124 encompasses both measuring the level expression of a precursor or of a mature miR-124.

The invention also relates to a compound of formula (I) for increasing the expression of miR-124 in a biological sample.

Thus, according to another of its objects, the invention relates to an in vitro or ex vivo method for increasing the expression of miR-124 in an eukaryotic cell, comprising at least a step of:
  a) providing an eukaryotic cell,
  b) bringing into contact said cell with a derivative compound, and in particular a compound of formula (I).

Methods or Screening of Candidate Compounds.

One key factor for the success of development of a given drug or vaccine is the possibility to assess efficiently and rapidly its efficacy. It is therefore critical to have proper tools, such as specific biomarkers, to rely upon for assessing the efficacy of a drug or vaccine.

Surprisingly, it has been found that, during inflammation, miR-124 plays an important role. Indeed, the inventors have shown that compounds of formula (I) are able to modulate the expression of miR-124. In particular, the inventors have shown that compounds of the invention could up-regulate (up to 100-fold increase) the expression of miR-124 on Peripheral blood mononuclear cells (PBMCs) from donors, isolated by centrifugation on a FICOLL™ gradient.

Because the inventors have now established that compounds of formula (I) are able to modulate the expression of miR-124, the invention also relates to an in vitro or ex vivo method for screening a quinoline derivative, and in particular a compound of formula (I), presumed effective in treating and/or preventing an inflammatory disease.

Thus, according to another of its objects, the invention relates to an in vitro or ex vivo use of at least one miRNA, said at least one miRNA being miR-124, as a biomarker for screening a quinoline derivative, and in particular a compound of formula (I), presumed effective in treating and/or preventing an inflammatory disease.

Thus, the invention also relates to an in vitro or ex vivo method for screening a quinoline derivative, and in particular a compound of formula (I), presumed effective in treating and/or preventing an inflammatory disease, comprising at least a step of:

a) providing an eukaryotic cell,
b) bringing into contact said cell with a compound of formula (I),
c) measuring an expression of miR-124 in said cell, and
d) selecting the candidate presumed effective in treating and/or preventing an inflammatory disease when the level of expression of miR-124 measured in step c) is modulated relatively to a reference value.

According to the invention, the "modulation" of a level of expression, includes both the up-regulation and the down-regulation of a level of expression. In the sense of the invention, the "modulation" of a level of expression of miR-124 refers preferably to an up-regulation.

In particular, the invention relates to an in vitro or ex vivo method for screening a quinoline derivative, and in particular a compound of formula (I), presumed effective in treating and/or preventing an inflammatory disease, comprising at least a step of:
a) providing an eukaryotic cell,
b) bringing into contact said cell with a compound of formula (I),
c) measuring an expression of miR-124 in said cell, and
d) selecting the candidate presumed effective in treating and/or preventing an inflammatory disease when the level of expression of miR-124 measured in step c) is increased relatively to a reference value.

According to one embodiment, a presence or a level of expression of miR-124 is measured from an eukaryotic cell from a biological sample, and is compared to a control reference value.

In particular, a "biological sample" suitable for the invention may be a biological fluid, such as a blood, a plasma, or a serum, a saliva, an interstitial fluid, or an urine sample; a cell sample, such as a cell culture, a cell line, a stem cell line, or a Peripheral blood mononuclear cells (PBMC) containing sample, a tissue biopsy, such as an oral tissue, a gastrointestinal tissue, a skin, an oral mucosa sample, or a plurality of samples from a clinical trial. The sample can be a crude sample, or can be purified to various degrees prior to storage, processing, or measurement.

In particular, a biological sample suitable for the invention is a Peripheral blood mononuclear cell (PBMC) or a PBMC containing sample. Thus, a biological sample of the invention may be processed from peripheral whole blood using common techniques in the Art, such as density gradient centrifugation, and more particularly FICOLL™ gradient.

PBMC samples, especially the ones which have been processed using a FICOLL™ gradient, are susceptible to include lymphocytes (T cells, B cells, and NK cells), monocytes and dendritic cells. In humans, the frequencies of these populations vary across individuals.

Thus, and in a non-limitative manner, an eukaryotic cell includes any one of cell types as defined above, such as lymphocytes (T cells, B cells, and NK cells), monocytes and dendritic cells.

The step of collecting biological samples for the uses and methods of the invention is performed before carrying out the invention and is not a step of a use or a method in accordance with the invention.

Samples for miRNA assessment can be taken during any desired intervals. For example, samples can be taken hourly, twice per day, daily, weekly, monthly, every other month, yearly, or the like. The sample can be tested immediately, or can be stored for later testing.

The samples can be purified prior to testing. In some embodiments, the miR-124 can be isolated from the remaining cell contents prior to testing. Further, the miR-124 molecules can be separated from the rest of the mRNA in the sample, if desired. For example, the miR-124 can be separated from the mRNA based on size differences prior to testing.

Control reference value to be used for comparing the measured level of expression of miR-124 in a tested biological sample is obtained from a control sample.

Control samples can be taken from various sources. In some embodiments, control samples are taken from the patient prior to treatment or prior to the presence of the disease (such as an archival blood sample). In other embodiments, the control samples are taken from a set of normal, non-diseased members of a population. In another embodiment, a cell assay can be performed on a control cell culture, for example, that has not been treated with the test compound or has been treated with a reference compound, such as DMSO, methylcellulose (MC) or water.

According to one embodiment, for the determination or monitoring of an inflammatory disease in a patient, a control reference value may be obtained from an isolated biological sample obtained on an individual or group of individuals known to not suffer from such condition.

According to another embodiment, for the determination or monitoring of an efficacy of a treatment of an inflammatory disease in a patient, a control reference value may be obtained from an isolated biological sample obtained from an individual or group of individuals known to not suffer from such condition(s), and/or not receiving the treatment the efficacy of which is to be determined or monitored. Alternatively, a control reference value may be obtained from an isolated biological sample obtained from a patient suffering from an inflammatory disease and receiving a treatment the efficacy of which being to be determined or monitored, the isolated biological sample being taken from the patient before administration of the treatment.

Numerous methods are available to the skilled man to measure a presence or level of expression of the miR-124 biomarker.

For example, nucleic acid assays or arrays can be used to assess the presence and/or expression level of miR-124 in a sample.

The sequence of the miR-124 may be used to prepare a corresponding nucleotide acting as complementary probe or primer to be used in different nucleic acid assays for detecting the expression or presence of the miR-124 biomarker in the sample, such as, but not limited to, Northern blots and PCR-based methods (e.g., Real-Time Reverse Transcription-PCR or qRT-PCR). Methods such as qRT-PCR may be used to accurately quantitate the amount of the miRNA in a sample.

Sense and anti-sense probes or primers according to the invention may be obtained using every process known to the man skilled in the art, in particular those that are described in Sambrook et al. (Molecular Cloning: A Laboratory Manual, 3$^{rd}$ ED., 2001, Cold Spring Harbour, N.Y.).

Methods related to the detection and quantification of RNA or DNA are well known in the art. The man skilled in the art may for instance refer to Wang et al. (1989, Proc Natl Acad Sci USA, Vol. 86: 917-921), de Wong et al. (2005, Bio Techniques, Vol. 39 (1): 75-85), de Nolan et al. (2006, Nat Protoc, Vol. 1(3): 1559-1582) et de Klinck et al. (2008, Cancer Research, Vol. 68: 657-663), or also to a general review published by Bustin (2000, Journal of Molecular Endocrinology, Vol. 25: 169-193).

An isolated nucleic acid probe suitable for measuring a presence or level expression of miR-124 is a nucleic acid probe able to specifically hybridize to a miR-124, such as a precursor or a mature miR-124.

Such a nucleic acid probe may comprise from 18 to 30 nucleotides, in particular from 20 to 27, preferably from 20 to 25, preferably from 20, 22, or 25, and more preferably about 25 nucleotides. As previously indicated, such nucleic acid probes may be prepared according to any known methods in the art.

Methods and formulas are well known in the art to predict the optimal hybridization temperature for a given probe and a given target.

Thus, the man skilled in the art may easily calculate an optimal hybridization temperature based on a set of probes, on a given target sequence, and with particular conditions of hybridization.

Advantageously, the optimal hybridization temperature of said probes is between 40° C. and 60° C., and more particularly between 45° C. and 55° C., and preferably is about 48° C.

As examples of buffers useful for hybridizing a nucleic acid probe of the invention to a biomarker of the invention, one may mention, as an hybridization buffer, a buffer comprising 100 mM MES, 1M [Na+], 20 mM EDTA, 0.01% Tween-20, as a non-stringent washing buffer a buffer comprising 6×SSPE, 0.01% Tween-20, and as a stringent washing buffer a buffer comprising 100 mM MES, 0.1M [Na+], 0.01% Tween-20.

In one embodiment, a method for the detection and quantification of nucleic acids may be a fluorescent-dye-based method, wherein nucleic acid concentration is assessed by measuring the fluorescence intensity of ligands, such as dyes, that bind to said nucleic acids. Fluorescent dyes are well known in the art.

Alternatively, said nucleic acid may be quantified using spectrophotometry.

In another embodiment, a method for the detection and quantification of nucleic acids may be a hybridation-based method. Said hybridation-based methods may include PCR and quantitative-PCR (qRT-PCR or q-PCR) techniques or reverse transcriptase/polymerase based techniques. Advantageously, said method may comprise, or be further combined, with a sequencing step.

Those methods may comprise (i) a step of extraction of cellular mRNAs, (ii) a step of reverse transcription of mRNA to DNA using a reverse transcriptase and (iii) a step of DNA amplification from DNA obtained on the previous step. Usually, starting from the same sample, the following nucleic acids are amplified: (a) DNA obtained after a reverse transcription step of the target mRNA and (b) a DNA or a plurality of DNAs obtained after reverse transcription of mRNAs which are constitutively and constantly expressed by cells («housekeeping genes»), such as RNAs coded by genes MRPL19, PUM1 and GADPH.

The amplified DNA can be quantified, after separation by electrophoresis, and measure of DNA bands. Results related to the target mRNA(s) are expressed as relative units in comparison to mRNAs coded by «housekeeping» genes. In some embodiments, the step of separation of amplified DNAs is achieved after agarose gel electrophoresis, and then coloration of DNA bands with ethidium bromide, before quantification of DNA contained in those migration bands with densitometry. In other embodiments, one may use a micro-channel device in which amplified DNA is separated by capillar electrophoresis, before quantification of the emitted signal using a laser beam. Such a device may be a LabChip® device, for instance from the «GX» series, commercialized by the company Caliper LifeSciences (Hopkinton, MA, USA).

Quantitative results obtained by qRT-PCR can sometimes be more informative than qualitative data, and can simplify assay standardization and quality management. Thus, in some embodiments, qRT-PCR-based assays can be useful to measure miRNA levels during cell-based assays. The qRT-PCR method may be also useful in monitoring patient therapy. Commercially available qRT-PCR based methods (e.g., TaqmanR Array™)

Any suitable assay platform can be used to determine the expression or presence of the miRNA in a sample. For example, an assay may be in the form of a dipstick, a membrane, a chip, a disk, a test strip, a filter, a microsphere, a slide, a multiwell plate, or an optical fiber. An assay system may have a solid support on which an oligonucleotide corresponding to the miRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an miRNA.

In some embodiments, an oligonucleotide array for testing for quinoline derivative or drug candidate activity in a biological sample can be prepared or purchased. An array typically contains a solid support and at least one oligonucleotide contacting the support, where the oligonucleotide corresponds to at least a portion of the miR-124 biomarker. In some embodiments, the portion of the miR-124 biomarker comprises at least 5, 10, 15, 20 or more bases.

According to one embodiment, the presence or expression of miR-124 may be assayed in combination with others miRNA also used as biomarkers. In such an embodiment, an array can be used to assess the expression or presence of multiple miRNAs in a sample, including miRNA-124. In general, the method comprises the following steps: a) contacting the sample with an array comprising a probe set under conditions sufficient for specific binding to occur; and b) examining the array to detect the presence of any detectable label, thereby evaluating the amount of the respective target miRNAs in the sample. The use of an expression array allows obtaining a miRNA expression profile for a given sample.

Methods of preparing assays or arrays for assaying miRNAs are well known in the art and are not needed to be further detailed here.

Nucleic acid arrays can be used to detect presence or differential expression of miRNAs in biological samples. Polynucleotide arrays (such as DNA or RNA arrays) typically include regions of usually different sequence polynucleotides ("capture agents") arranged in a predetermined configuration on a support. The arrays are "addressable" in that these regions (sometimes referenced as "array features") have different predetermined locations ("addresses") on the support of array. The region (i.e., a "feature" or "spot" of the array) at a particular predetermined location (i.e., an "address") on the array will detect a particular miRNA target. The polynucleotide arrays typically are fabricated on planar supports either by depositing previously obtained polynucleotides onto the support in a site specific fashion or by site specific in situ synthesis of the polynucleotides upon the support. Arrays to detect miRNA expression can be fabricated by depositing (e.g., by contact- or jet-based methods or photolithography) either precursor units (such as nucleotide or amino acid monomers) or pre-synthesized capture agent. After depositing the polynucleotide capture agents onto the support, the support is typically processed (e.g., washed and blocked for example) and stored prior to use.

An array to detect miRNA expression has at least two, three, four, or five different subject probes. However, in certain embodiments, a subject array may include a probe set having at least 10, at least 20, at least 50, at least 100, at least 200, at least 500, or at least 1,000 or more probes that can detect a corresponding number of miRNAs. In some embodiments, the subject arrays may include probes for detecting at least a portion or all of the identified miRNAs of an organism, or may include orthologous probes from multiple organisms.

A nucleic acid array may be contacted with a sample or labeled sample containing miRNA analytes under conditions that promote specific binding of the miRNA in the sample to one or more of the capture agents present on the array to exhibit an observed binding pattern. This binding pattern can be detected upon interrogating the array. For example, the target miRNAs in the sample can be labeled with a suitable label (such as a fluorescent compound), and the label then can be accurately observed (such as by observing the fluorescence pattern) on the array after exposure of the array to the sample. The observed binding pattern can be indicative of the presence and/or concentration of one or more miRNA components of the sample.

The labeling of miRNAs may be carried using methods well known in the art, such as using DNA ligase, terminal transferase, or by labeling the RNA backbone, etc. In some embodiments, the miRNAs may be labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2 1,4 1, 7',4,7-hexachlorofluorescein (HEX), 6 carboxy 4',5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, RI 10, Eosin, JOE, R6G, Tetramethylrhodamine, Lissamine, ROX, Naptho fluorescein, and the like.

In some embodiments, an oligonucleotide array for assessing immunomodulatory activity can be prepared or purchased, for example from Affymetrix. The array may contain a solid support and a plurality of oligonucleotides contacting the support. The oligonucleotides may be present in specific, addressable locations on the solid support; each corresponding to at least a portion of miRNA sequences which may be differentially expressed upon treatment of a quinoline derivative or a drug candidate in a cell or a patient. The miRNA sequences comprise at least one miR-124 sequence.

When an array is used to assess miRNAs, a typical method can contain the steps of 1) obtaining the array containing surface-bound subject probes; 2) hybridization of a population of miRNAs to the surface-bound probes under conditions sufficient to provide for specific binding (3) post-hybridization washes to remove nucleic acids not bound in the hybridization; and (4) detection of the hybridized miRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on an array surface between complementary binding members, i.e., between surface-bound subject probes and complementary miRNAs in a sample. In certain embodiments, stringent hybridization conditions may be employed. Hybridization is typically performed under stringent hybridization conditions. Standard hybridization techniques which are well-known in the art (e.g. under conditions sufficient to provide for specific binding of target miRNAs in the sample to the probes on the array) are used to hybridize a sample to a nucleic acid array. Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. In general, a "stringent hybridization" and "stringent hybridization wash conditions" in the context of nucleic acid hybridization are typically sequence dependent, and are different under different experimental conditions. Hybridization may be done over a period of about 12 to about 24 hours. The stringency of the wash conditions can affect the degree to which miRNA sequences are specifically hybridized to complementary capture agents. Those of ordinary skill will readily recognize that alternative but comparable hybridization and wash conditions can be utilized to provide conditions of similar stringency.

As an illustration, in one embodiment, the miRNA expression profiling experiments may be conducted using the Affymetrix Genechip miRNA Array 2.0 and following the protocols described in the instruction manual.

In one particular embodiment, said hybridization can be performed using the GeneChip® Hybridization, Wash, and Stain Kit (Affymetrix Ref. #900720).

Advantageously, said hybridization is performed by following the protocols of the manufacturer.

After the miRNA hybridization procedure, the array-surface bound polynucleotides are typically washed to remove unbound nucleic acids. Washing may be performed using any convenient washing protocol, where the washing conditions are typically stringent, as described above. For instance, a washing step may be performed using washing buffers sold by the company Affymetrix (Ref. #900721 and #900722). The hybridization of the target miRNAs to the probes is then detected using standard techniques of reading the array. Reading the resultant hybridized array may be accomplished, for example, by illuminating the array and reading the location and intensity of resulting fluorescence at each feature of the array to detect miRNA/probe binding complexes.

A modulation of the presence or level of expression of miR-124 relatively to the control reference, such as a control reference value from a healthy donor, may be indicative of an inflammatory disease. In particular a reduced or suppressed presence, or a decreased level of expression, of said miRNA relative to a control reference value (i.e., a control reference value from a healthy donor) may be indicative of an inflammatory disease.

Thus, in one embodiment, a use of the invention may comprise obtaining or measuring a level of expression of miR-124 into an isolated biological sample and comparing said measured level of expression to a control reference value. An observation of a modulation of said measured level relatively to said control reference value may be indicative of an inflammatory disease, or of the treatment of said inflammatory disease.

An increased or up-regulated level of expression of miR-124 in the presence of a drug candidate, relatively to a control reference value (i.e., without the treatment by the drug candidate, such as a quinoline derivative) is indicative of a drug candidate presumed effective in treating and/or preventing an inflammatory disease.

Accordingly, when miR-124 from a sample is "increased" or "up-regulated" in a biological sample, as compared to a control reference value, this increase can be of about 5%, 10%, 20%, 30%, 40%, 50%, 60%, 70%, 90%, 100%, 200%, 300%, 500%, 1,000%, 5,000% or more of the comparative control reference value (i.e., without the treatment by the quinoline derivative).

In particular, the measured level expression of miR-124 may be at least a two-fold, preferably at least a four-fold, preferably at least a six-fold, preferably at least an eight-fold, and more preferably at least a ten-fold increase relatively to said control reference value.

According to a preferred embodiment, the measured level expression of miR-124 may be at least a 100-fold increase relatively to said control reference value.

According to one embodiment, a use or a method according to the invention may be implemented for optimizing the dosing regimen of a patient. Patients may respond differently to a given quinoline derivative, in particular a compound of formula (I), depending on such factors as age, health, genetic background, presence of other complications, disease progression, and the co-administration of other drugs. It may be useful to utilize the miR-124 biomarker to assess and optimize the dosage regimen, such as the dose amount and/or the dose schedule, of a quinoline derivative in a patient. In this regard, miR-124-based biomarker can also be used to track and adjust individual patient treatment effectiveness over time. The biomarker can be used to gather information needed to make adjustments in a patient's treatment, increasing or decreasing the dose of an agent as needed. For example, a patient receiving a quinoline derivative can be tested using the miR-124-based biomarker to see if the dosage is becoming effective, or if a more aggressive treatment plan needs to be put into place. The amount of administered drug, the timing of administration, the administration frequency, the duration of the administration may be then adjusted depending on the miR-124 biomarker measurement.

The miR-124 biomarker may also be used to track patient compliance during individual treatment regimes, or during clinical trials. This can be followed at set intervals to ensure that the patients included in the trial are taking the drugs as instructed. Furthermore, a patient receiving a quinoline derivative can be tested using the miR-124 biomarker to determine whether the patient complies with the dosing regimen of the treatment plan. An increased expression level of the biomarker compared to that of an untreated control sample is indicative of compliance with the protocol.

Thus, and without departing from the scope of the invention, a control reference value may be obtained from an eukaryotic cell that is derived from: a biological sample from an healthy donor, and/or a donor that was not previously treated with a given candidate drug, such as a given quinoline derivative.

A biomarker of the invention may be implemented to assess and follow the efficacy of quinoline derivatives, in particular compounds of formula (I). Accordingly, a presence or level of expression of miR-124 may be measured into an isolated biological sample obtained from a patient previously treated with a quinoline derivative, such as a compound of formula (I).

Then, the measured presence or level expression of miR-124 into an isolated biological sample can be compared to a control reference value.

When an increase of the measured level expression of miR-124 relatively to the control reference value is observed, then the measure is indicative of an activity of quinoline derivatives, and in particular compounds of formula (I).

In another embodiment, when an increase of the measured level of expression of miR-124 relatively to the control reference value is observed, then the measure may be indicative of a responsiveness of a patient to a treatment with said quinoline derivatives, in particular said compounds of formula (I).

In another embodiment, when an increase of the measured level relatively to the control reference value is observed, then the measure is indicative of an effectiveness of a treatment with said quinoline derivatives, in particular said compounds of formula (I).

In another embodiment, when an increase of the measured level of expression of miR-124 relatively to the control reference value is observed, then the measure is indicative a therapeutic efficacy of said quinoline derivatives, in particular said compounds of formula (I), as a therapeutic agent for preventing and/or treating an inflammatory disease.

In another embodiment, when an increase of the measured level of expression of miR-124 relatively to the control reference value is observed, then the measure is indicative a therapeutic efficacy of a particular dosage regimen of said quinoline derivatives, in particular said compounds of formula (I) as a therapeutic agent for preventing and/or treating an inflammatory disease, if the control reference value is measured from a biological sample that is derived from a patient treated with another dosage regimen.

The chemical structures and spectroscopic data of some compounds of formula (I) of the invention are illustrated respectively in Table I herebelow and Table II (see examples).

TABLE I

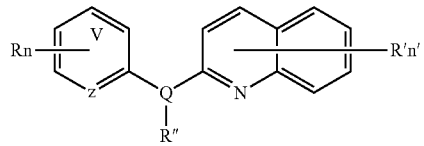

Formula (Ia)

| 1 | 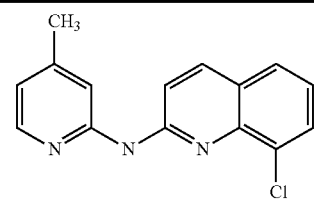 |
| --- | --- |

TABLE I-continued
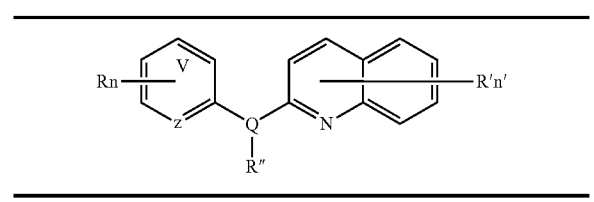
| 2 | 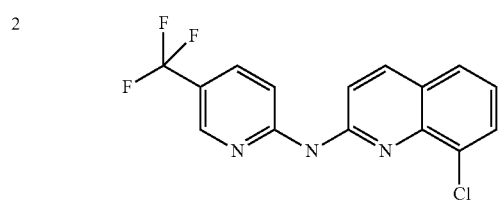 |
|---|---|
| 3 | 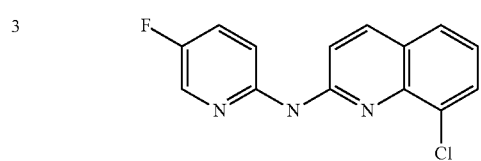 |
| 4 | 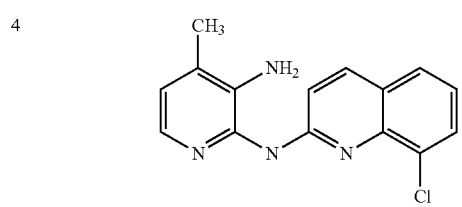 |
| 5 | 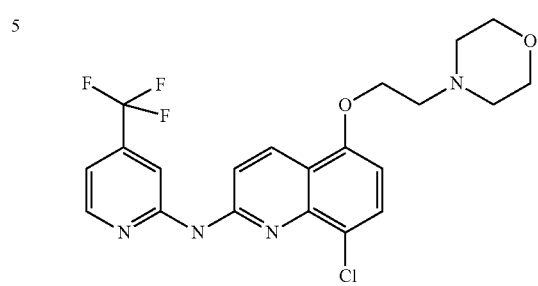 |
| 6 | 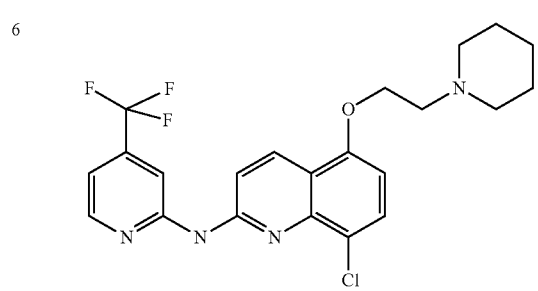 |
| 7 | 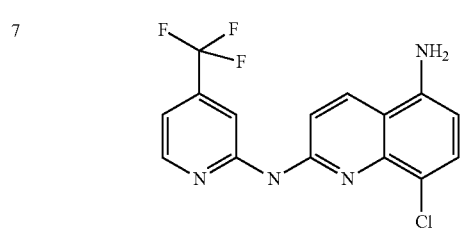 |
TABLE I-continued
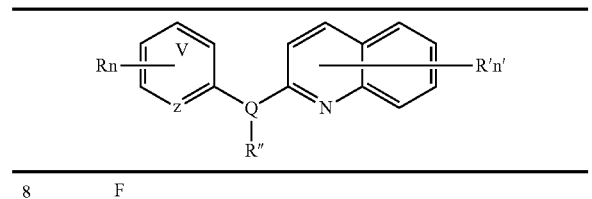
| 8 | 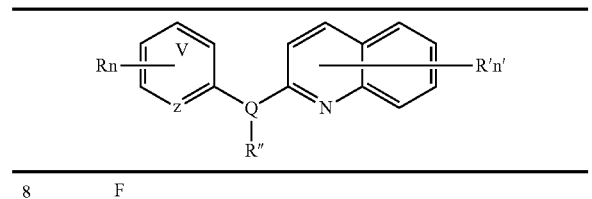 |
|---|---|
| 9 | 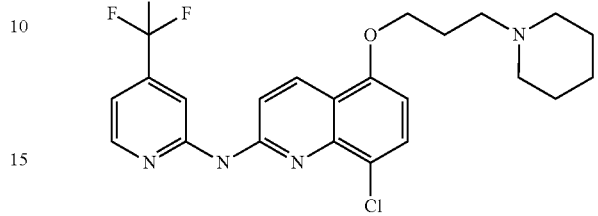 |
| 10 | 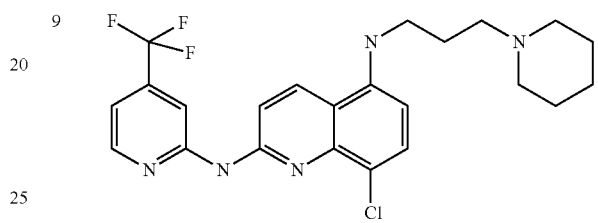 |
| 11 | 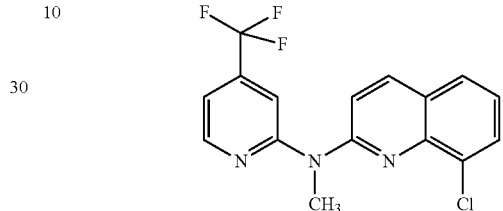 |
| 12 | 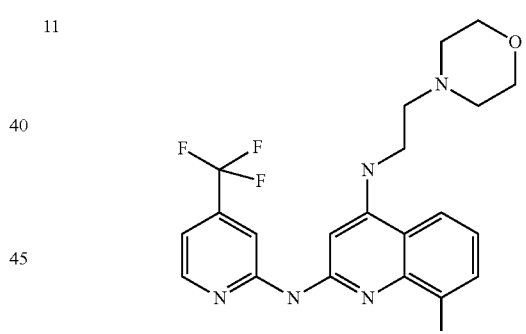 |
| 13 | 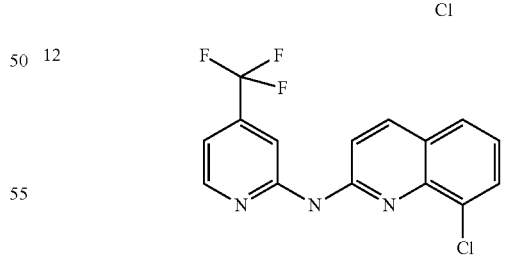 |

TABLE I-continued
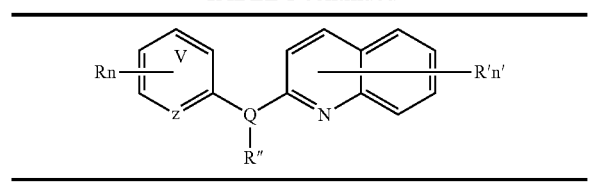
| 14 | 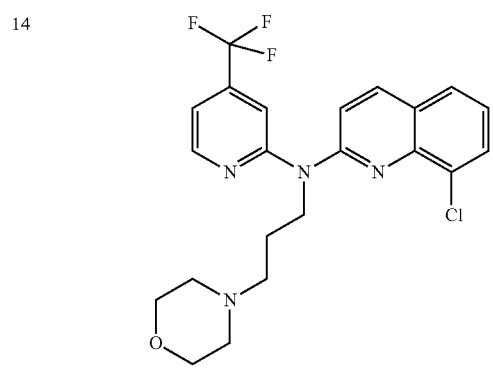 |
| --- | --- |
| 15 | 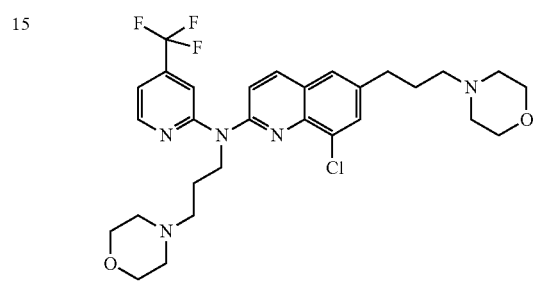 |
| 16 | 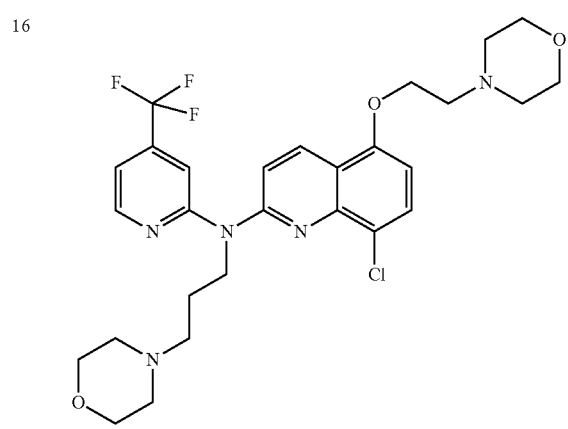 |
| 17 | 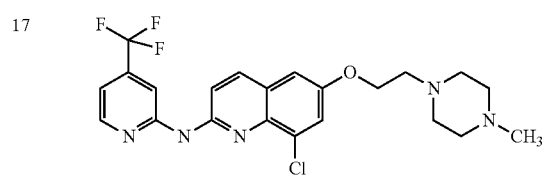 |
| 18 | 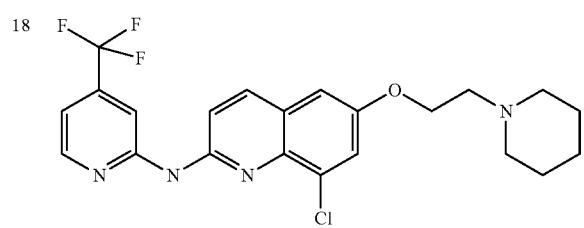 |
TABLE I-continued
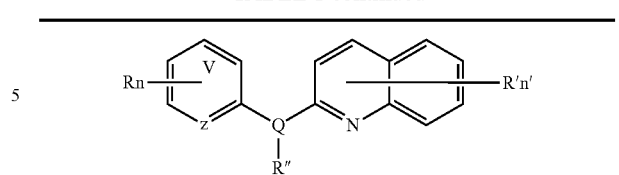
| 19 | 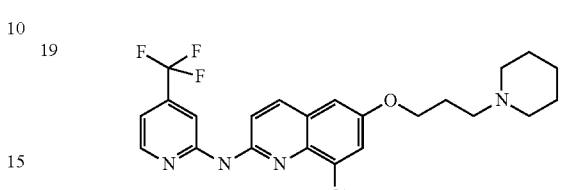 |
| --- | --- |
| 20 | 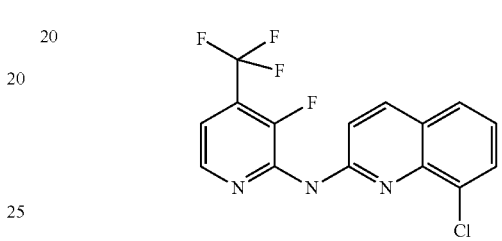 |
| 21 | 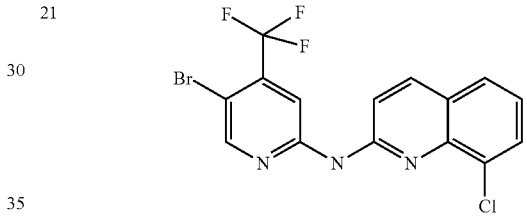 |
| 22 | 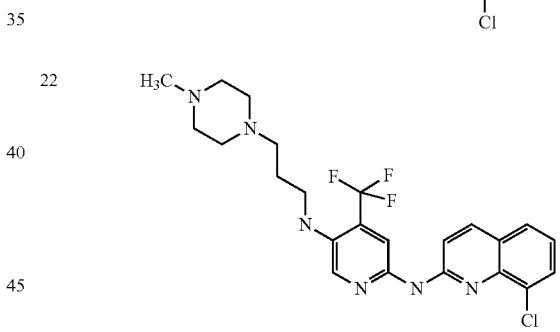 |
| 51 | |
Formula (Ib)
| 23 | 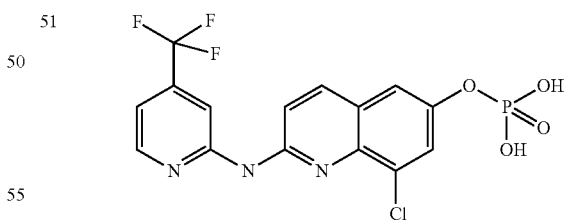 |

TABLE I-continued

| # | Structure |
|---|---|
| 24 | 4-(trifluoromethoxy)phenyl-NH-(8-chloroquinolin-2-yl) |
| 25 | 4-(trifluoromethoxy)-2-amino-phenyl-NH-(8-chloroquinolin-2-yl) |
| 26 | 4-(trifluoromethoxy)-3-chloro-phenyl-NH-(8-chloro-5-aminoquinolin-2-yl) |
| 27 | 4-(trifluoromethoxy)-3-chloro-phenyl-NH-(3-methyl-8-chloro-5-aminoquinolin-2-yl) |
| 28 | 4-(trifluoromethoxy)phenyl-N(CH₃)-(8-chloroquinolin-2-yl) |
| 29 | 4-(trifluoromethoxy)phenyl-NH-(8-chloro-5-(3-piperidinopropoxy)quinolin-2-yl) |
| 30 | 4-(trifluoromethoxy)phenyl-N(3-piperidinopropyl)-(8-chloroquinolin-2-yl) |
| 31 | 4-(trifluoromethoxy)phenyl-N(2-morpholinoethyl)-(8-chloroquinolin-2-yl) |
| 32 | 4-(trifluoromethoxy)phenyl-N(2-pyrrolidinoethyl)-(8-chloroquinolin-2-yl) |

TABLE I-continued
| | | |
|---|---|---|
| 33 | 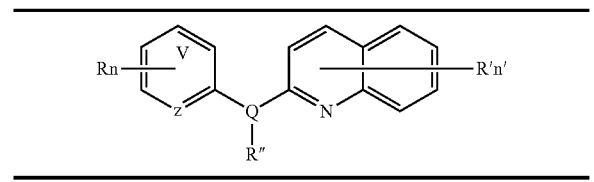 | |
| 34 | 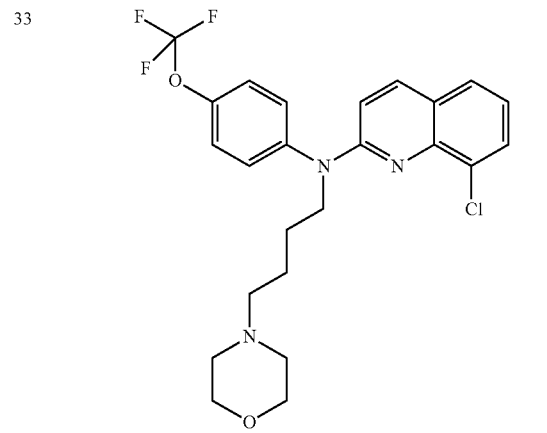 | |
| 35 | 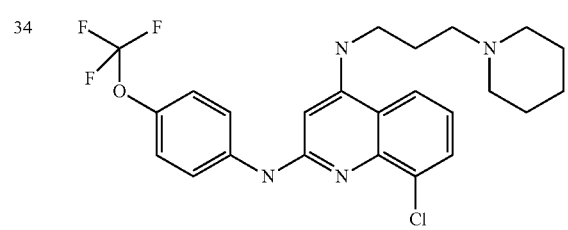 | |
| 36 | 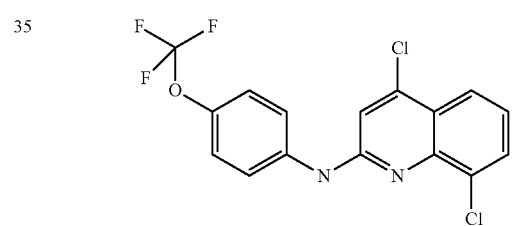 | |
| 37 | 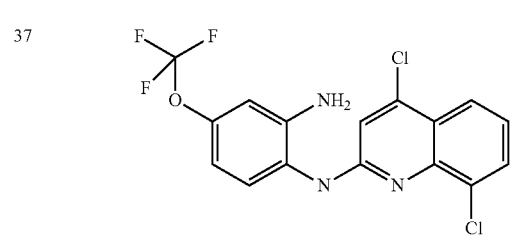 | |
TABLE I-continued
| | | |
|---|---|---|
| 38 | 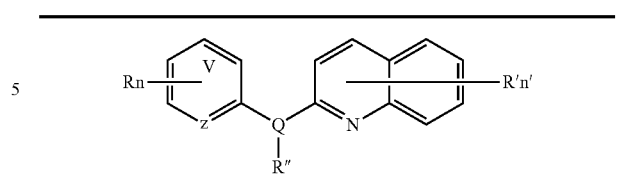 | |
| 39 | 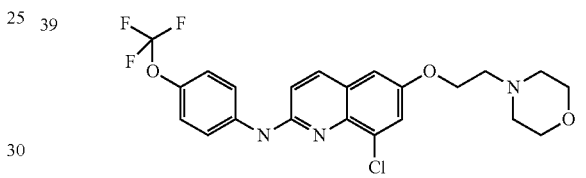 | |
| 40 | 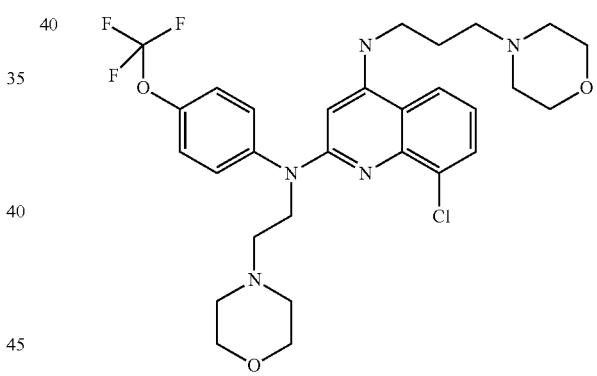 | |
| 41 | 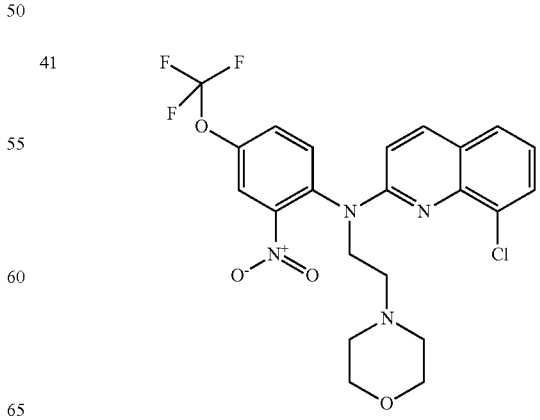 | |

TABLE I-continued
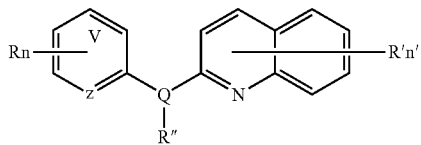
| 42 | 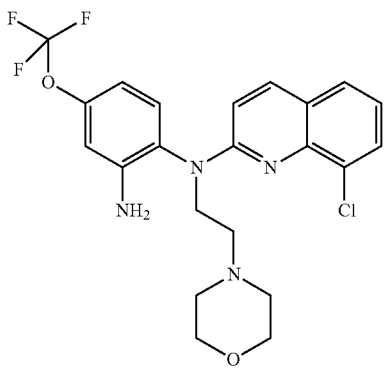 [SMILES: Nc1cc(OC(F)(F)F)ccc1N(CCN1CCOCC1)c1ccc2cccc(Cl)c2n1] |
|---|---|
| 43 | 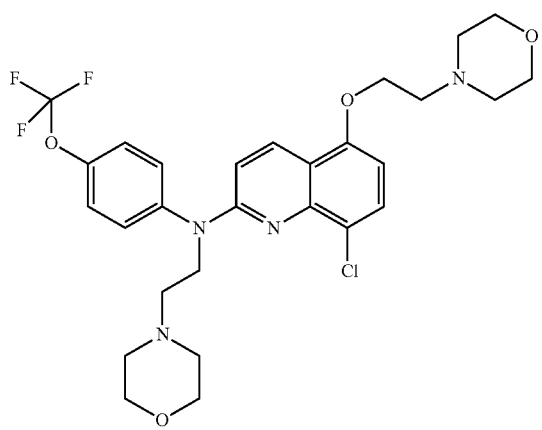 [SMILES: FC(F)(F)Oc1ccc(N(CCN2CCOCC2)c2ccc3c(OCCN4CCOCC4)ccc(Cl)c3n2)cc1] |
| 44 | 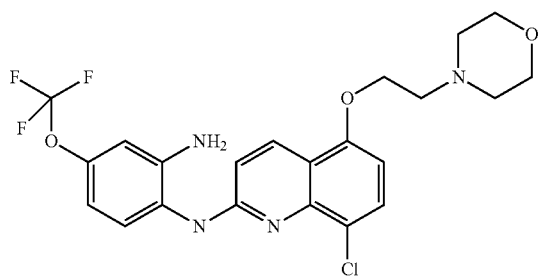 [SMILES: Nc1cc(OC(F)(F)F)ccc1Nc1ccc2c(OCCN3CCOCC3)ccc(Cl)c2n1] |
| 52 | 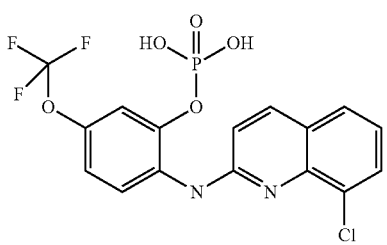 [SMILES: O=P(O)(O)Oc1cc(OC(F)(F)F)ccc1Nc1ccc2cccc(Cl)c2n1] |
TABLE I-continued
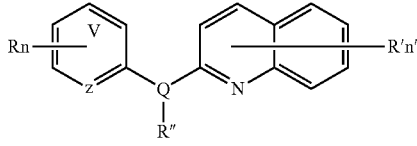
| 53 | 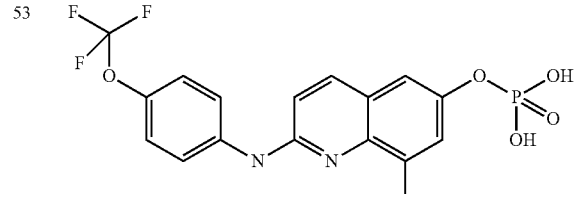 |
Formula (Ic)
| 45 | 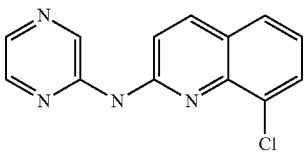 [SMILES: Clc1cccc2ccc(Nc3cnccn3)nc12] |
Formula (Id)
| 46 | 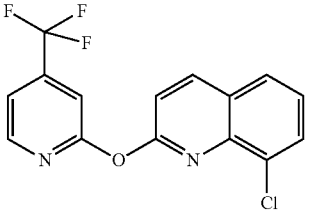 [SMILES: FC(F)(F)c1ccnc(Oc2ccc3cccc(Cl)c3n2)c1] |
| 47 | 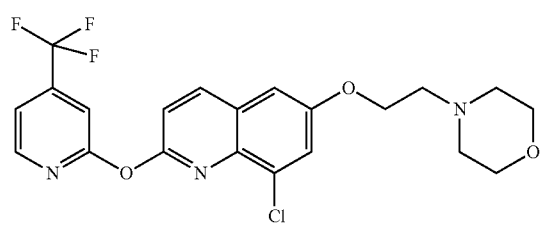 [SMILES: FC(F)(F)c1ccnc(Oc2ccc3cc(OCCN4CCOCC4)cc(Cl)c3n2)c1] |
Formula (Ie)
| 48 | 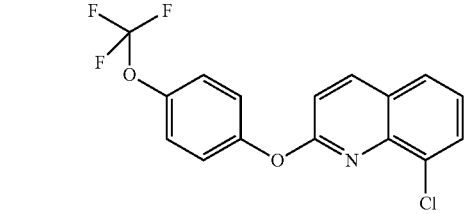 [SMILES: FC(F)(F)Oc1ccc(Oc2ccc3cccc(Cl)c3n2)cc1] |
| 49 | 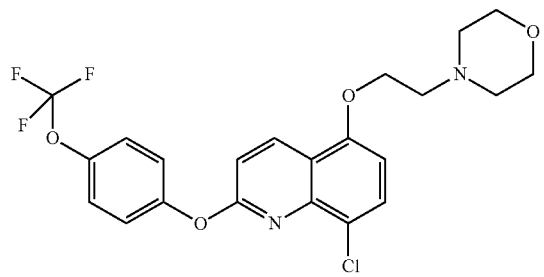 [SMILES: FC(F)(F)Oc1ccc(Oc2ccc3c(OCCN4CCOCC4)ccc(Cl)c3n2)cc1] |

TABLE I-continued

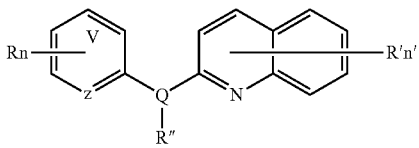

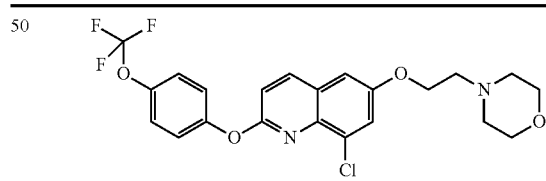

The examples provided herein are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

EXAMPLES

Example 1: 8-chloro-$N^4$-(3-(piperidin-1-yl)propyl)-$N^2$-(4-(trifluoromethyl)pyridin-2-yl)quinoline-2,4-diamine; Compound (9)

o-Chloroaniline (5.3 mL, 50 mmoles, 1 eq.) was placed in pyridine (8 mL). Diethyl malonate (11.4 mL, 75 mmoles, 1.5 eq.) was then added and the reaction mixture was stirred at 130° C. for 14 hours. Upon cooling to room temperature, the reaction mixture was concentrated under reduced pressure and the resulting residue was diluted with dichloromethane. The organic phase was then washed with a saturated aqueous solution of $Na_2CO_3$, dried over $MgSO_4$, filtered and concentrated under reduced pressure. The resulting residue was purified by column chromatography on silica gel to afford ethyl 2-[(2-chlorophenyl)carbamoyl]acetate (2.7 g, 22%).

$^1$H NMR (300 MHz, $CDCl_3$) δ 9.74 (br s, 1H), 8.38 (dd, J=8.1, 1.5 Hz, 1H), 7.40 (dd, J=8.1, 1.5 Hz, 1H), 7.28 (td, J=8.1, 1.5 Hz, 1H), 7.07 (td, J=8.1, 1.5 Hz, 1H), 4.30 (q, J=7.1 Hz, 2H), 3.54 (s, 2H), 1.34 (t, J=7.1 Hz, 3H).

Ethyl 2-[(2-chlorophenyl)carbamoyl]acetate (2.4 g, 9.93 mmoles, 1 eq.) was placed in a THF (9.9 mL)/water (3.8 mL) mix. Sodium hydroxide (477 mg, 11.92 mmoles, 1.2 eq.) was then added and the reaction mixture was stirred for 14 hours at room temperature. Concentrated hydrochloric acid was then added until reaching pH 2 and the resulting solution was extracted with ethyl acetate. The organic phase was then dried over $MgSO_4$, filtered and concentrated under reduced pressure to afford 2-[(2-chlorophenyl)carbamoyl] acetic acid (2 g, 94%).

$^1$H NMR (300 MHz, MeOD) δ 7.98 (dd, J=8.1, 1.5 Hz, 1H), 7.45 (dd, J=8.1, 1.5 Hz, 1H), 7.30 (td, J=8.1, 1.5 Hz, 1H), 7.16 (td, J=8.1, 1.5 Hz, 1H), 3.54 (s, 2H).

A reaction mixture of 2-[(2-chlorophenyl)carbamoyl]acetic acid (3.7 g, 17.32 mmoles, 1 eq.) in polyphosphoric acid (17 g, 173.2 mmoles, 10 eq.) was stirred at 130° C. for 14 hours. The reaction mixture was cooled to room temperature then a 2M aqueous solution of sodium hydroxide was slowly added. The resulting precipitate was filtered, rinsed with water and dried under reduced pressure in a desiccator to afford 8-chloroquinoline-2,4-diol (3 g, 89%).

$^1$H NMR (300 MHz, DMSO) δ 11.66 (br s, 1H), 10.40 (br s, 1H), 7.78 (d, J=7.8 Hz, 1H), 7.66 (d, J=7.8 Hz, 1H), 7.17 (t, J=7.8 Hz, 1H), 5.81 (s, 1H).

MS (ESI) [M–H]$^-$=194.1

A reaction mixture of 8-chloroquinoline-2,4-diol (1.5 g, 7.67 mmoles, 1 eq.) in $POCl_3$ (7.1 mL, 76.7 mmoles, 10 eq.) was stirred at 100° C. for 2 hours. The reaction mixture was cooled to room temperature then water was slowly added. The resulting precipitate was filtered, rinsed with water and dried under reduced pressure in a desiccator to afford 2,4,8-trichloroquinoline (1.6 g, 90%).

$^1$H NMR (300 MHz, DMSO) δ 8.21 (d, J=8.4 Hz, 1H), 8.14 (d, J=8.4 Hz, 1H), 8.11 (s, 1H), 7.78 (t, J=8.4 Hz, 1H).

A reaction mixture of 2,4,8-trichloroquinoline (1 g, 4.30 mmoles, 1 eq.), 2-amino-4-trifluoromethylpyridine (768 mg, 4.73 mmoles, 1.1 eq.), $Pd(OAc)_2$ (19 mg, 0.09 mmol, 2 mol %), XantPhos (50 mg, 0.09 mmol, 2 mol %) and $Cs_2CO_3$ (3.9 g, 12.04 mmoles, 2.8 eq.) in t-BuOH (17.2 mL) was heated at 90° C. for 2 days. Upon cooling to room temperature, the reaction mixture was concentrated under reduced pressure and the resulting residue was diluted with ethyl acetate. The organic phase was then washed with water, dried over $MgSO_4$, filtered and concentrated under reduced pressure. The resulting residue was purified by column chromatography on silica gel to afford (4,8-dichloro-quinolin-2-yl)-(4-trifluoromethyl-pyridin-2-yl)-amine (13) (588 mg, 38%).

$^1$H NMR (300 MHz, $CDCl_3$) δ 9.40 (s, 1H), 8.46 (d, J=5.4 Hz, 1H), 8.06 (dd, J=8.1, 1.5 Hz, 1H), 7.86 (dd, 1=8.1, 1.5 Hz, 1H), 7.81 (s, 1H), 7.40 (t, J=8.1 Hz, 1H), 7.25 (s, 1H), 7.22 (d, J=5.4 Hz, 1H).

MS (ESI) [M+H]$^+$=358.1

A reaction mixture of (4,8-dichloro-quinolin-2-yl)-(4-trifluoromethyl-pyridin-2-yl)-amine (200 mg, 0.54 mmole, 1 eq.), 3-(piperidin-1-yl)propan-1-amine (94 μL, 0.59 mmole, 1.1 eq.), CuI (10 mg, 0.05 mmol, 0.1 eq), L-proline (9 mg, 0.11 mmole, 0.2 eq.), potassium carbonate (148 mg, 1.01 mmole, 2 eq.) in DMSO (1.4 mL) was stirred at 90° C. for 24 hours under an inert atmosphere of argon. The reaction mixture was then partitioned between ethyl acetate and water. Upon decantation, the aqueous phase was further extracted with dichloromethane. The organic phases were gathered, dried over $MgSO_4$, filtered and concentrated under reduced pressure. The resulting residue was purified by column chromatography on silica gel to give 8-chloro-N-(3-piperidin-1-yl-propyl)-$N^2$-(4-trifluoromethyl-pyridin-2-yl)-quinoline-2,4-diamine (9) (48 mg, 7%).

$^1$H NMR (300 MHz, $CDCl_3$) δ 9.55 (s, 1H), 8.40 (d, J=4.8 Hz, 1H), 7.85 (s, 1H), 7.77 (d, J=7.8 Hz, 1H), 7.72 (d, J=7.8 Hz, 1H), 7.62 (s, 1H), 7.18 (t, J=7.8 Hz, 1H), 7.10 (d, J=4.8 Hz, 1H), 5.88 (s, 1H), 3.41-3.31 (m, 2H), 2.59 (t, J=5.4 Hz, 2H), 2.57-2.43 (m, 4H), 2.01-1.92 (m, 2H), 1.79-1.70 (m, 4H), 1.65-1.54 (m, 2H).

$^{13}$C NMR (75 MHz, $CDCl_3$) δ 154.9, 154.0, 152.3, 148.5, 144.2, 132.2, 129.7, 121.7, 119.7, 118.4, 112.4, 109.8, 88.0, 59.6, 55.1, 44.9, 26.1, 24.4, 23.4.

MS (ESI) [M+H]$^+$=464.2

Example 2: 2—N-(8-chloroquinolin-2-yl)-5-N-[3-(4-methylpiperazin-1-yl)propyl]-4-(trifluoromethyl) pyridine-2,5-diamine; Compound (22)

A reaction mixture of 2,8-dichloroquinoline (198 mg, 1.0 mmol, 1 eq.), 5-bromo-4-(trifluoromethyl)pyridin-2-amine (241 mg, 1.0 mmol, 1 eq.), $Pd(OAc)_2$ (4.5 mg, 0.02 mmol, 2 mol %), XantPhos (11.6 mg, 0.02 mmol, 2 mol %) and $Cs_2CO_3$ (782 mg, 2.4 mmoles, 2.4 eq.) in t-BuOH (4 mL)

was heated in a microwave reactor at 120° C. for 70 minutes. Upon cooling to room temperature, the reaction mixture was concentrated under reduced pressure and the resulting residue was diluted with ethyl acetate. The organic phase was then washed with water, dried over MgSO$_4$, filtered and concentrated under reduced pressure. The resulting residue was purified by column chromatography on silica gel to afford N-[5-bromo-4-(trifluoromethyl)pyridin-2-yl]-8-chloroquinolin-2-amine (21) (300 mg, 75%).

$^1$H NMR (300 MHz, CDCl$_3$) δ 9.71 (s, 1H), 8.51 (s, 1H), 8.06 (d, J=9.0 Hz, 1H), 7.81 (m, 2H), 7.65 (d, J=7.8 Hz, 1H), 7.33 (t, 0.1=7.8 Hz, 1H), 7.00 (d, J=9.0 Hz, 1H).

MS (ESI) [M+H]$^+$=403.7

A reaction mixture of N-[5-bromo-4-(trifluoromethyl)pyridin-2-yl]-8-chloroquinolin-2-amine (101 mg, 0.250 mmol, 1 eq.), 3-(4-methylpiperazin-1-yl)propan-1-amine (64 μL, 0.375 mmol, 1.5 eq.), Pd$_2$(dba)$_3$ (28 mg, 0.030 mmol, 12 mol %), XantPhos (43.4 mg, 0.075 mmol, 30 mol %) and sodium tert-butoxide (72 mg, 0.75 mmol, 3 eq.) in a dioxane (1 mL)/DMF (0.1 mL) mixture was heated in a microwave reactor at 120° C. for 70 minutes. Upon cooling to room temperature, the reaction mixture was concentrated under reduced pressure and the resulting residue was diluted with ethyl acetate. The organic phase was then washed with water, dried over MgSO$_4$, filtered and concentrated under reduced pressure. The resulting residue was purified by column chromatography on silica gel to afford 2-N-(8-chloroquinolin-2-yl)-5-N-[3-(4-methylpiperazin-1-yl)propyl]-4-(trifluoromethyl)pyridine-2,5-diamine (22) (52 mg, 43%).

$^1$H NMR (300 MHz, CDCl$_3$) δ 9.39 (s, 1H), 7.97-7.86 (m, 2H), 7.82 (br s, 1H), 7.73 (d, J=7.5 Hz, 1H), 7.56 (d, J=7.5 Hz, 1H), 7.23 (t, J=7.5 Hz, 1H), 6.94 (d, J=9.0 Hz, 2H), 3.34-3.22 (m, 2H), 2.80-2.44 (m, 10H), 2.37 (s, 3H), 1.87 (t, J=6.0 Hz, 2H).

MS (ESI) [M+H]$^+$=479.0

Example 3: 8-chloro-N-methyl-N-(4-(trifluoromethoxy)phenyl)quinolin-2-amine; Compound (28)

8-chloro-N-[4-(trifluoromethoxy)phenyl]quinolin-2-amine, i.e. compound (24), was synthesised as in WO2010/143169, in example 5.

A reaction mixture of 8-chloro-N-(4-(trifluoromethoxy)phenyl)quinolin-2-amine (24) (340 mg, 1.0 mmole, 1 eq.), potassium tert-butoxide (124 mg, 1.1 mmole, 1.1 eq.), and iodomethane (69 μL, 1.1 mmole, 1.1 eq.), in DMF (2 mL) was stirred at room temperature for 4 hours. The reaction mixture was then partitioned between ethyl acetate and water. The organic phases were gathered, dried over MgSO$_4$, filtered and concentrated under reduced pressure. The resulting residue was purified by column chromatography on silica gel to give 8-chloro-N-methyl-N-(4-(trifluoromethoxy)phenyl)quinolin-2-amine (28) (247 mg, 70%).

$^1$H NMR (300 MHz, CDCl$_3$) δ 7.69 (d, J=9.0 Hz, 2H), 7.49 (d, J=7.8 Hz, 1H), 7.36-7.25 (m, 4H), 7.14 (t, J=7.8 Hz, 1H), 6.75 (d, J=9.0 Hz, 1H), 3.69 (s, 3H).

MS (ESI) [M+H]$^+$=353.1

Example 4: 8-chloro-N-(3-(piperidin-1-yl)propyl)-N-(4-(trifluoromethoxy)phenyl)quinolin-2-amine; Compound (30)

8-chloro-N-[4-(trifluoromethoxy)phenyl]quinolin-2-amine, i.e. compound (24), was synthesised as in WO2010/143169, in example 5.

A reaction mixture of 8-chloro-N-[4-(trifluoromethoxy)phenyl]quinolin-2-amine (24) (500 mg, 1.47 mmole, 1 eq.) and NaH (177 mg, 4.43 mmoles, 3 eq.) in anhydrous DMF (2 mL) was stirred at room temperature for 30 minutes. A reaction mixture of 1-(3-chloropropyl)piperidine hydrochloride (292 mg, 1.47 mmole, 1 eq.), KI (245 mg, 1.47 mmole, 1 eq.) and Et$_3$N (205 μL, 1.47 mmole, 1 eq.) in anhydrous DMF (5 mL) was stirred at room temperature for 30 minutes under an inert atmosphere of argon. The activated quinoline was then added to the piperidine chain and the resulting reaction mixture was stirred at 90° C. for 4 hours. The reaction mixture was then concentrated under reduced pressure and the resulting residue was diluted with ethyl acetate. The organic phase was washed with a saturated aqueous solution of brine, dried over MgSO$_4$, filtered and concentrated under reduced pressure. The resulting residue was purified by column chromatography on silica gel to afford 8-chloro-N-(3-(piperidin-1-yl)propyl)-N-(4-(trifluoromethoxy)phenyl)quinolin-2-amine (30) (472 mg, 69%).

$^1$H NMR (300 MHz, CDCl$_3$) δ 7.73-7.63 (m, 2H), 7.48 (d, J=7.9 Hz, 1H), 7.39-7.26 (m, 4H), 7.13 (t, J=7.9 Hz, 1H), 6.67 (d, J=9.1 Hz, 1H), 4.26-4.14 (m, 2H), 2.52-2.33 (m, 6H), 2.11-1.97 (m, 2H), 1.64-1.52 (m, 4H), 1.45 (s, 2H).

$^{13}$C NMR (75 MHz, CDCl$_3$) δ 156.5, 147.3, 144.1, 143.5, 137.1, 130.8, 129.7, 129.1, 126.4, 124.7, 122.7, 122.4, 118.9 (t, J=222 Hz), 112.5, 56.9, 54.5, 49.6, 25.6, 24.6, 24.3.

MS (ESI) [M+H]$^+$=464.4

Example 5: 8-chloro-2-((4-(trifluoromethyl)pyridin-2-yl)oxy)quinoline compound (46)

A reaction mixture of 2,8-dichloroquinoline (79 mg, 0.4 mmol, 1 eq.), 2-hydroxy-4-(trifluoromethyl)pyridine (65 mg, 0.4 mmol, 1 eq.), CuI (76 mg, 0.4 mmol, 1 eq.) and Cs$_2$CO$_3$ (391 mg, 1.2 mmol, 3 eq.) in DMF (6 mL) was heated in a microwave reactor at 150° C. for 50 minutes. Upon cooling to room temperature, water was added to the reaction mixture. The undissolved solids were filtered through celite and the resulting filtrate was twice extracted with ethyl acetate. The organic phase was washed with water and a saturated aqueous solution of brine, dried over MgSO$_4$, filtered and concentrated under reduced pressure. The resulting residue was purified by column chromatography on silica gel to afford 8-chloro-2-{[4-(trifluoromethyl)pyridin-2-yl]oxy}quinoline (46) (68 mg, 52%).

$^1$H NMR (300 MHz, CDCl$_3$) δ 8.40 (d, J=7.2 Hz, 1H), 8.34 (d, J=8.8 Hz, 1H), 8.18 (d, J=8.8 Hz, 1H), 7.90 (d, J=7.2 Hz, 1H), 7.85 (d, J=7.9 Hz, 1H), 7.56 (t, J=7.9 Hz, 1H), 6.98 (s, 1H), 6.53 (d, J=7.9 Hz, 1H).

$^{13}$C NMR (75 MHz, CDCl$_3$) δ 161.6, 151.2, 143.4, 142.3, 138.7, 138.2, 137.4, 133.4, 130.6, 129.1, 127.6, 126.7, 120.2, 119.7, 102.3.

MS (ESI) [M+H]$^+$=325.1

Example 6: 8-chloro-2-(4-(trifluoromethoxy)phenoxy)quinoline; Compound (48)

A reaction mixture of 2,8-dichloroquinoline (2×79 mg, 2×0.4 mmol, 1 eq.), 4-(trifluoromethoxy)phenol (2×52 μL, 2×0.4 mmol, 1 eq.), CuI (2×76 mg, 2×0.4 mmol, 1 eq.) and Cs$_2$CO$_3$ (2×391 mg, 2×1.2 mmol, 3 eq.) in DMF (2×6 mL) was heated in a microwave reactor at 150° C. for 50 minutes.

Upon cooling to room temperature, water was added to the reaction mixture. The undissolved solids were filtered through celite and the resulting filtrate was twice extracted with ethyl acetate. The organic phase was washed with water and a saturated aqueous solution of brine, dried over MgSO$_4$, filtered and concentrated under reduced pressure. The resulting residue was purified by column chromatography on silica gel to afford 8-chloro-2-[4-(trifluoromethoxy)phenoxy]quinoline 48 (212 mg, 78%).

$^1$H NMR (300 MHz, CDCl$_3$) δ 8.12 (d, J=8.8 Hz, 1H), 7.73 (d, J=8.1 Hz, 1H), 7.66 (d, J=8.1 Hz, 1H), 7.46 (d, J=9.1 Hz, 2H), 7.38-7.22 (m, 3H), 7.12 (d, J=8.8 Hz, 1H).

$^{13}$C NMR (75 MHz, CDCl$_3$) δ 161.5, 151.9, 145.9, 142.7, 140.5, 132.0, 130.3, 127.0, 126.4, 125.1, 122.8, 122.2, 119.0 (t, J=255 Hz), 113.6.

MS (ESI) [M+H]$^+$=340.1

The structures of other compounds of the invention have been confirmed by NMR spectra.

TABLE II

| Ex | Characterizations |
|---|---|
| 8 | $^1$H NMR (300 MHz, CDCl$_3$) δ 9.57 (s, 1H), 8.45 (d, J = 9.0 Hz, 1H), 8.43 (d, J = 5.1 Hz, 1H), 7.90 (br s, 1H), 7.66 (d, J = 8.4 Hz, 1H), 7.18 (d, J= 5.1 Hz, 1H), 6.99 (d, J = 9.0 Hz, 1H), 6.68 (d, J = 8.4 Hz, 1H), 4.17 (t, J = 6.3 Hz, 2H), 2.56 (t, J = 7.8 Hz, 2H), 2.50 – 2.39 (m, 4H), 2.17 – 2.04 (m, 2H), 1.66 – 1.59 (m, 4H), 1.51 – 1.43 (m, 2H).<br>$^{13}$C NMR (75 MHz, CDCl$_3$) δ 154.1, 153.8, 152.5, 148.7, 143.8, 133.5, 129.8, 122.9, 117.5, 113.2, 112.5, 109.9, 103.6, 67.2, 56.2, 54.8, 26.9, 26.1, 24.5.<br>MS (ESI) [M + H]$^+$ = 465.4 |
| 9 | $^1$H NMR (300 MHz, CDCl3) δ 9.55 (s, 1H), 8.40 (d, J = 4.8 Hz, 1H), 7.85 (s, 1H), 7.77 (d, J = 7.8 Hz, 1H), 7.72 (d, J = 7.8 Hz, 1H), 7.62 (s, 1H), 7.18 (t, J = 7.8 Hz, 1H), 7.10 (d, J = 4.8 Hz, 1H), 5.88 (s, 1H), 3.41 – 3.31 (m, 2H), 2.59 (t, J = 5.4 Hz, 2H), 2.57 – 2.43 (m, 4H), 2.01 – 1.92 (m, 2H), 1.79 – 1.70 (m, 4H), 1.65 – 1.54 (m, 2H),<br>$^{13}$C NMR (75 MHz, CDCl$_3$) δ 154.9, 154.0, 152.3, 148.5, 144.2, 132.2, 129.7, 121.7, 119.7, 118.4, 112.4, 109.8, 88.0, 59.6, 55.1, 44.9, 26.1, 24.4, 23.4.<br>MS (ESI) [M + H]$^+$ = 464.2 |
| 10 | $^1$H NMR (300 MHz, CDCl3) δ 8.53 (d, J = 4.8 Hz, 1H), 8.10 (s, 1H), 8.04 (d, J = 9.0 Hz, 1H), 7.76 (dd, J = 7.5, 1.2 Hz, 1H), 7.64 (dd, J = 7.5, 1.2 Hz, 1H), 7.43 (d, J = 9.0 Hz, 1H), 7.30 (t, J = 7.5 Hz, 1H), 7.15 (d, J = 4.8 Hz, 1H), 3.87 (s, 3H).<br>$^{13}$C NMR (75 MHz, CDCl$_3$) δ 157.6, 155.8, 149.0, 143.4, 138.0, 131.9, 130.0, 126.3, 126.1, 124.4, 115.0, 113.1, 113.0, 111.6, 111.5, 36.3.<br>MS (ESI) [M + H]$^+$ = 338.1 |
| 11 | $^1$H NMR (300 MHz, CDCl$_3$) δ 9.50 (s, 1H), 8.41 (br s, 1H), 8.14 (br s, 1H), 7.72 (d, J = 7.8 Hz, 1H), 7.53 (d, J = 7.8 Hz, 1H), 7.21 (t, J = 7.8 Hz, 1H), 7.11 (s, 1H), 5.96 (s, 1H), 5.88 (s, 1H), 3.77 (s, 4H), 3.25 (s, 2H), 2.77 (s, 2H), 2.54 (s, 4H).<br>$^{13}$C NMR (75 MHz, CDCl$_3$) δ 154.8, 153.7, 151.1, 148.5, 144.2, 132.4, 129.9, 122.4, 118.2, 118.0, 112.5, 109.9, 89.2, 67.2, 56.0, 53.2, 38.9.<br>MS (ESI) [M + H]$^+$ = 452.1 |
| 13 | $^1$H NMR (300 MHz, CDCl$_3$) δ 9.40 (s, 1H), 8.46 (d, J = 5.4 Hz, 1H), 8.06 (dd, J = 7.8, 1.5 Hz, 1H) 7.86 (dd, J = 7.8, 1.5 Hz, 1H), 7.81 (s, 1H), 7.40 (t, J = 7.8 Hz, 1H), 7.25 (s, 1H), 7.22 (d, J = 5.4 Hz, 1H).<br>MS (ESI) [M + H]$^+$ = 358.1 |
| 14 | $^1$H NMR (300 MHz, CDCl$_3$) δ 8.51 (d, J = 4.8 Hz, 1H), 7.99 (d, J = 9.0 Hz, 1H), 7.79 (s, 1H), 7.75 (d, J = 7.5 Hz, 1H), 7.63 (d, J = 7.5 Hz, 1H), 7.39 (d, J = 9.0 Hz, 1H), 7.29 (t, J = 7.5 Hz, 1H), 7.14 (d, J = 4.8 Hz, 1H), 4.48 (t, J = 7.2 Hz, 2H), 3.77 – 3.59 (m, 4H), 2.57 – 2.33 (m, 6H), 2.13 – 1,97 (m, 2H).<br>MS (ESI) [M + H]$^+$ = 451.2 |
| 15 | $^1$H NMR (300 MHz, CDCl$_3$) δ 8.47 (d, J = 4.8 Hz, 1H), 7.89 (d, J = 9.0 Hz, 1H), 7.68 (s, 1H), 7.49 (d, J = 2.7 Hz, 1H), 7.38 (d, J = 9.0 Hz, 1H), 7.08 (d, J = 4.8 Hz, 1H), 6.99 (d, J = 2.7 Hz, 1H), 4.45 (t, J = 6.9 Hz, 2H), 4.21 (t, J = 5.4 Hz, 2H), 3.83 – 3.64 (m, 8H), 2.87 (t, J = 5.4 Hz, 2H), 2.70 – 2.56 (m, 4H), 2.56 – 2.36 (m, 6H), 2.12 – 1.96 (m, 2H).<br>MS (ESI) [M + H]$^+$ = 580.4 |
| 16 | $^1$H NMR (300 MHz, CDCl$_3$) δ 8.50 (d, J = 4.8 Hz, 1H), 8.37 (d, J = 9.0 Hz, 1H), 7.80 (s, 1H), 7.61 (d, J = 8.4 Hz, 1H), 7.34 (d, J = 9.0 Hz, 1H), 7.13 (d, J = 4.8 Hz, 1H), 6.65 (d, J = 8.4 Hz, 1H), 4.47 (t, J = 6.9 Hz, 2H), 4.26 (t, J = 5.4 Hz, 2H), 3.78 – 3.64 (m, 8H), 2.92 (t, J = 5.4 Hz, 2H), 2.69 – 2.56 (m, 4H), 2.55 – 2.38 (m, 6H), 2.05 (t, J = 6.9 Hz, 2H).<br>MS (ESI) [M + H]$^+$ = 580.2 |
| 17 | $^1$H NMR (300 MHz, CDCl$_3$) δ 9.47 (s, 1H), 8.41 (d, J = 5.1 Hz, 1H), 8.24 (br s, 1H), 7.88 (d, J = 8.7 Hz, IH), 7.49 (d, J = 2.7 Hz, 1H), 7.14 (d, J = 5.1 Hz, 1H), 6.99 (d, J = 8.7 Hz, 1H), 6.94 (d, J = 2.7 Hz, 1H), 4.17 (t, J = 5.7 Hz, 2H), 2.87 (t, J = 5.7 Hz, 2H), 2.75 – 2.61 (m, 4H), 2.57 – 2.45 (m, 4H), 2.31 (s, 3H),<br>MS (ESI) [M + H]$^+$ = 233.6 |
| 18 | $^1$H NMR (300 MHz, CDCl$_3$) δ 9.48 (s, 1H), 8.42 (d, J = 4.8 Hz, 1H), 7.94 (d, J = 8.7 Hz, 1H), 7.78 (br s, 1H), 7.53 (d, J = 2.4 Hz, 1H), 7.16 (d, J = 4.8 Hz, 1H), 7.06 – 6.98 (m, 2H), 4.20 (t, J = 6.0 Hz, 2H), 2.84 (t, J = 6.0 Hz, 2H), 2.61 – 2.50 (m, 4H), 1.69 – 1.59 (m, 4H), 1.52 – 1.42 (m, 2H).<br>MS (ESI) [M + H]$^+$ = 450.9 |
| 19 | $^1$H NMR (300 MHz, CDCl$_3$) δ 9.48 (s, 1H), 8.41 (d, J = 4.5 Hz, 1H), 8.34 (s, 1H), 7.87 (d, J = 8.7 Hz, 1H), 7.46 (s, 1H), 7.14 (d, J = 4.5 Hz, 1H), 7.01 – 6.89 (m, 2H), 4.08 (t, J = 5.7 Hz, 2H), 2,66 – 2.41 (m, 6H), 2.13 – 1.99 (m, 2H), 1.72 – 1.59 (m, 4H), 1.55 – 1.41 (m, 2H).<br>MS (ESI) [M + H]$^+$ = 465.0 |
| 20 | $^1$H NMR (300 MHz, CDCl$_3$) δ 8.70 (d, J = 9.0 Hz, 1H), 8.24 (d, J = 4.8 Hz, 1H), 8.19 (d, J = 9.0 H.z, 1H), 8.11 (s, 1H), 7.79 (d, J = 7.8 Hz, 1H), 7.71 (d, J = 7.8 Hz, 1H), 7.34 (t, J = 7.8 Hz, 1H), 7.08 (t, J = 4.8 Hz, 1H).<br>MS (ESI) [M + H]$^+$ = 341.9 |

TABLE II-continued

| Ex | Characterizations |
|---|---|
| 21 | $^1$H NMR (300 MHz, CDCl$_3$) δ 9.71 (s, 1H), 8.51 (s, 1H), 8.06 (d, J = 9.0 Hz, 1H), 7.81 (m, 2H), 7.65 (d, J = 7.8 Hz, 1H), 7.33 (t, J = 7.8 Hz, 1H), 7.00 (d, J = 9.0 Hz, 1H). MS (ESI) [M + H]$^+$ = 403.7 |
| 22 | $^1$H NMR (300 MHz, CDCl$_3$) δ 9.39 (s, 1H), 7.97 – 7.86 (m, 2H), 7.82 (br s, 1H), 7.73 (d, J = 7.5 Hz, 1H), 7.56 (d, J = 7.5 Hz, 1H), 7.23 (t, J = 7.5 Hz, 1H), 6.94 (d, J = 9.0 Hz, 2H), 3.34 – 3.22 (m, 2H), 2.80 – 2.44 (m, 10H), 2.37 (s, 3H), 1.87 (t, J = 6.0 Hz, 2H). MS (ESI) [M + H]$^+$ = 479.0 |
| 28 | $^1$H NMR (300 MHz, CDCl$_3$) δ 7.69 (d, J = 9.0 Hz, 2H), 7.49 (d, J = 7.8 Hz, 1H), 7.36 – 7.25 (m, 4H), 7.14 (t, J = 7.8 Hz, 1H), 6.75 (d, J = 9.0 Hz, 1H), 3.69 (s, 3H). MS (ESI) = 353.1 |
| 29 | $^1$H NMR (300 MHz, CDCl$_3$) δ 8.26 (d, J = 9.0 Hz, 1H), 7.93 (d, J = 9.0 Hz, 2H), 7.54 (d, J = 8.4 Hz, 1H), 7.21 (d, J = 9.0 Hz, 3H), 6.83 (d, J = 9.0 Hz, 1H), 6.53 (d, J = 8.4 Hz 1H), 4.06 (t, J = 6.0 Hz, 2H), 2.56 (t, J = 7.5 Hz, 2H), 2.52 – 2.40 (m, 4H), 2.14 – 2.01 (m, 2H), 1.69 – 1.58 (m, 4H), 1.50 – 1.41 (m, 2H). MS (ESI) [M + H]$^+$ = 480.3 |
| 30 | $^1$H NMR (300 MHz, CDCl$_3$) δ 7.73 – 7.63 (m, 2H), 7.48 (d, J = 7.9 Hz, 1H) 7.39 – 7.26 (m, 4H), 7.13 (t, J = 7.9 Hz, 1H), 6.67 (d, J = 9.1 Hz, 1H), 4.26 – 4.14 (m, 2H), 2.52 – 2.33 (m, 6H), 2.11 – 1.97 (m, 2H), 1.64 – 1.52 (m, 4H), 1.45 (s, 2H). $^{13}$C NMR (75 MHz, CDCl$_3$) δ 156.5, 147.3, 144.1, 143.5, 137.1, 130.8, 129.7, 129.1, 126.4, 124.7, 122.7, 122.4, 121.8, 118.9, 112.5, 56.9, 54.5, 49.6, 25.6, 24.6, 24.3. MS (ESI) [M + H]$^+$ = 464.4 |
| 31 | $^1$H NMR (300 MHz, CDCl$_3$) δ 7.74 – 7.65 (m, 2H), 7.50 (d, J = 7.8 Hz, 1H), 7.42 – 7.28 (m, 4H), 7.14 (t, J = 7.8 Hz, 1H), 6.63 (d, J = 9.0 Hz, 1H), 4.34 (t, J = 6.9 Hz, 2H), 3.66 (t, J = 4.5 Hz, 4H), 2.78 (t, J = 6.9 Hz, 2H), 2.59 (t, J = 4.5 Hz, 4H). MS (ESI) [M + H]$^+$ = 452.3 |
| 32 | $^1$H NMR (300 MHz, CDCl$_3$) δ 7.70 (d, J = 9.0 Hz, 1H), 7.69 (dd, J = 7.8, 1.2 Hz, 1H), 7.50 (dd, J = 7.8, 1.2 Hz, 1H), 7.38 – 7.26 (m, 4H), 7.15 (t, J = 7.8 Hz, 1H), 6.66 (d, J = 9.0 Hz, 1H), 4.35 (t, J = 7.5 Hz, 2H), 2.91 (t, J = 7.5 Hz, 2H), 2.70 – 2.60 (m, 4H), 1.83 – 1.74 (m, 4H). MS (ESI) [M + H]$^+$ = 436.1 |
| 33 | $^1$H NMR (300 MHz, CDCl$_3$) δ 7.66 (d, J = 9.3 Hz, 1H), 7.64 (dd, J = 7.8, 1.5 Hz, 1H), 7.46 (dd, J = 7.8, 1.5 Hz, 1H), 7.29 – 7.22 (m, 4H), 7.10 (t, J = 7.8 Hz, 1H), 6.59 (d, J = 9.3 Hz, 1H), 4.16 (t, J = 7.5 Hz, 2H), 3.66 (t, J = 4.8 Hz, 4H), 2.46 – 2.36 (m, 6H), 1.78 (dt, J = 15.0, 7.2 Hz, 2H), 1.59 (dt, J = 15.0, 7.2 Hz, 2H). MS (ESI) [M + H]$^+$ = 480.1 |
| 34 | $^1$H NMR (300 MHz, CDCl$_3$) δ 7.80 (d, J = 9.0 Hz, 2H), 7.75 (d, J = 8.4 Hz, 1H), 7.66 (d, J = 8.4 Hz, 1H), 7.58 (br s, 1H), 7.19 (d, J = 9.0 Hz, 2H), 7.11 (t, J = 8.4 Hz, 1H), 5.83 (s, 1H), 3.24 (t, J = 5.4 Hz, 2H), 2.61 – 2.46 (m, 6H), 1.91 (t, J = 5.4 Hz, 2H), 1.78 – 1.68 (m, 4H), 1.62 – 1.52 (m, 2H). MS (ESI) [M + H]$^+$ = 479.3 |
| 35 | $^1$H NMR (300 MHz, CDCl$_3$) δ 8.00 (dd, J = 7.8, 1.5 Hz, 1H), 7.87 (d, J = 9.0 Hz, 2H), 7.80 (dd, J = 7.8, 1.5 Hz, 1H), 7.32 (t, J = 7.8 Hz, 1H), 7.27 (d, J = 9.0 Hz, 2H), 7.05 (s, 1H), 6.84 (br s, 1H). |
| 36 | $^1$H NMR (300 MHz, MeOD) δ 8.37 (d, J = 9.0 Hz, 1H), 8.26 (d, J = 9.3 Hz, 2H), 7.60 (d, J = 8.4 Hz, 1H), 7.22 (d, J = 9.3 Hz, 2H), 7.00 (d, J = 9.0 Hz, 1H), 6.75 (d, J = 8.4 Hz, 1H), 4.29 (t, J = 5.4 Hz, 2H), 3.73 (t, J = 4.8 Hz, 4H), 2.94 (t, J = 5.4 Hz, 2H), 2.66 (t, J = 4.8 Hz, 4H), MS (ESI) [M + H]$^+$ = 468.1 |
| 37 | $^1$H NMR (300 MHz, MeOD) δ 7.92 (dd, J = 7.8, 1.5 Hz, 1H), 7.71 (dd, J = 7.8, 1.5 Hz, 1H), 7.63 (d, J = 8.7 Hz, 1H), 7.24 (t, J = 7.8 Hz, 1H), 7.05 (s, 1H), 6.83 – 6.79 (m, 1H), 6.64 – 6.58 (m, 1H). MS (ESI) [M + H]$^+$ = 388.0 |
| 38 | $^1$H NMR (300 MHz, CDCl$_3$) δ 7.87 (d, J = 7.8 Hz, 1H), 7.70 (d, J = 7.8 Hz, 1H), 7.37 (d, J = 9.0 Hz, 2H), 7.32 (d, J = 9.0 Hz, 2H), 7.17 (t, J = 7.8 Hz, 1H), 6.69 (s, 1H), 4.29 (t, J = 6.9 Hz, 2H), 3.63 (t, J = 4.5 Hz, 4H), 2.73 (t, J = 6.9 Hz, 2H), 2.55 (t, J = 4.5 Hz, 4H). MS (ESI) [M + H]$^+$ = 486.1 |
| 39 | $^1$H NMR (300 MHz, CDCl$_3$) δ 7.87 (d, J = 9.0 Hz, 2H), 7.78 (d, J = 8.7 Hz, 1H), 7.44(d J = 2.7 Hz, 1H), 7.21 (d, J = 9.0 Hz, 2H), 6.95 (br s, 1H), 6.91 (d, J = 2.7 Hz, 1H), 6.84 (d, J = 8.7 Hz, 1H), 4.16 (t, J = 5.4 Hz, 2H), 3.76 (t, J = 4.5 Hz, 4H), 2.84 (t, J = 5.4 Hz, 2H), 2.61 (t, J = 4.5 Hz, 4H), MS (ESI) [M + H]$^+$ = 468.1 |
| 40 | $^1$H NMR (300 MHz, CDCl$_3$) δ 7.67 – 7.59 (m, 2H), 7.39 (d, J = 9.0 Hz, 2H), 7.26 (d, J = 9.0 Hz, 2H), 7.07 (t, J = 7.8 Hz, 1H), 6.79 (s, 1H), 4.34 (t, J = 6.9 Hz, 2H), 3.82 (t, J = 4.5 Hz, 4H), 3.69 (t, J = 4.5 Hz, 4H), 3.05 (t, J = 5.4 Hz, 2H), 2.78 (t, J = 6.9 Hz, 2H), 2.66 – 2.60 (m, 4H), 2.57 – 2.48 (m, 6H), 1.82 (t, J = 5.4 Hz, 2H). MS (ESI) [M + H]$^+$ = 594.4 |
| 41 | $^1$H NMR (300 MHz, CDCl$_3$) δ 7.95 (d, J = 2.7 Hz, 1H), 7.81 (d, J = 9.0 Hz, 1H), 7.70 (dd, J = 7.8, 1.5 Hz, 1H), 7.66 (d, J = 9.0 Hz, 1H), 7.61 – 7.56 (m, 1H), 7.54 (dd, J = 7.8, 1.5 Hz, 1H), 7.19 (t, J = 7.8 Hz, 1H), 6.49 (d, J = 9.0 Hz, 1H), 4.32 – 4.21 (m, 2H), 3.60 (t, J = 4.5 Hz, 4H), 2.81 (t, J = 6.3 Hz, 2H), 2.49 (t, J = 4.5 Hz, 4H). MS (ESI) [M + H]$^+$ = 497.1 |
| 42 | $^1$H NMR (300 MHz, CDCl$_3$) δ 7.91 (d, J = 9.0 Hz, 1H), 7.73 (dd, J = 7.8, 1.2 Hz, 1H), 7.58 (dd, J = 7.8, 1.2 Hz, 1H), 7.52 (br s, 1H), 7.22 (t, J = 7.8 Hz, 1H), 7.05 (d, J = 8.7 Hz, 1H), 6.82 (d, J = 8.7 Hz, 1H), 6.73 (d, J = 9.0 Hz, 1H), 3.54 (t, J = 4.5 Hz, 4H), 3.21 (t, J = 6.0 Hz, 2H), 2.60 (t, J = 6.0 Hz, 2H), 2.40 (t, J = 4.5 Hz, 4H). MS (ESI) [M + H]$^+$ = 467.2 |

TABLE II-continued

| Ex | Characterizations |
|---|---|
| 43 | $^1$H NMR (300 MHz, CDCl$_3$) δ 8.11 (d, J = 9.3 Hz, 1H), 7.56 (d, J = 8.4 Hz, 1H), 7.36 (d, J = 9.0 Hz, 2H), 7.30 (d, J = 9.0 Hz, 2H), 6.59 (d, J = 9.3 Hz, 1H), 6.53 (d, J = 8.4 Hz, 1H), 4.34 (t, J = 6.9 Hz, 2H), 4.22 (t, J = 5.7 Hz, 2H), 3.72 (t, J = 4.5 Hz, 4H), 3.65 (t, J = 4.5 Hz, 4H), 2.88 (t, J = 5.7 Hz, 2H), 2.76 (t, J = 6.9 Hz, 2H), 2.63 – 2.55 (m, 8H).<br>MS (ESI) [M + H]$^+$ = 581.2 |
| 44 | $^1$H NMR (300 MHz, CDCl$_3$) δ 8.25 (d, J = 9.3 Hz, 1H), 7.53 (d, J = 8.4 Hz, 1H), 7.24 (d, J = 8.7 Hz, 1H), 6.64 (d, J = 9.3 Hz, 2H), 6.59 (d, J = 8.7 Hz, 1H), 6.52 (d, J = 8.4 Hz, 1H), 4.21 (t, J = 5.4 Hz, 2H), 3.72 (t, J = 4.5 Hz, 4H), 2.88 (t, J = 5.4 Hz, 2H), 2.61 (t, J = 4.5 Hz, 4H), |
| 46 | $^1$H NMR (300 MHz, CDCl$_3$) δ 8.40 (d, J = 7.2 Hz, 1H), 8.34 (d, J = 8.8 Hz, 1H), 8.18 (d, J = 8.8 Hz, 1H), 7.90 (d, J = 7.2 Hz, 1H), 7.85 (d, J = 7.9 Hz, 1H), 7.56 (t, J = 7.9 Hz, 1H), 6.98 (s, 1H), 6.53 (d, J = 7.9 Hz, 1H).<br>$^{13}$C NMR (75 MHz, CDCl3) δ 161.6, 151.2, 143.4, 142.3, 138.7, 138.2, 137.4, 133.4, 130.6, 129.1, 127.6, 126.7, 120.2, 119.7, 102.3.<br>MS (ESI) [M + H]$^+$ = 325.1 |
| 47 | $^1$H NMR (300 MHz, CDCl$_3$) δ 8.33 (d, J = 7.5 Hz, 1H), 8.18 (d, J = 8.7 Hz, 1H), 8.08 (d, J = 8.7 Hz, 1H), 7.60 (d, J = 2.4 Hz, 1H), 7.10 (d, J = 2.4 Hz, 1H), 6.96 (s, 1H), 6.50 (dd, J = 7.5, 1.8 Hz, 1H), 4.25 (t, J = 5.5 Hz, 2H), 3.86 – 3.69 (m, 4H), 2.89 (t, J = 5.5 Hz, 2H), 2.73 – 2.54 (m, 4H).<br>MS (ESI) [M + H]$^+$ = 454.2 |
| 48 | $^1$H NMR (300 MHz, CDCl$_3$) δ 8.12 (d, J = 8.8 Hz, 1H), 7.73 (d, J = 8.1 Hz, 1H), 7.66 (d, J = 8.1 Hz, 1H), 7.46 (d, J = 9.1 Hz, 2H), 7.38 – 7.22 (m, 3H), 7.12 (d, J = 8.8 Hz, 1H).<br>$^{13}$C NMR (75 MHz, CDCl3) δ 161.5, 151.9, 145.9, 142.7, 140.5, 132.0, 130.3, 127.0, 126.4, 125.1, 122.8, 122.2, 119.0 (t, J = 255 Hz), 113.6.<br>MS (ESI) [M + H]$^+$ = 340.1 |
| 49 | $^1$H NMR (300 MHz, CDCl$_3$) δ 8.03 (d, J = 8.7 Hz, 1H), 7.48 (d, J = 2.7 Hz, 1H), 7.44 (d, J = 9.0 Hz, 2H), 7.17 (d, J = 9.0 Hz, 2H), 7.10 (d, J = 8.7 Hz, 1H), 7.02 (d, J = 2.7 Hz, 1H), 4.19 (t, J = 5.7 Hz, 2H), 3.75 (t, J = 4.5 Hz, 4H), 2.85 (t, J = 5.7 Hz, 2H), 2.61 (t, J = 4.5 Hz, 4H).<br>MS (ESI) [M + H]$^+$ = 469.1 |
| 50 | $^1$H NMR (300 MHz, CDCl$_3$) δ 8.52 (d, J = 8.7 Hz, 1H), 7.59 (d, J = 8.4 Hz, 1H), 7.45 (d, J = 9.0 Hz, 2H), 7.27 (d, J = 9.0 Hz, 2H), 7.07 (d, J = 8.7 Hz, 1H), 6.67 (d, J = 8.4 Hz, 1H), 4.29 – 4.20 (m, 2H), 3.79 – 3.70 (m, 4H), 2.98 – 2.88 (m, 2H), 2.71 – 2.56 (m, 4H).<br>MS (ESI) [M + H]$^+$ = 469.1 |
| 51 | $^1$H NMR (300 MHz, DMSO) δ 10.84 (s, 1H), 9.57 (s, 1H), 8.58 (d, J = 5.1 Hz, 1H), 8.31 (d, J = 8.8 Hz, 1H), 7.78 (s, 1H), 7.70 (s, 1H), 7.49 (d, J = 8.8 Hz, 1H), 7.36 (d, J = 5.1 Hz, 1H).<br>MS (ESI) [M + H]$^+$ = 420.1 |
| 52 | $^1$H NMR (300 MHz, DMSO) δ 9.23 (d, J = 9.1 Hz, 1H), 8.21 (d, J = 9.1 Hz, 1H), 7.79 (t, J = 7.5 Hz, 2H), 7.46 – 7.18 (m, 5H).<br>MS (ESI) [M + H]$^+$ = 435.0 |
| 53 | $^1$H NMR (300 MHz, DMSO) δ 9.92 (s, 1H), 8.27 (d, J = 8.7 Hz, 2H), 8.15 (d, J = 9.0 Hz, 1H), 7.65 (s, 1H), 7.54 (s, 1H), 7.35 (d, J = 8.7 Hz, 2H). 7.17 (d, J = 9.0 Hz, 1H),<br>MS (ESI) [M + H]$^+$ = 435.0 |

Pharmacological Data

The compounds of the invention have been the subject of pharmacological tests which have demonstrated their relevance as active substances in therapy and in particular for preventing inflammatory disease.

Example 7: Modulation of miR-124 Expression by Quinoline Derivatives on an Inflammatory Bowel Disease In Vivo Model A. Material & Methods
Ex Vivo Studies
Extraction of PBMC Using a FICOLL™ Gradient For that purpose, Peripheral blood mononuclear cells (PBMCs) of healthy donors have been isolated by centrifugation on a FICOLL™ gradient according to standard protocols.

Briefly, 60-70 mL of buffy-coat are poured in a flask of 175 cm$^2$, and the volume is adjusted to 300 mL using PBS in order to obtain a dilution of about 5-fold of the buffy coat. 38 mL of diluted Buffy are then added to Falcon™ tubes of 50 mL comprising 12 mL of FICOLL™ (Histopack-1077) at ambient temperature. The preparation is centrifugated for 30 minutes at 515 rcf at ambient temperature. The lymphocyte ring is recovered from the Falcon™ tube with a transfer pipette (Pastette®) and then washed with PBS using centrifugation for 10 minutes at 290 rcf and at ambient temperature until the supernatant becomes clear.

The cells are then resuspended at 37° C. to a density of 1.5×10$^6$ cells/mL in RPMI Glutamax medium (Life Technologies Ref 61870-010) supplemented with 10% fetal calf serum (FCS) (Thermo Fischer Ref SV30160.03) and without activation. Cells are incubated for 48 hours at 37° C. under 5% CO$_2$.

Treatment of Cells with Screened Molecules

Six-well plates are used for the screening. Within each well comprising 3.10$^6$ cell/4 ml RPMI supplemented with 10% fetal calf serum and 40 U/mL IL-2 (Peprotech Ref 200-02) are added screened molecules. 100% DMSO (4 μL) is added to the well and tested as a negative control.

Each tested condition is set up as described here below and the final corresponding volume is adjusted accordingly in the well:
1) Quinoline derivatives in 100% DMSO—(5 μM and final volume 4 μL)
2) Antiretroviral drugs: Maraviroc, Efavirenz, Darunavir, AZT (10 μM for all—final volume 4 μL).

The wells are incubated for three days at 37° C. under 5% CO$_2$ Medium is changed (Day 3) according to standard protocols. Briefly, plates are centrifugated at 290 rcf for 5 minutes and 3 mL of supernatant is removed. 3 mL of RPMI supplemented with 10% fetal calf serum and 40 U/mL IL-2 is then added with 3 μL of a stock solution of screened molecule at 5 mM in 100% DMSO or 3 μL of 100% DMSO as a negative control.

Extraction of miRNAs (Day 6)

Cells are recovered within Falcon™ tubes of 15 mL, centrifugated at 290 rcf for 5 minutes, and then washed in 10 mL PBS and further centrifugated at 290 rcf for 5 minutes. Cells are then resuspended in 1 mL PBS and counted.

$6 \times 10^6$ cells are recovered and centrifugated at 290 rcf for 5 minutes. The cell pellet is lysed in 300 μL of ML lysis buffer from the Macherey Nagel Nucleospin® miRNA extraction kit (Macherey Nagel Ref 740971), and further stored at −20° C.

5 μL of $2 \times 10^8$ copies/μL of spike-in control (Ce_miR-39 from QIAGEN©—reference 219610 of SEQ ID No 6) are added for each sample. The miRNA extraction is achieved using the protocol from Macherey Nagel Nucleospin® miRNA extraction kit using an elution volume for RNAs of 50 μL and miRNAs of 30 μL, and further stored at −20° C.

Reverse Transcription of miRNAs (Day 6)

The reverse transcription step is followed for 12 μL of miRNA using the miScript RT II reverse transcription (RT) kit from QIAGEN© using the miScript HiSpec buffer, and further stored at −20° C.

Quantitative PCR of miRNAs (Day 6)

The quantitative PCR step is achieved using the QIAGEN© miScript SYBR® Green PCR kit and miScript Primer Assays according to the manufacturer's protocol.

Composition of the miScript Reaction Mix for 384-Well Plates:

| Mix | μL/reaction |
| --- | --- |
| 2X SYBR ® Green mix | 5 |
| 10X Universal Primer | 1 |
| 10X Primer Assay | 1 |
| H₂O | 2 |
| Total Mix volume: | 9 |
| Template cDNA in H₂O (*) | 1 |
| Final volume: | 10 |

(*) cDNA prepared using the miScript II RT kit

The reaction is repeated in triplicates in a 384-well plate according to the manufacturer's protocol on a LightCycler® 380 Roche Real-Time PCR system. Cycling conditions are also set up according to the manufacturer's protocol:

| Step | Time | Temperature |
| --- | --- | --- |
| Initial activation step | 15 min | 95° C. |
| 3-step cycling: | | |
| Denaturation | 15 s | 94° C. |
| Annealing | 30 s | 55° C. |
| Extension | 30 s | 70° C. |
| Cycle number | 40 cycles | |

Relative quantification of qPCR is known in the Art and is further detailed below.

Relative Quantification

From a dilution to the $\frac{1}{10}^{th}$ in H₂O for the miR-124 qPCR (Hs_miR-124a) or to the $\frac{1}{100}^{th}$ for reference/housekeeping gene qPCR (Hs_miR-26a and Hs_miR-191, using miScript Primer Assays (Hs_miR-124a, Hs_miR-26a and Hs_miR-191 or QIAGEN©—references ms00006622, ms00029239 and ms00003682).

The analysis is achieved using relative quantification models without efficiency correction ($2^{-\Delta\Delta C_p}$) using the average of crossing points (Cp) values from triplicates of miR-124 and the average of the average of triplicates of miR-26a and miR-191.

B. Results

One set of donors (1 to 7 donors tested for each compound) have been evaluated in the presence of different compounds of formula (I).

Using the protocol described above the mean fold change (in comparison to DMSO) in miR-124 expression was assessed with different donors (either 1 to 7) by relative quantification and is presented in the Table III herebelow:

TABLE III

| | Fold-change compared to DMSO treated cells (Relative quantification) | | Number of |
| --- | --- | --- | --- |
| Molecule | Mean | SD | donors tested |
| 1 | 31.96 | 7.25 | 3 |
| 23 | 45.09 | 7.44 | 3 |
| 45 | 34.21 | 6.22 | 3 |
| 2 | 66.68 | 13.86 | 2 |
| 3 | 48.52 | 12.71 | 3 |
| 24 | 32.48 | 21.76 | 7 |
| 12 | 16.33 | 15.12 | 4 |
| 4 | 24.37 | — | 1 |
| 25 | 14.28 | 6.50 | 2 |
| 5 | 26.76 | 8.45 | 3 |
| 6 | 30.94 | 12.28 | 3 |
| 26 | 6.13 | 1.18 | 2 |
| 27 | 1.42 | 0.19 | 3 |
| 7 | 7.54 | — | 1 |
| 28 | 22.20 | 8.25 | 3 |
| 8 | 7.97 | 2.66 | 3 |
| 30 | 9.88 | 8.75 | 4 |
| 9 | 111.77 | 75.69 | 2 |
| 10 | 21.08 | 13.46 | 3 |
| 48 | 23.98 | 11.01 | 4 |
| 46 | 6.23 | 4.38 | 6 |
| 11 | 17.42 | — | 1 |
| Maraviroc | 0.73 | 0.56 | 4 |
| Effavirenz | 0.46 | 0.27 | 4 |
| Darunavir | 1.08 | 0.89 | 4 |
| AZT | 0.90 | 0.55 | 4 |

Thus, experimental evidence shows that the above-mentioned quinoline derivatives of formula (I) up-regulate the expression levels of miR-124 in PBMCs, when compared to a reference value established on untreated PBMCs.

In contrast none of the known antiretroviral (Maraviroc, Effavirenz, Darunavir or AZT) has any significant effect on the overexpression of miR-124 in PBMCs from four donors.

Example 8: Effect of Quinoline Derivatives on the (DSS-) Induced Colitis Model

A. Material & Methods
Mouse Models
DSS Model

A commonly used mouse model of inflammatory bowel disease is the Dextran Sulphate Sodium (DSS-) induced colitis model. Typical histological changes of acute DSS-colitis are mucin depletion, epithelial degeneration and the eventual destruction of the mucosal barrier which leads to inflammation and colitis.

Figure 2:
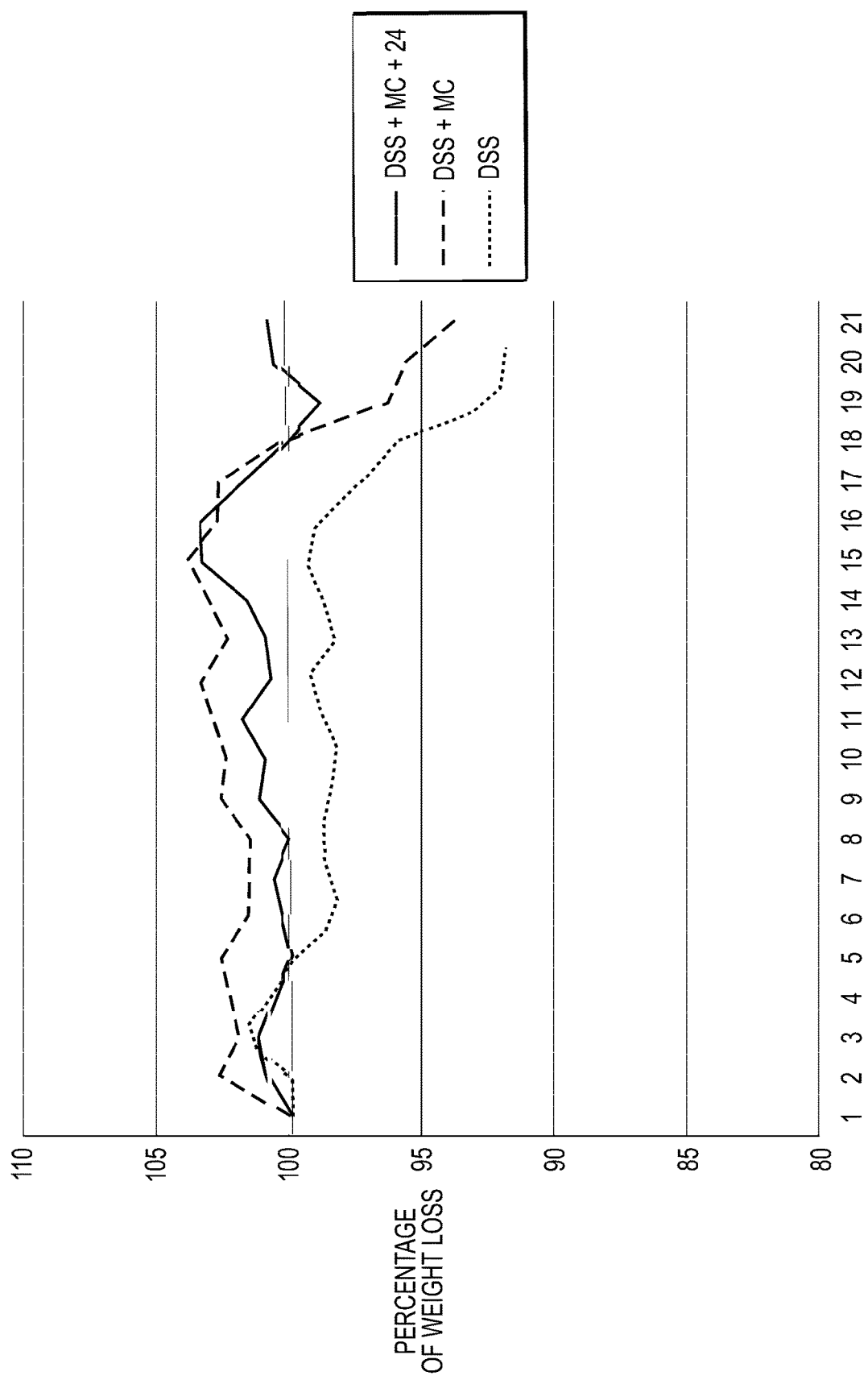
FIG. 2: Dextran sulphate sodium (DSS-) induced colitis model 2—Variation of the percentage of weight loss over time (days), on a DSS-mouse model, after a second cycle of DSS in the presence of quinoline derivative compound (24) as defined hereinafter. The percentage of weight loss (%) is indicated in the y-axis. DSS treatment started on day 12 for a period of 5 days (x-axis). Gavage with a quinoline derivative in methylcellulose (MC), or MC only, occurs between days 3 to 29.

Three groups of 6-week-old C57BL/6 mice (8 mice each) received DSS administration in the drinking water (2.5%) for 9 days (FIGS. 1-2). Weight loss and water consumption was measured every day. The latter was determined by measuring the volume loss of the drinking water in the respective devices. The mice were treated by gavage with 200 ul of 0.5 MC alone (DSS+MC group) or together with 40 mg/kg of compound 24 (DSS+MC+24 group). At the point when control mice have loosed up to 20% of their weight (DSS), the treatment with DSS is stopped and replaced with drinking water. The other treatments were continued for 21 days.

Figure 3:
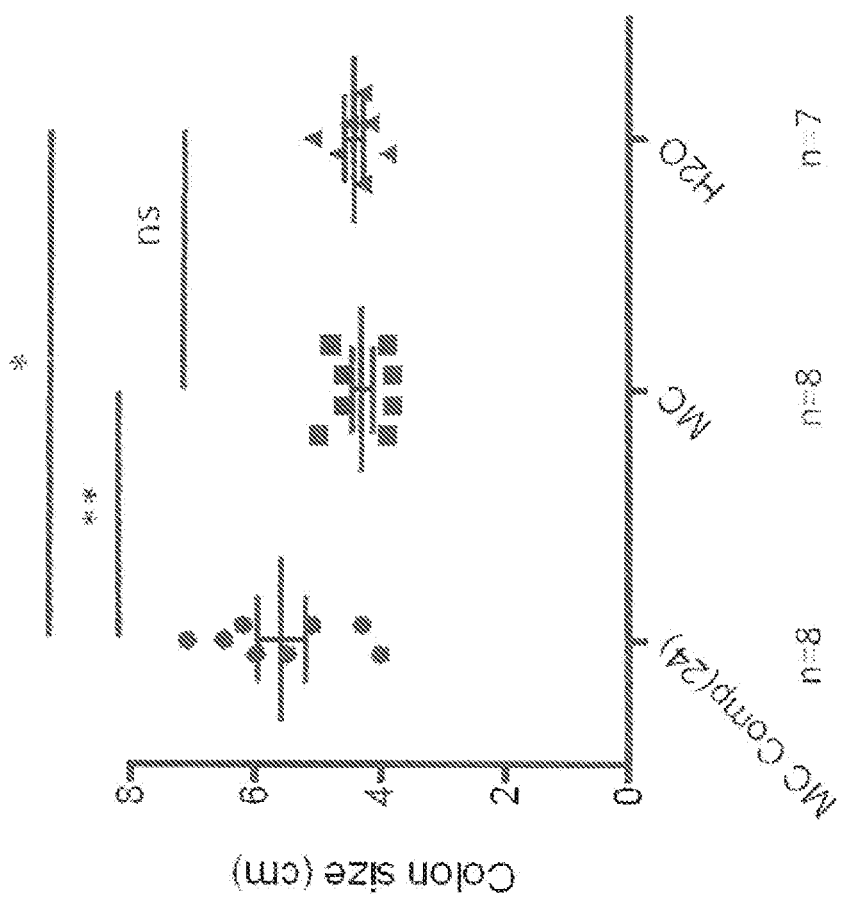
FIG. 3: Dextran sulphate sodium (DSS-) induced colitis model—Colons were removed 2-3 days upon a second DSS treatment (for 5 days) and variation of colon size (cm) was measured. (ns) marks a non-statistically significant difference. Statistical analysis was performed using Mann-Whitney test, asterisk indicates a significant difference ($p<0.5$), two asterisks indicate a very significant difference ($p<0.05$)

Three groups of 16-week-old C57BL/6 mice (7 mice each) received 2.5% DSS in drinking water (FIG. 3). The mice were treated by gavage with 200 ul of 0.5 MC alone (DSS+MC group) or together with 40 mg/kg of compound 24 (DSS+MC+24 group). The mice were treated with DSS for 6 days and at the point when control mice have loosed up to 15% of their weight (DSS), all the mice were euthanized and colon were taken for further analyses.

Figure 4:
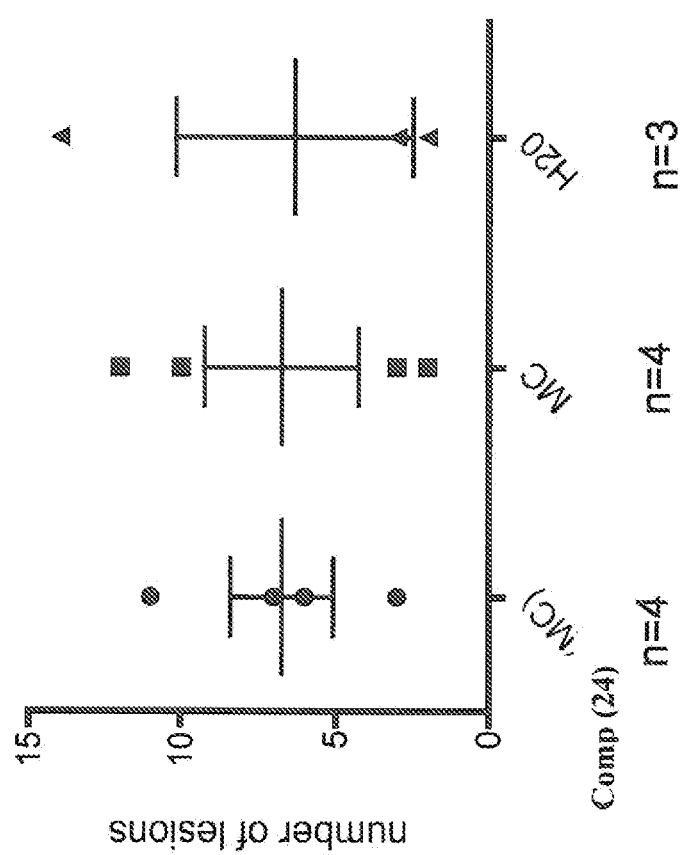
FIG. 4: Dextran sulphate sodium (DSS-) induced colitis model—Colons were removed 3 days upon a second DSS treatment and analyzed for lesion numbers. The lesions were observed under microscope and measured.
Figure 5:
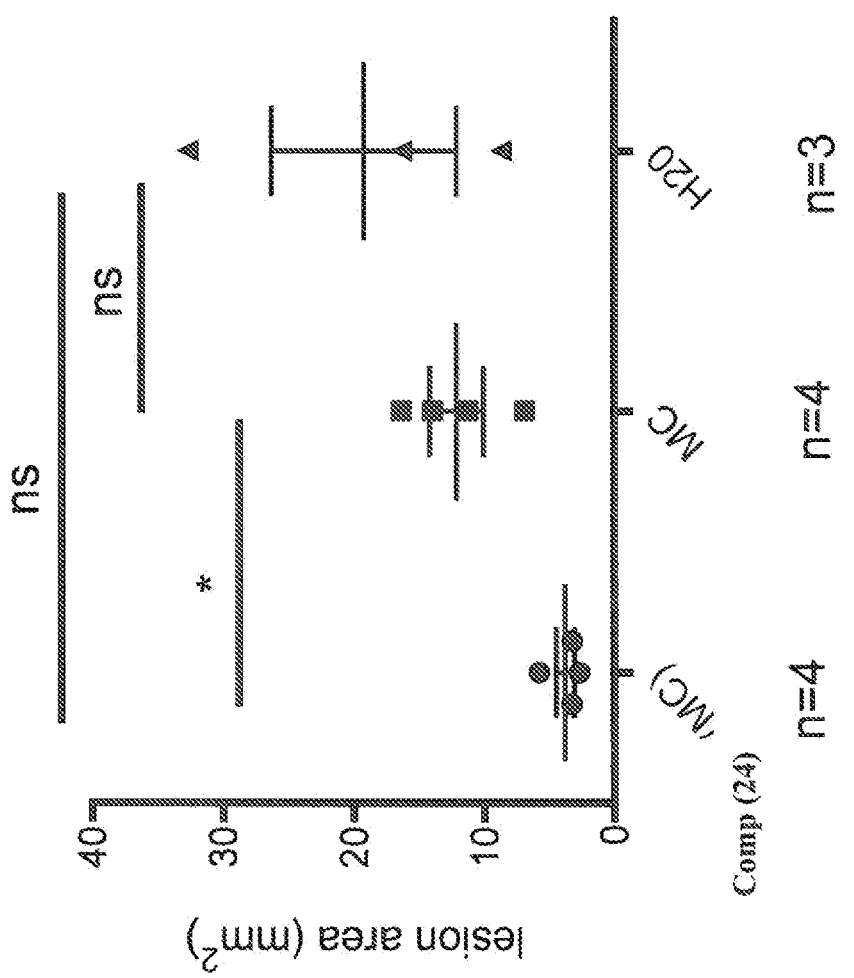
FIG. 5: Dextran sulphate sodium (DSS-) induced colitis model—Colons were removed 3 days upon a second DSS treatment and lesion area ($mm^2$) was determined.
Figure 6:
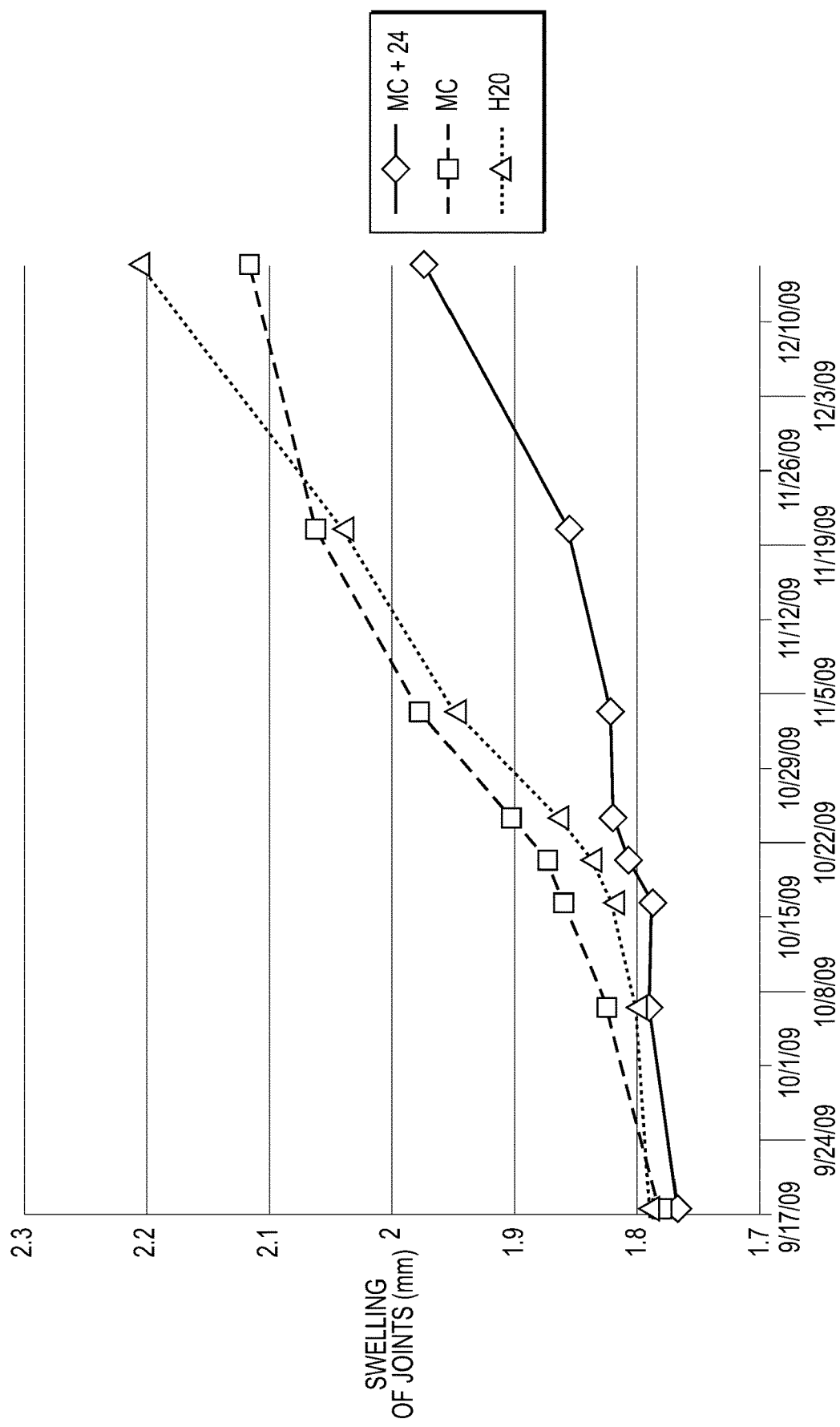
FIG. 6: Collagen induced arthritis model—Variation of the swelling of joints (mm) over time (weeks) on a mean cohort of 10 individuals. Swelling of joints (mm) is indicated in the y-axis. The variation between untreated vs treated groups is assessed over 12 weeks.

Colons were measured using a ruler and for histological analysis the entire colon was prepared according to the Swiss roll procedure (Whittem el al.; "Murine Colitis Modeling using Dextran Sulfate Sodium (DSS)", J Vis Exp 2010 (35) 1652) fixed with formaldehyde and embedded in paraffin. 4 µm sections were de-paraffinized and stained with hematoxylin and eosin and analyzed for lesion size and other alterations (FIGS. 4-6). We compared untreated and treated mice during the DSS-cycle with quinoline derivatives suspended in methylcellulose or methylcellulose (MC) only. Statistical analysis was performed using Mann-Whitney test, asterisk indicates a significant difference (p<0.5), two asterisks indicate a very significant difference (p<0.05)

B. Results

Results which are presented have been established using the quinoline derivative compound (24), for which the structure is represented herebelow for reference:

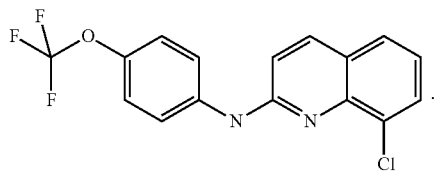

(24)

After 5 days of DSS-administration mice treated with the quinoline derivative manifested a weight loss of less then 1% in average in contrast to MC or untreated mice displayed a weight loss between 10% and 20% (FIGS. 1 and 2).

Notably, we noticed a higher water consumption of drug treated mice mirroring the disease dampening effect of quinoline derivatives. Quinoline derivative treatment did also significantly control weight loss in mice during the second administration of DSS indicating that mice do not become unresponsive and that quinoline derivatives are suitable for repetitive administration. After one cycle of DSS the length of the colon in quinoline derivatives treated mice (6.4 cm+/−0.6 cm) was significantly larger when compared to MC only treated (5.9 cm+/−0.8 cm) and untreated (5.8 cm+/−0.8 cm) mice (FIG. 3). This difference was even more pronounced in mice that received two cycles of DSS the length of the colon in quinoline derivatives treated mice (5.7 cm+/−0.9 cm) was significantly larger when compared to MC only treated (4.3 cm+/−0.5 cm) and untreated (4.4 cm+/−0.4 cm) mice (FIG. 3). The mice of the different cohorts developed comparable number of lesions (FIG. 4), but the average size of the lesion area was strikingly lower in quinoline-derivative treated mice, i.e. 2.1 mm$^2$ versus 8.4 mm$^2$ in MC only treated mice (FIG. 5). This difference was maintained in mice exposed to two DSS-cycles (3.8 mm$^2$ vs 12.2 mm$^2$).

Finally, we observed a decrease of alterations in lymphoid organs such as Peyer's Patches after two DSS-cycles suggesting that quinoline derivative treatment modulates immune responses.

Example 9: Effect of Quinoline Derivatives on the Collagen Induced Arthritis Model A. Material & Methods Mouse Models Collagen Induced Arthritis Model:

Groups of 9 to -10-week-old DBA/1 mice were immunized intradermally with bovine collagen type II emulsified in a 1:1 proportion with complete Freund's adjuvant. Mice were challenged 21 days after the first immunization and the phenotypic appearance of arthritis was evaluated by monitoring every second day the thickness of each hind paw ankle joint thickness was measured using a dial caliper (0- to 10-mm) test gauge using a thickness gage. Mice were treated daily for two weeks with quinoline derivatives candidates suspended in methylcellulose or methylcellulose (MC) only and the development of the disease was then monitored. Statistical analysis was performed using Mann-Whitney test, asterisk indicates a significant difference (p<0.5).

B. Results

Only one out of ten mice treated with the tested quinoline derivative compound (24), displayed signs of inflammation (in comparison, 8 out of 10 MC treated mice developed disease). Mice treated with quinoline derivatives displayed a significant decreased swelling in comparison to MC only treated mice (1.9 mm versus about 2.2 mm) (FIG. 6)

Therefore, the result of the tests carried out on the compounds disclosed in the present invention show that said compounds may be useful to treat and/or prevent inflammatory diseases as described further above.

For this purpose an effective amount of a said compound may be administered to an individual suffering from inflammatory diseases.

Thus, a compound according to the present invention may be implemented within pharmaceutical composition that may contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

Any route of administration may be used. For example, a compound of formula (I) can be administered by oral, parenteral, intravenous, transdermal, intramuscular, rectal, sublingual, mucosal, nasal, or other means. In addition, a compound of formula (I) can be administered in a form of pharmaceutical composition and/or unit dosage form.

In particular, pharmaceutical compositions of the invention may be administered orally and/or parenterally.

Suitable dosage forms include, but are not limited to, capsules, tablets (including rapid dissolving and delayed release tablets), powder, syrups, oral suspensions and solutions for parenteral administration.

The pharmaceutical composition may also contain another anti-inflammatory agent, well known to the man skilled in the art, in combination with a compound according to the present invention.

The invention claimed is:

1. An in vitro or ex vivo method for screening a quinoline derivative, or a pharmaceutically acceptable salt thereof, presumed effective in treating and/or preventing an inflammatory disease, comprising:
   a) providing an eukaryotic cell,
   b) bringing into contact said cell with the quinoline derivative or the pharmaceutically acceptable salt thereof,
   c) measuring an expression of miR-124 in said cell, and
   d) selecting the quinoline derivative or the pharmaceutically acceptable salt thereof presumed effective in treating and/or preventing an inflammatory disease when the level of expression of miR-124 measured in step c) is increased relatively to a reference value,
wherein the quinoline derivative is a compound of formula (I)

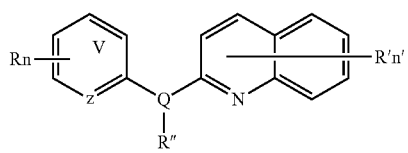

or a pharmaceutically acceptable salt thereof,
wherein:
   Z is C or N,
   V is C or N,

means an aromatic ring wherein V is C or N and when V is N, V is in ortho, meta or para of Z and forms respectively a pyridine, a pyridazine, a pyrimidine or a pyrazine group,
   R independently represents a hydrogen atom, a halogen atom or a group chosen among a —CN group, a hydroxyl group, a ($C_1$-$C_3$) fluoroalkyl group, a ($C_1$-$C_3$) fluoroalkoxy group, a ($C_3$-$C_6$) cycloalkyl group, a —$NO_2$ group, a —$NR_1R_2$ group, a ($C_1$-$C_4$) alkoxy group, a phenoxy group, a —$NR_1$—$SO_2$—$NR_1R_2$ group, a —$NR_1$—$SO_2$—$R_1$ group, a —$NR_1$—C(=O)—$R_1$ group, a —$NR_1$—C(=O)—$NR_1R_2$ group, a —$SO_2$—$NR_1R_2$ group, a —$SO_3H$ group, a —O—$SO_2$—$OR_3$ group, a —O—P(=O)—($OR_3$)($OR_4$) group, a —O—$CH_2$—$COOR_3$ group and a ($C_1$-$C_3$) alkyl group, said alkyl being optionally mono-substituted by a hydroxyl group,
   Q is N or O, provided that R" does not exist when Q is O,
   $R_1$ and $R_2$ are independently a hydrogen atom or a ($C_1$-$C_3$) alkyl group,
   $R_3$ and $R_4$ independently represent a hydrogen atom, $Li^+$, $Na^+$, $K^+$, $N^+(Ra)_4$ or a benzyl group,
   n is 1, 2 or 3,
   n' is 1, 2 or 3,
   R' independently represents a hydrogen atom or a group chosen among a ($C_1$-$C_3$) alkyl group, a halogen atom, a —$NO_2$ group, a —$NR_1R_2$ group, a morpholinyl group, a morpholino group, a N-methylpiperazinyl group, a ($C_1$-$C_3$) fluoroalkyl group, a —O—P(=O)—($OR_3$)($OR_4$) group, a —CN group, a group of formula (IIa), and a group of formula (IIIa):

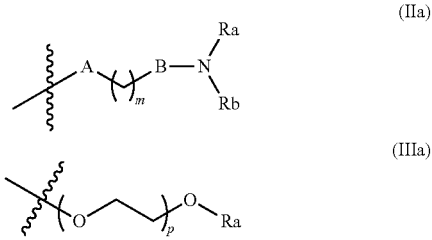

A is a covalent bond, an oxygen atom or NH,
   B is a covalent bond or NH,
   m is 1, 2, 3, 4 or 5,
   p is 1, 2 or 3,
   Ra and Rb independently represent a hydrogen atom, a ($C_1$-$C_5$) alkyl group or a ($C_3$-$C_6$) cycloalkyl group,
   Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group of formula (IIa) or a group of formula (IIIa), n' may be 2 or 3 only if other R' groups are different from said group of formula (IIa) or said group of formula (IIIa), and
   R" is a hydrogen atom, a ($C_1$-$C_4$) alkyl group or is a group of formula (IIa) as defined above.

2. The method according to claim 1, wherein said eukaryotic cell is a Peripheral Blood Mononuclear Cell (PBMC).

3. The method according to claim 1, wherein R" is a hydrogen atom, a ($C_1$-$C_4$) alkyl group or a group

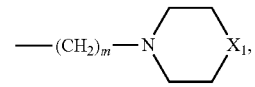

wherein
   m is 2 or 3 and
   $X_1$ is O, $CH_2$ or N—$CH_3$.

4. The method according to claim 1, wherein R independently represents a hydrogen atom, a methyl group, a methoxy group, a trifluoromethyl group, a trifluoromethoxy group, an amino group, a halogen atom, a fluorine, chlorine atom, or a —O—P(=O)—($OR_3$)($OR_4$) group.

5. The method according to claim 1, wherein R' independently represents a hydrogen atom, a halogen atom, a fluorine, chlorine atom, an amino group, a methyl group, a —O—P(=O)—($OR_3$)($OR_4$) group or a group

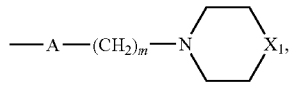

wherein
   A is O or NH,
   m is 2 or 3 and
   $X_1$ is O, $CH_2$ or N—$CH_3$, provided that when R' is such a group, n' is 1 or 2, and when n' is 2, the other R' group is different from said group or alternatively R' independently represents a hydrogen atom, a halogen atom, a fluorine, chlorine atom, a methyl group or a group

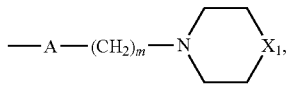

wherein
A is O or NH,
m is 2 and
$X_1$ is O, $CH_2$ or N—$CH_3$, provided that when R' is such a group, n' is 1 or 2, and when n' is 2, the other R' group is different from said group.

6. The method according to claim 1, wherein Q is N.

7. The method according to claim 1, wherein formula (I) is selected from

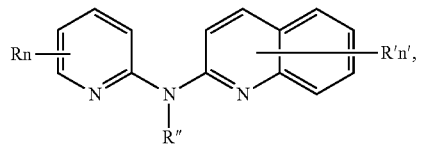

(Ia)

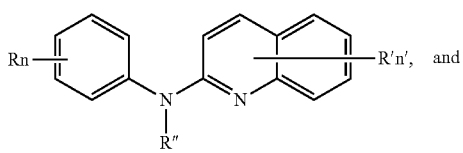

(Ib)

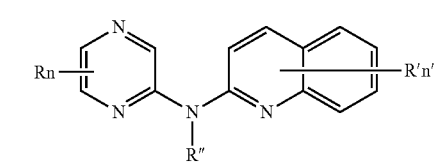

(Ic)

wherein R, R', R", n and n' are as defined in claim 1.

8. An in vitro or ex vivo method for assessing and following the efficacy of a compound of formula (I)

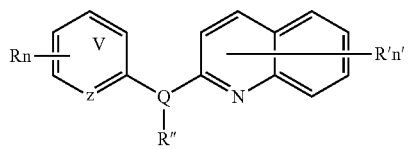

(I)

or a pharmaceutically acceptable salt thereof
wherein:
Z is C or N,
V is C or N,

means an aromatic ring wherein V is C or N and when V is N, V is in ortho, meta or para of Z, and forms respectively a pyridine, a pyridazine, a pyrimidine or a pyrazine group, R independently represents a hydrogen atom, a halogen atom or a group chosen among a —CN group, a hydroxyl group, a ($C_1$-$C_3$) fluoroalkyl group, a ($C_1$-$C_3$) fluoroalkoxy group, a ($C_3$-$C_6$) cycloalkyl group, a —$NO_2$ group, a —$NR_1R_2$ group, a ($C_1$-$C_4$) alkoxy group, a phenoxy group, a —$NR_1$—$SO_2$—$NR_1R_2$ group, a —$NR_1$—$SO_2$—$R_1$ group, a —$NR_1$—C(=O)—$R_1$ group, a —$NR_1$—C(=O)—$NR_1R_2$ group, a —$SO_2$—$NR_1R_2$ group, a —$SO_3H$ group, a —O—$SO_2$—$OR_3$ group, a —O—P(=O)—($OR_3$)($OR_4$) group, a —O—$CH_2$—$COOR_3$ group and a ($C_1$-$C_3$) alkyl group, said alkyl being optionally monosubstituted by a hydroxyl group, Q is N or O, provided that R" does not exist when Q is O,
$R_1$ and $R_2$ are independently a hydrogen atom or a ($C_1$-$C_3$) alkyl group,
$R_3$ and $R_4$ independently represent a hydrogen atom, $Li^+$, $Na^+$, $K^+$, $N^+(Ra)_4$ or a benzyl group,
n is 1, 2 or 3,
n' is 1, 2 or 3,
R' independently represents a hydrogen atom or a group chosen among a ($C_1$-$C_3$) alkyl group, a halogen atom, a —$NO_2$ group, a —$NR_1R_2$ group, a morpholinyl group, a morpholino group, a N-methylpiperazinyl group, a ($C_1$-$C_3$) fluoroalkyl group, a —O—P(=O)—($OR_3$) ($OR_4$) group, a —CN group, a group of formula (IIa), and a group of formula (IIIa):

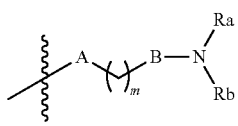

(IIa)

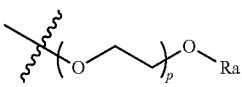

(IIIa)

A is a covalent bond, an oxygen atom or NH,
B is a covalent bond or NH,
m is 1, 2, 3, 4 or 5,
p is 1, 2 or 3,
Ra and Rb independently represent a hydrogen atom, a ($C_1$-$C_5$) alkyl group or a ($C_3$-$C_6$) cycloalkyl group,
Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group of formula (IIa) or a group of formula (IIIa), n' may be 2 or 3 only if other R' groups are different from said group of formula (IIa) or said group of formula (IIIa),
R" is a hydrogen atom, a ($C_1$-$C_4$) alkyl group or is a group of formula (IIa) as defined above,
the method comprising measuring the presence or level of expression of miR-124 in an eukaryotic cell from a biological sample, and comparing the presence or the level of expression of miR-124 to a control reference value, wherein the control reference value is obtained from an isolated biological sample obtained from a patient suffering from an inflammatory disease and receiving a treatment, the efficacy of the treatment being to be determined or monitored, the isolated biological sample being taken from the patient before administration of the treatment.

9. The method according to claim 8, wherein the biological sample is selected from a blood, a plasma, a serum, a saliva, an interstitial fluid, an urine sample, a cell sample, a cell culture, a cell line, a stem cell line, a Peripheral blood mononuclear cells (PBMC) containing sample, a tissue biopsy, an oral tissue, a gastrointestinal tissue, a skin, an oral mucosa sample, or a plurality of samples from a clinical trial, said sample being a crude sample or purified beforehand to various degrees prior to storage, processing, or measurement.

10. The method according to claim 1, wherein the level of expression of miR-124 is assessed by using nucleic acid assays, nucleic acid arrays, Northern blots or PCR-based methods.

11. The method according to claim 8, wherein the presence or level of expression of miR-124 is assessed by using nucleic acid assays, nucleic acid arrays, Northern blots or PCR-based methods.

12. The method according to claim 1, wherein the level of expression of miR-124 is measured in step c) by performing a method for the detection and quantification of nucleic acids, which may be a hybridation-based method, said hybridation-based methods including PCR and quantitative-PCR (qRT-PCR or q-PCR) techniques or reverse transcriptase/polymerase based techniques.

13. The method according to claim 8, wherein the presence or the level of expression of miR-124 is measured by performing a method for the detection and quantification of nucleic acids, which may be a hybridation-based method, said hybridation-based methods including PCR and quantitative-PCR (qRT-PCR or q-PCR) techniques or reverse transcriptase/polymerase based techniques.

14. The method according to claim 1, further comprising a sequencing step.

15. The method according to claim 8, further comprising a sequencing step.

16. The method according to claim 1, wherein the measuring of the level of expression of miR-124 in step c) comprises (i) a step of extraction of cellular mRNAs, (ii) a step of reverse transcription of mRNA to DNA using a reverse transcriptase and (iii) a step of DNA amplification from DNA obtained on the previous step.

17. The method according to claim 8, wherein the measuring of the presence or level of expression of miR-124 comprises (i) a step of extraction of cellular mRNAs, (ii) a step of reverse transcription of mRNA to DNA using a reverse transcriptase and (iii) a step of DNA amplification from DNA obtained on the previous step.

18. The method according to claim 1, wherein a modulation of the level of expression of miR-124 relatively to a control reference value from a healthy donor, is indicative of the efficacy of the quinoline derivative for treating and/or preventing an inflammatory disease.

19. The method according to claim 8, wherein an increased presence, or an increased level of expression, of miR-124 relative to the control reference value, is indicative of the efficacy of the compound of formula (I) for treating and/or preventing an inflammatory disease.

* * * * *

SEQUENCE LISTING

<160> NUMBER OF SEQ ID NOS: 6

<210> SEQ ID NO 1
<211> LENGTH: 85
<212> TYPE: RNA
<213> ORGANISM: Homo sapiens

<400> SEQUENCE: 1
aggccucucu cuccguguuc acagcggacc uugauuuaaa uguccauaca auuaaggcac     60
gcggugaaug ccaagaaugg ggcug                                          85

<210> SEQ ID NO 2
<211> LENGTH: 109
<212> TYPE: RNA
<213> ORGANISM: Homo sapiens

<400> SEQUENCE: 2
aucaagauua gaggcucugc ucuccguguu cacagcggac cuugauuuaa ugucauacaa     60
uuaaggcacg cggugaaugc caagagcgga gccuacggcu gcacuugaa               109

<210> SEQ ID NO 3
<211> LENGTH: 87
<212> TYPE: RNA
<213> ORGANISM: Homo sapiens

<400> SEQUENCE: 3
ugagggcccc ucugcguguu cacagcggac cuugauuuaa ugucuauaca auuaaggcac     60
gcggugaaug ccaagagagg cgccucc                                        87

<210> SEQ ID NO 4
<211> LENGTH: 20
<212> TYPE: RNA
<213> ORGANISM: Homo sapiens

<400> SEQUENCE: 4
uaaggcacgc ggugaaugcc                                                20

<210> SEQ ID NO 5
<211> LENGTH: 22
<212> TYPE: RNA
<213> ORGANISM: Homo sapiens

<400> SEQUENCE: 5
cguguucaca gcggaccuug au                                             22

<210> SEQ ID NO 6
<211> LENGTH: 22
<212> TYPE: RNA
<213> ORGANISM: Caenorhabditis elegans

<400> SEQUENCE: 6
ucaccgggug uaaaucagcu ug                                             22